US012144742B2

United States Patent
Betz et al.

(10) Patent No.: US 12,144,742 B2
(45) Date of Patent: Nov. 19, 2024

(54) IMPLANT SYSTEM AND METHODS OF USE

(71) Applicant: FOUNDATION SURGICAL GROUP, INC., Bradenton, FL (US)

(72) Inventors: Randal R. Betz, Bradenton, FL (US); Dale E. Whipple, Nashua, NH (US); Charlie Barfield, Hernando, MS (US); Dimitri K. Protopsaltis, Memphis, TN (US); Michael Sherman, Memphis, TN (US); Marc Burel, Perkasie, PA (US)

(73) Assignee: FOUNDATION SURGICAL GROUP, INC., Bradenton, FL (US)

( * ) Notice: Subject to any disclaimer, the term of this patent is extended or adjusted under 35 U.S.C. 154(b) by 0 days.

(21) Appl. No.: 18/328,876

(22) Filed: Jun. 5, 2023

(65) Prior Publication Data

US 2023/0310169 A1    Oct. 5, 2023

Related U.S. Application Data

(63) Continuation-in-part of application No. 18/051,732, filed on Nov. 1, 2022, now Pat. No. 11,883,300,
(Continued)

(51) Int. Cl.
*A61F 2/30* (2006.01)
*A61F 2/44* (2006.01)

(52) U.S. Cl.
CPC .. *A61F 2/4425* (2013.01); *A61F 2002/30405* (2013.01); *A61F 2002/443* (2013.01)

(58) Field of Classification Search
CPC .... A61F 2/4425; A61F 2/4455; A61F 2/4465; A61F 2/4611; A61F 2002/30405; A61F 2002/443; A61F 2002/4435
See application file for complete search history.

(56) References Cited

U.S. PATENT DOCUMENTS

| 583,455 A | 6/1897 | Bush |
| 4,047,524 A | 9/1977 | Hall |
(Continued)

FOREIGN PATENT DOCUMENTS

| AU | 2007317886 B2 | 3/2014 |
| CA | 1333209 | 11/1994 |
(Continued)

OTHER PUBLICATIONS

Ahn, J., Tabaraee, E., Bohl, D.D., Singh, K., Surgical management of adult spinal deformity: Indications, surgical outcomes, and health-related quality of life. Seminars in Spine Surgery, 29(2), 72-76, 2017, 5 pgs., https://doi.org/10.1053/j.semss.2016.12.001, Chicago, IL, USA.
(Continued)

*Primary Examiner* — Tracy L Kamikawa
(74) *Attorney, Agent, or Firm* — John Brooks Law LLC; John J. Brooks, III

(57) ABSTRACT

An implant system comprising a staple and a cage is disclosed. The implant system is secured to the bone by moving the staple rotationally and longitudinally whereby tines of the staple and opposing tines frictionally and mechanically engage or embed themselves in the bone side walls. For vertebral applications, the cage defines an upper surface plane, a lower surface plane and a cage surface angle between these two planes whereby the cage surface angle may alter an endplate surface plane of one or more vertebral body when the cage is implanted in a vertebral body. Implant systems may be configured for use as an interbody or intrabody implant system. The implant system may also be configured for use in arthrodesis procedures with other joints within the body. The implant system may further comprise an anchor frame or plate to further secure the cage and staple to the anatomy.

28 Claims, 58 Drawing Sheets

Related U.S. Application Data which is a continuation-in-part of application No. 17/676,609, filed on Feb. 21, 2022, now Pat. No. 11,806,247, which is a continuation of application No. 17/347,492, filed on Jun. 14, 2021, now Pat. No. 11,259,936, application No. 18/328,876, filed on Jun. 5, 2023 is a continuation-in-part of application No. 17/934,874, filed on Sep. 23, 2022, now Pat. No. 11,723,778, and a continuation-in-part of application No. 17/676,609, filed on Feb. 21, 2022, now Pat. No. 11,806,247.

(60) Provisional application No. 63/478,620, filed on Jan. 5, 2023, provisional application No. 63/369,330, filed on Jul. 25, 2022, provisional application No. 63/039,242, filed on Jun. 15, 2020, provisional application No. 63/349,136, filed on Jun. 5, 2022, provisional application No. 63/247,345, filed on Sep. 23, 2021.

(56) References Cited

U.S. PATENT DOCUMENTS

| | | | |
|---|---|---|---|
| 4,289,123 | A | 9/1981 | Dunn |
| 4,615,338 | A | 10/1986 | Ilizarov |
| 4,657,550 | A | 4/1987 | Daher |
| 4,723,540 | A | 2/1988 | Gilmer, Jr. |
| 5,395,372 | A | 3/1995 | Holt |
| 5,522,899 | A | 6/1996 | Michelson |
| 5,620,443 | A | 4/1997 | Gertzbein |
| 5,713,899 | A | 2/1998 | Marnay |
| 5,728,127 | A | 3/1998 | Asher |
| 5,776,199 | A | 7/1998 | Michelson |
| 5,947,969 | A | 9/1999 | Errico et al. |
| 5,951,553 | A | 9/1999 | Betz |
| 5,980,522 | A * | 11/1999 | Koros ............... A61F 2/446 606/62 |
| 6,287,308 | B1 | 9/2001 | Betz |
| 6,447,547 | B1 | 9/2002 | Michelson |
| 6,478,823 | B1 | 11/2002 | Michelson |
| 6,527,803 | B1 | 3/2003 | Crozet et al. |
| 6,623,484 | B2 | 9/2003 | Betz et al. |
| 6,821,298 | B1 | 11/2004 | Jackson |
| 6,984,234 | B2 | 1/2006 | Bray |
| 7,250,060 | B2 | 7/2007 | Trieu |
| 7,621,938 | B2 | 11/2009 | Molz, IV |
| 7,704,279 | B2 | 4/2010 | Moskowitz |
| 7,799,060 | B2 | 9/2010 | Lange |
| 7,833,245 | B2 | 11/2010 | Kaes et al. |
| 7,955,392 | B2 | 6/2011 | Dewey |
| 8,062,375 | B2 | 11/2011 | Glerum |
| 8,075,593 | B2 | 12/2011 | Hess |
| 8,097,037 | B2 | 1/2012 | Serhan et al. |
| 8,157,842 | B2 | 4/2012 | Phan |
| 8,241,330 | B2 * | 8/2012 | Lamborne .......... A61B 17/7061 606/248 |
| 8,267,997 | B2 | 9/2012 | Colleran |
| 8,273,129 | B2 | 9/2012 | Baynham et al. |
| 8,292,963 | B2 | 10/2012 | Miller |
| 8,353,913 | B2 | 1/2013 | Moskowitz |
| 8,403,959 | B2 * | 3/2013 | Dollinger .......... A61B 17/7065 606/248 |
| 8,409,287 | B2 | 4/2013 | Braddock, Jr. |
| 8,454,623 | B2 | 6/2013 | Patel |
| 8,496,689 | B2 | 7/2013 | Massoudi |
| 8,545,567 | B1 | 10/2013 | Krueger |
| 8,603,142 | B2 | 12/2013 | Robinson |
| 8,721,686 | B2 | 5/2014 | Gordon |
| 8,845,731 | B2 | 9/2014 | Weiman |
| 8,845,732 | B2 | 9/2014 | Weiman |
| 8,852,278 | B2 * | 10/2014 | Bellas ............... A61F 2/447 623/17.11 |
| 8,870,961 | B2 | 10/2014 | Thalgott |
| 8,894,708 | B2 | 11/2014 | Thalgott |
| 8,945,184 | B2 | 2/2015 | Hess |
| 8,979,927 | B2 | 3/2015 | Huntsman |
| 9,050,143 | B2 | 6/2015 | May |
| 9,055,981 | B2 | 6/2015 | Lamborne et al. |
| 9,107,760 | B2 | 8/2015 | Walters |
| 9,179,944 | B2 | 11/2015 | Boyer, II |
| 9,198,774 | B2 | 12/2015 | Pisharodi |
| 9,204,899 | B2 | 12/2015 | Buttermann |
| 9,283,091 | B2 | 3/2016 | Melkent |
| 9,375,238 | B2 | 6/2016 | Binder |
| 9,393,053 | B2 | 7/2016 | Fessler |
| 9,402,739 | B2 | 8/2016 | Weiman |
| 9,463,091 | B2 | 10/2016 | Brett |
| 9,566,166 | B2 | 2/2017 | Parry |
| 9,713,537 | B2 | 7/2017 | Bray, Jr. |
| 9,724,206 | B2 | 8/2017 | Aeschlimann |
| 9,750,618 | B1 | 9/2017 | Daffinson |
| 9,763,805 | B2 | 9/2017 | Cheng |
| 9,795,485 | B2 | 10/2017 | Allain |
| 9,833,262 | B2 | 12/2017 | Lim |
| 9,861,399 | B2 * | 1/2018 | Rogers ............. A61B 17/00234 |
| 9,889,020 | B2 | 2/2018 | Baynham |
| 9,889,022 | B2 | 2/2018 | Moskowitz |
| 9,956,007 | B2 | 5/2018 | Choi |
| 9,956,087 | B2 | 5/2018 | Seifert |
| 9,987,144 | B2 | 6/2018 | Seifert |
| 10,028,740 | B2 | 7/2018 | Moskowitz |
| 10,137,001 | B2 | 11/2018 | Weiman |
| 10,143,501 | B2 | 12/2018 | Northcutt |
| 10,149,703 | B2 | 12/2018 | Moskowitz |
| 10,195,045 | B2 | 2/2019 | Muller |
| 10,231,756 | B2 | 3/2019 | Buss |
| 10,251,643 | B2 | 4/2019 | Moskowitz |
| 10,307,265 | B2 | 6/2019 | Sack |
| 10,307,268 | B2 | 6/2019 | Moskowitz |
| 10,405,992 | B2 | 9/2019 | Sack |
| 10,413,426 | B2 | 9/2019 | Parry |
| 10,448,979 | B2 | 10/2019 | Fox |
| 10,478,319 | B2 | 11/2019 | Moskowitz |
| 10,492,919 | B2 | 12/2019 | Rashbaum |
| 10,531,961 | B2 | 1/2020 | Dinville |
| 10,588,753 | B2 | 3/2020 | Whipple et al. |
| 10,603,084 | B1 | 3/2020 | Sanders |
| 10,660,673 | B2 | 5/2020 | Maly |
| 10,687,877 | B2 | 6/2020 | Lavigne |
| 10,702,391 | B2 | 7/2020 | Ameil |
| 10,779,816 | B2 | 9/2020 | Goldstein |
| 10,864,081 | B2 | 12/2020 | Tyber |
| 10,925,752 | B2 | 2/2021 | Weiman |
| 10,973,649 | B2 | 4/2021 | Weiman |
| 11,065,128 | B2 | 7/2021 | Zappacosta |
| 11,135,069 | B2 | 10/2021 | Eisen |
| 11,259,936 | B2 | 3/2022 | Betz |
| 11,484,415 | B2 | 11/2022 | Kim |
| 11,723,778 | B1 | 8/2023 | Betz |
| 2003/0065396 | A1 | 4/2003 | Michelson |
| 2003/0135279 | A1 | 7/2003 | Michelson |
| 2003/0149482 | A1 | 8/2003 | Michelson |
| 2005/0165485 | A1 | 7/2005 | Trieu |
| 2006/0095136 | A1 | 5/2006 | McLuen |
| 2006/0241764 | A1 | 10/2006 | Michelson |
| 2010/0131010 | A1 | 5/2010 | Graf |
| 2011/0118842 | A1 | 5/2011 | Bernard et al. |
| 2011/0125269 | A1 | 5/2011 | Moskowitz |
| 2011/0144755 | A1 | 6/2011 | Baynham et al. |
| 2012/0150229 | A1 | 6/2012 | Hess |
| 2013/0274810 | A1 | 10/2013 | Fraser |
| 2014/0100662 | A1 | 4/2014 | Patterson et al. |
| 2014/0277154 | A1 | 9/2014 | Perry |
| 2015/0088256 | A1 | 3/2015 | Ballard |
| 2015/0105834 | A1 | 4/2015 | Bilger |
| 2016/0106549 | A1 | 4/2016 | Vestgaarden |
| 2016/0331544 | A1 * | 11/2016 | Braddock, Jr. ......... A61F 2/447 |
| 2018/0028327 | A1 | 2/2018 | Ballard |
| 2018/0243105 | A1 | 8/2018 | Vestgaarden |
| 2019/0298421 | A1 | 10/2019 | Capote |
| 2020/0323642 | A1 | 10/2020 | Vestgaarden |
| 2021/0386556 | A1 | 12/2021 | Betz |

(56) References Cited

U.S. PATENT DOCUMENTS

| | | |
|---|---|---|
| 2022/0015751 A1 | 1/2022 | Chevalier |
| 2022/0387182 A1 | 12/2022 | Bernard |
| 2024/0091025 A1 | 3/2024 | Vestgaarden |

FOREIGN PATENT DOCUMENTS

| | | |
|---|---|---|
| DE | 68921482 | 7/1995 |
| EP | 0425542 | 5/1991 |
| EP | 0637439 | 2/1995 |
| EP | 0734702 | 10/1996 |
| EP | 2725994 B1 | 5/2017 |
| JP | 1991505416 | 3/1991 |
| WO | 1990000037 | 1/1990 |
| WO | 2004089256 A1 | 10/2004 |
| WO | 2005007040 A1 | 1/2005 |
| WO | 2005007041 A1 | 1/2005 |
| WO | 2006086895 A1 | 8/2006 |
| WO | 2011057181 A1 | 5/2011 |
| WO | 2011057185 A1 | 5/2011 |
| WO | 2014145478 A1 | 9/2014 |
| WO | 2021230871 A1 | 11/2021 |
| WO | 2021257484 A1 | 12/2021 |
| WO | 2022133055 A1 | 6/2022 |

OTHER PUBLICATIONS

Magerl, F., Aebi, M., Gertzbein, S.D., Harms, J. Nazarian, S., A comprehensive classification of thoracic and lumbar injuries. European Spine Journal, 3(4), 184-201, 1994, 18 pgs., https://doi.org/10.1007/BF02221591.

Yang, Andres, Non-FInal Office Action for U.S. Appl. No. 15/402,112, dated Aug. 29, 2018, 9 pgs., USPTO, Alexandria VA, USA.

James Guille, The Feasibility, Safety, and Utility of Vertebral Wedge Osteotomies for the Fusionless Treatment of Paralytic Scoliosis SPINE vol. 28 No. 20s pp. S266-S274, 9 pgs., 2003, Lippincott Williams WIkins, Inc, USA.

Kevin Mccarthy, Clinical Efficacy of the Vertebral Wedge Osteotomy for the Fusionless Treatment of Paralytic Scoliosis SPINE vol. 35 No. 4 pp. 403-410, 8 pgs., 2010 Lippincott, Williams Wilkins, Inc., USA.

Betz RR; Cunningham B; Selgrath C; Drwery T; Sherman MC: Preclinical testing of a wedge-rod system for fusionless correction of scoliosis. Spine (Phila Pa 1976) 28(20S):S275-S278, 2003, 4 pgs., Philadelphia PA, USA.

Betz RR; Mulcahey MJ: New surgical treatments for scoliosis: vertebral body stapling and wedge osteotomies. Viewpoint, Shriners Hospitals for Children, www.shrinershq.org, Sep. 2001, as downloaded from www.SpineUniverse.com on Oct. 15, 2018, 4 pgs., USA.

Didelot, William P.; Kling, Thomas F. Jr.; Lindseth, Richard E.: Anterior Vertebral Osteotomies to Correct Lumbar Scoliosis Without Fusion, Ch. 47. In: Modern Anterior Scoliosis Surgery (Lenke, L.; Betz, R.; Harms, J., eds.), Thieme Medical Publishers, 2004, pp. 693-706, 7 pgs. (2 pgs per sheet), New York, USA.

Rodriquez, Kari, Written Opinion of the International Searching Authority for co-pending PCT Application No. PCT/US21/37285, dated Aug. 24, 2021, 7 pgs., United States Patent and Trademark Office, Alexandria, VA , USA.

Rodriquez, Kari, International Search Report for PCT Application No. PCT/US21/37285, dated Aug. 24, 2021, 2 pgs., United States Patent and Trademark Office, Alexandria, VA , USA.

Kamikawa, Tracy L., Office Action for U.S. Appl. No. 17/347,492, dated Aug. 6, 2021, 9 pgs., United States Patent and Trademark Office, Alexandria, VA , USA.

Kamikawa, Tracy L., Notice of Allowance for U.S. Appl. No. 17/347,492, dated Oct. 18, 2021, 26 pgs., United States Patent and Trademark Office, Alexandria, VA , USA.

Berven, Sigurd H.; Hu, Serena S.; Deviren, Vedat; Smith, Jason; Bradford, David S.: Lumbar End Plate Osteotomy in Adult Patients With Scoliosis, Jun. 2003, Clinical Orthopaedics and Related Research, No. 411, pp. 70-76, 7 pgs., San Francisco, Ca, USA.

Kamikawa, Tracy L., Restriction Requirement for U.S. Appl. No. 17/676,609, dated May 13, 2022, 8 pgs., United States Patent and Trademark Office, Alexandria, VA , USA.

Kamikawa, Tracy L., Notice of Allowance for U.S. Appl. No. 17/676,609, dated Jun. 23, 2022, 24 pgs., United States Patent and Trademark Office, Alexandria, VA , USA.

Negrelli Rodriguez, Christina, Non-Final Office Action for U.S. Appl. No. 15/404,129, dated Nov. 5, 2018, 26 pgs., USPTO, Alexandria VA, USA.

Negrelli-Rodriguez, Christina, Final Office Action for U.S. Appl. No. 15/404,129, dated Feb. 15, 2019, 20 pgs., USPTO, Alexandria VA, USA.

Negrelli-Rodriguez, Christina, Non-Final Office Action for U.S. Appl. No. 15/404,129, dated Aug. 16, 2019, 8 pgs., USPTO, Alexandria VA, USA.

Negrelli-Rodriguez, Christina, Notice of Allowance for U.S. Appl. No. 15/404,129, dated Nov. 13, 2019, 5 pgs., USPTO, Alexandria VA, USA.

N.H. Hart, S. Nimphius, T. Rantalainen, A. Ireland, A. Siafaikass, R.U. Newton, Mechanical basis of bone strength: influence of bone material, bone structure and muscle action, Journal of Muscoloskeletal and Neuro Interactions, 26 pages, 17(3): 114-139, Sep. 2017, GR.

Kamikawa, Tracy L., Notice of Allowance for U.S. Appl. No. 17/676,609, dated Nov. 15, 2022, 5 pgs., United States Patent and Trademark Office, Alexandria, VA , USA.

Waggle, Larry E. Jr., Non-Final Office Action for U.S. Appl. No. 17/934,874, dated Dec. 8, 2022, 48 pgs., USPTO, Alexandria VA, USA.

Kamikawa, Tracy L., Notice of Allowance for U.S. Appl. No. 18/051,732, dated Feb. 2, 2023, 21 pgs., United States Patent and Trademark Office, Alexandria, VA , USA.

Waggle, Larry E. Jr., Notice of Allowance for U.S. Appl. No. 17/934,874, dated Feb. 22, 2023, 36 pgs., USPTO, Alexandria VA, USA.

Kamikawa, Tracy L., Non-Final Office Action for U.S. Appl. No. 18/328,876, dated Aug. 14, 2023, 22 pgs., United States Patent and Trademark Office, Alexandria, VA , USA.

Matos, Taina, Invitation to Pay Additional Fees for PCT App. No. PCT/US2023/067912, 2 pgs., United States Patent and Tradeamark Office, Alexandria, VA, USA.

Matos, Taina, International Search Report and Written Opinion for PCT App. No. PCT/US2023/067912, Mailed Jan. 22, 2024, 16 pgs., United States Patent and Trademark Office, Alexandria, VA, USA.

Salima Filali, European Patent Office, Supplementary European Search Report and European search opinion, App. No. 21824991.0, Jun. 17, 2024, 11 pgs., European Patent Office, Munich, Germany.

* cited by examiner

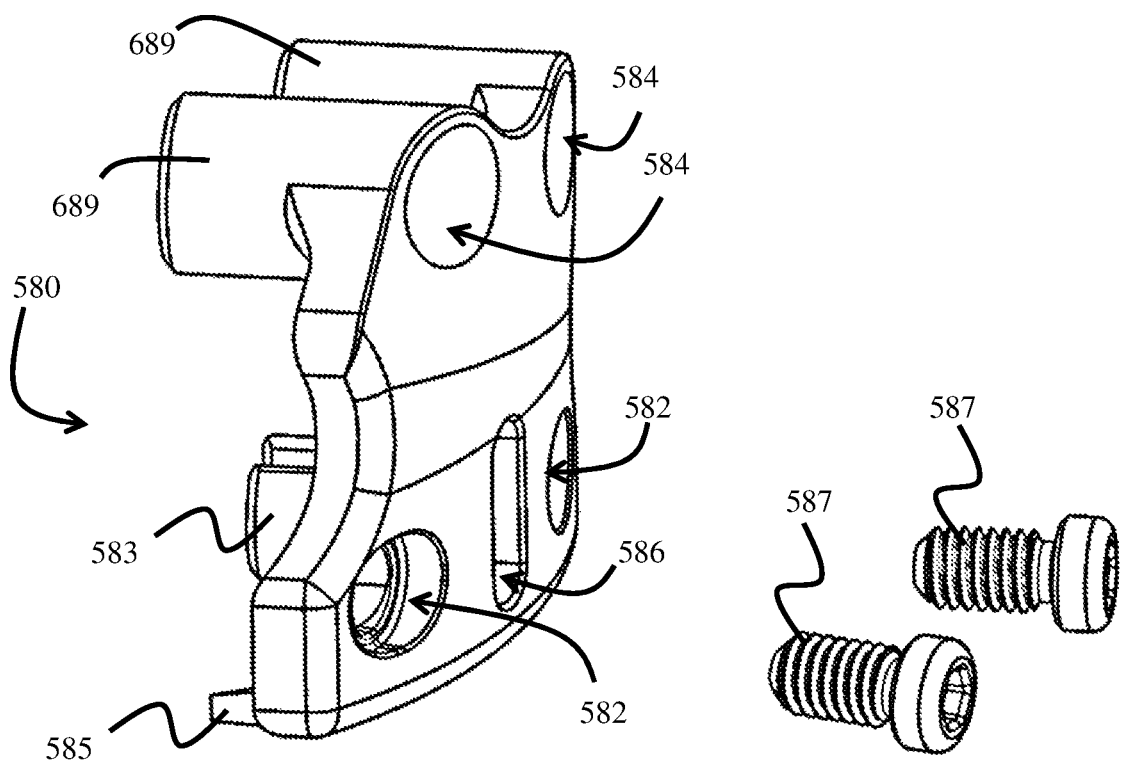
FIG. 5A
FIG. 5B
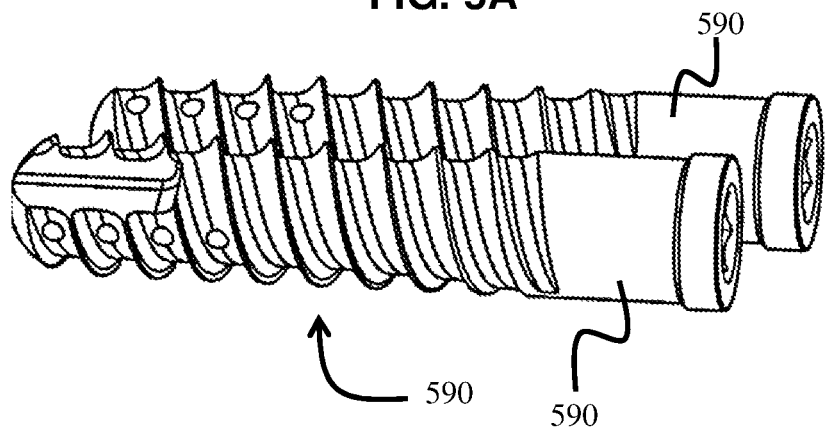
FIG. 5C
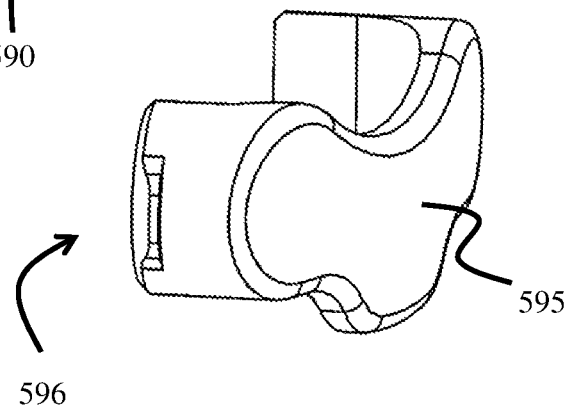
FIG. 5D

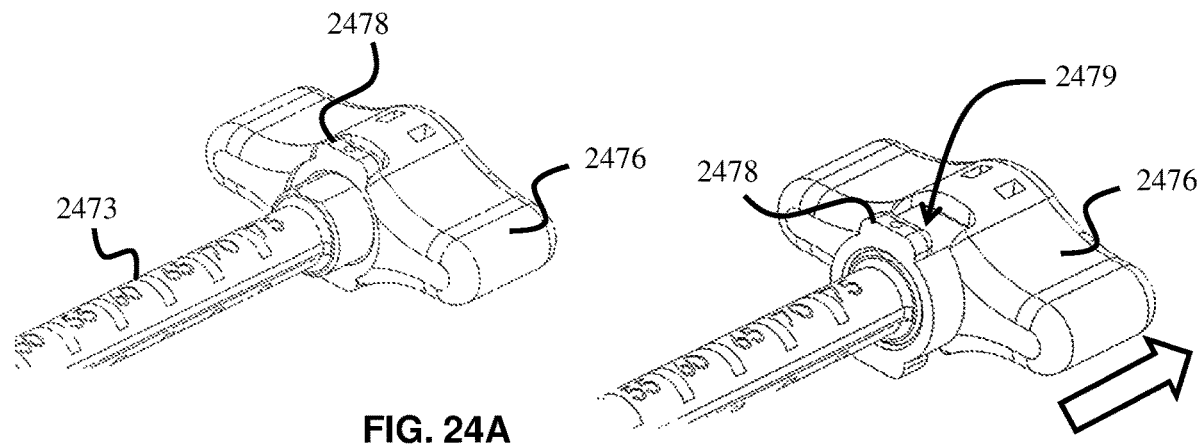
FIG. 24A
FIG. 24B
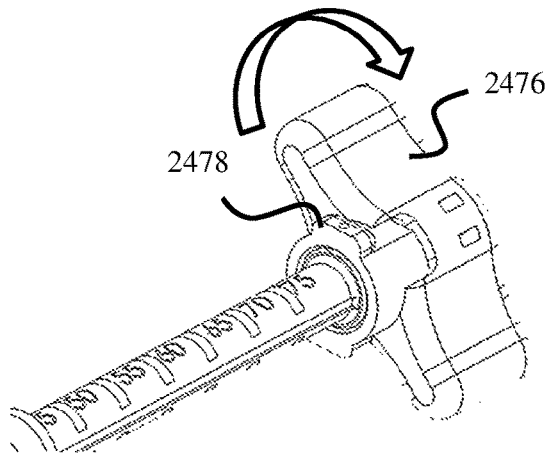
FIG. 24C
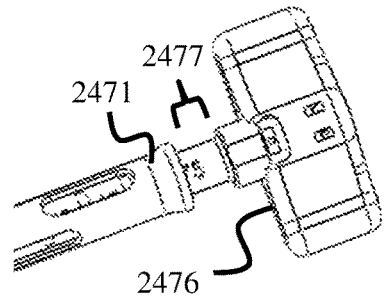
FIG. 24D
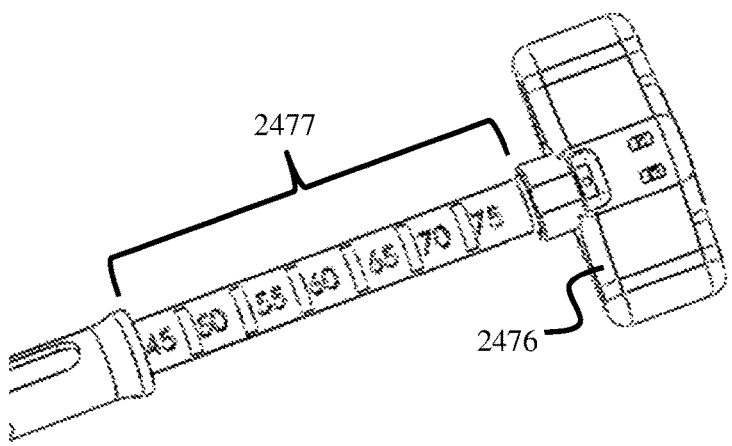
FIG. 24E

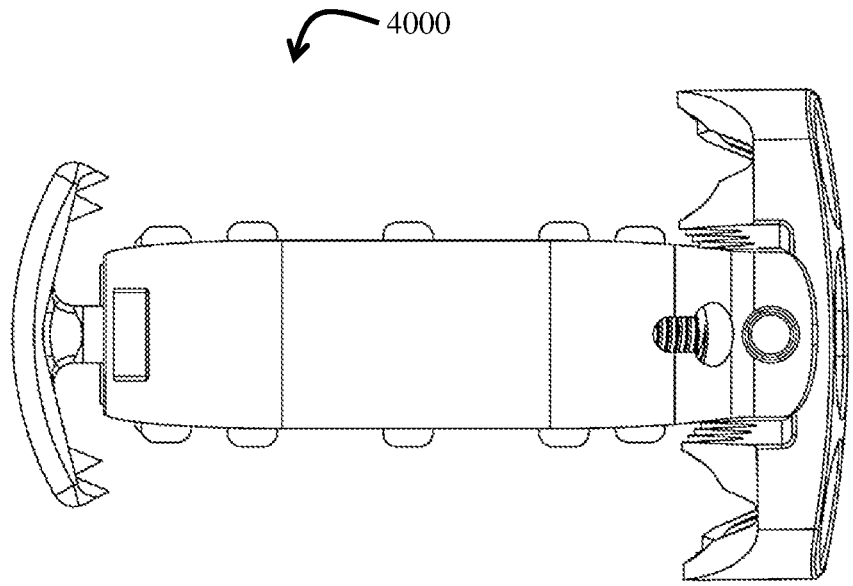
FIG. 40D
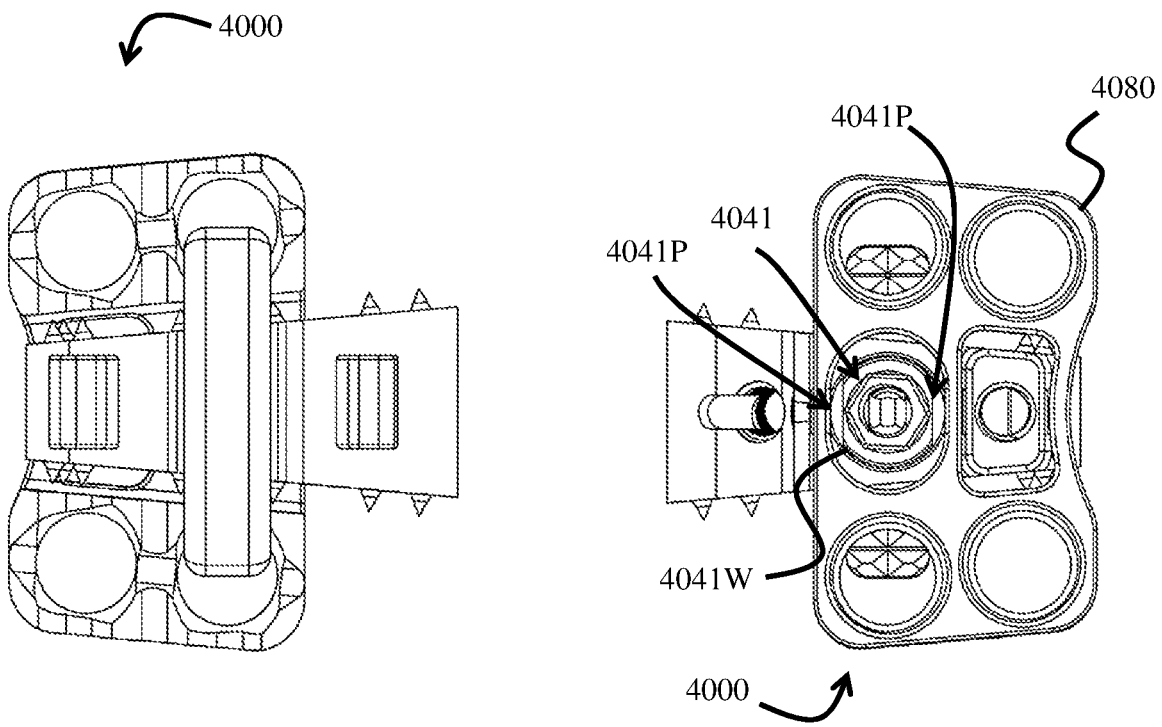
FIG. 40E
FIG. 40F

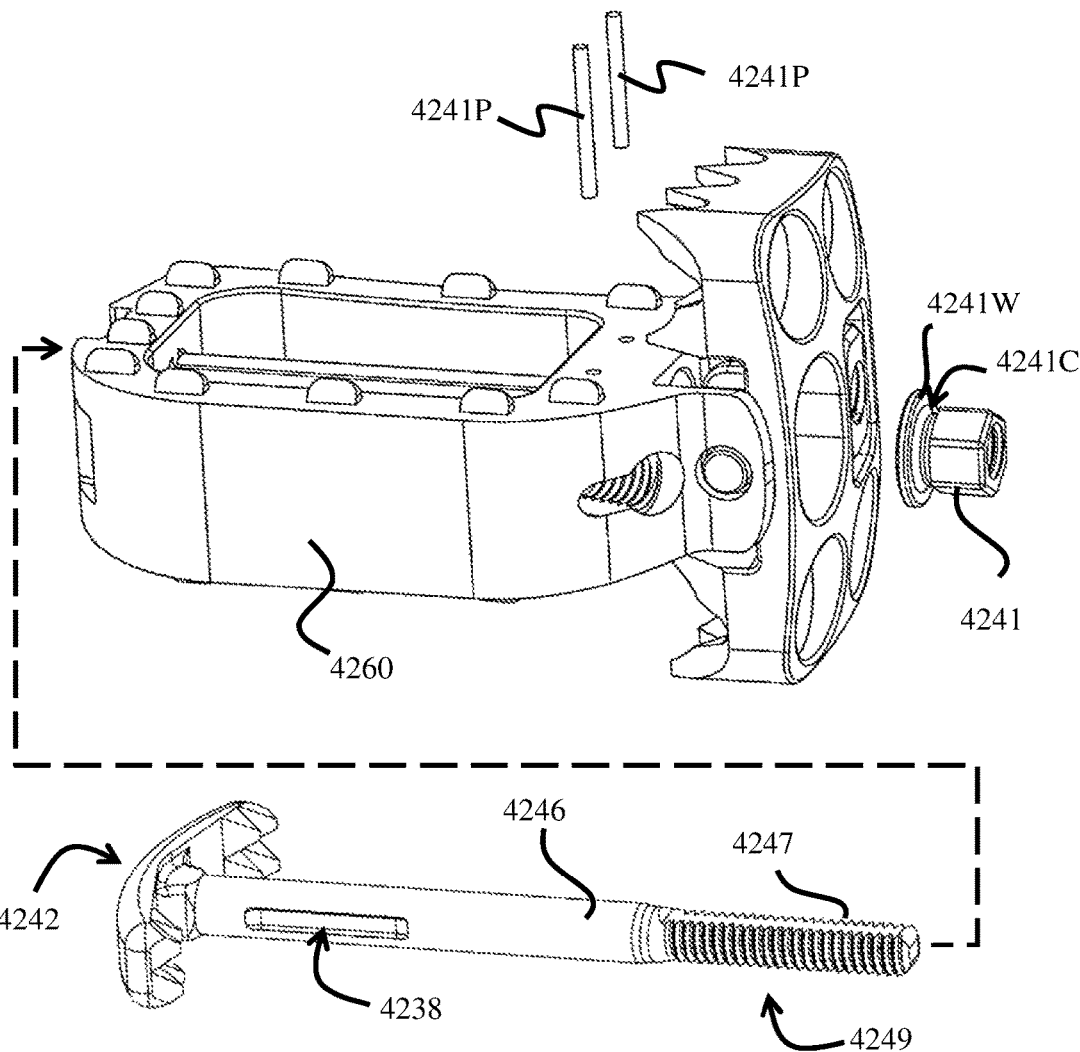
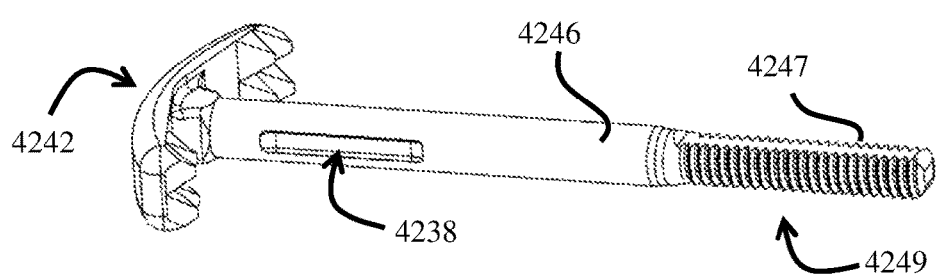
FIG. 42A
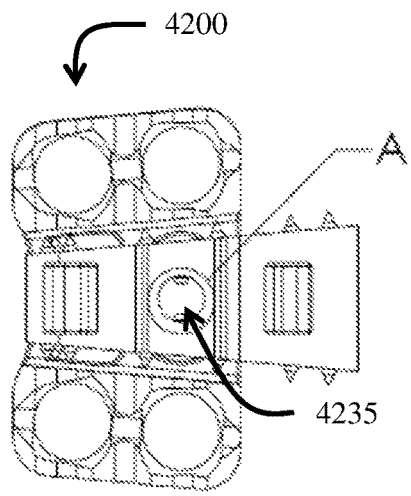
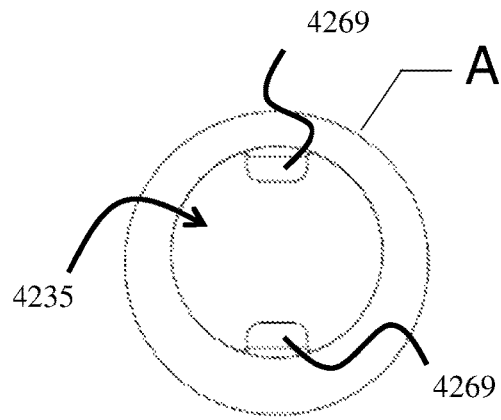
FIG. 42B    FIG. 42C

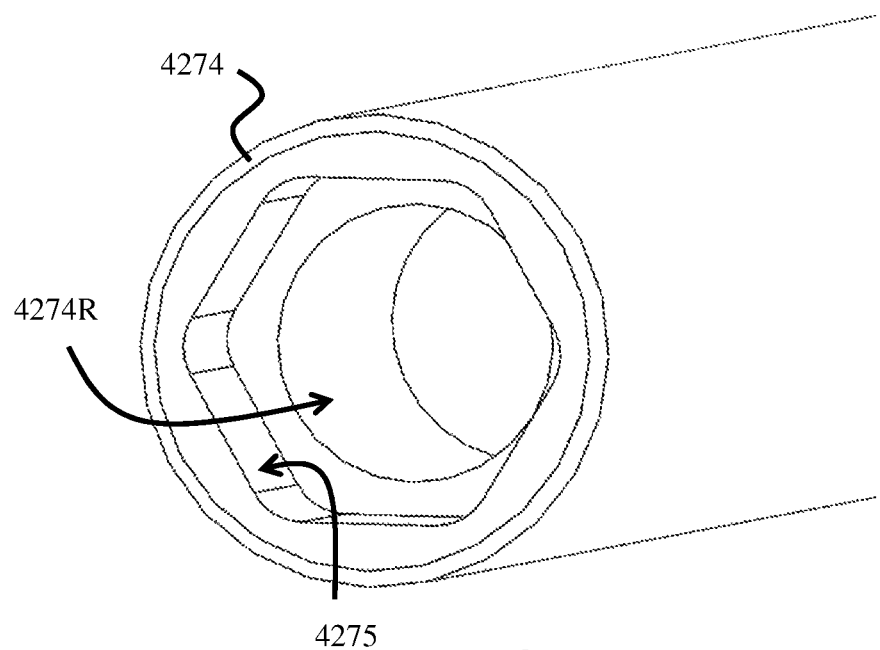
FIG. 42D
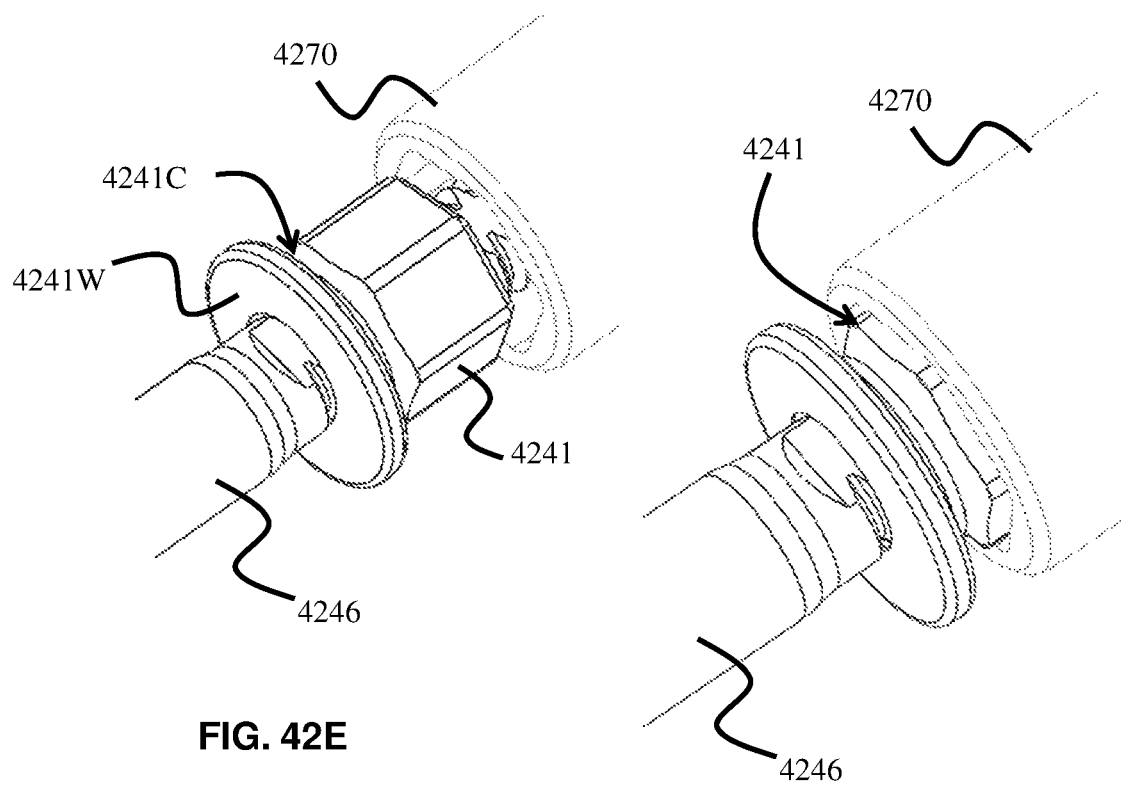
FIG. 42E
FIG. 42F

IMPLANT SYSTEM AND METHODS OF USE

CROSS-REFERENCE TO RELATED APPLICATIONS

This application claims benefit of U.S. Pat. App. No. 63/478,620 filed on Jan. 5, 2023; this application is also a continuation in part application of U.S. patent application Ser. No. 18/051,732 filed on Nov. 1, 2022; this application is also a continuation in part application of U.S. patent application Ser. No. 17/934,874 filed on Sep. 23, 2022; this application also claims benefit of U.S. Pat. App. No. 63/369,330 filed on Jul. 25, 2022; this application also claims benefit of U.S. Pat. App. No. 63/349,136 filed on Jun. 5, 2022; this application is also a continuation in part application of U.S. patent application Ser. No. 17/676,609 filed on Feb. 21, 2022; U.S. patent application Ser. No. 18/051,732 claims benefit of U.S. Pat. App. No. 63/369,330; U.S. patent application Ser. No. 18/051,732 is a continuation in part of U.S. patent application Ser. No. 17/676,609; U.S. patent application Ser. No. 18/051,732 is a continuation in part of PCT Pat. App. No. PCTUS2021/037285 filed on Jun. 14, 2021; U.S. patent application Ser. No. 17/934,874 claims benefit of U.S. Pat. App. No. 63/247,345 filed on Sep. 23, 2021; U.S. patent application Ser. No. 17/676,609 is a continuation application of U.S. patent application Ser. No. 17/347,492, now U.S. Pat. No. 11,259,936 issued on Mar. 1, 2022; U.S. patent application Ser. No. 17/676,609 is a continuation application of PCT App. No. PCTUS2021/037,285; U.S. patent application Ser. No. 17/347,492 claims benefit of U.S. Pat. App. No. 63/039,242 filed on Jun. 15, 2020; PCT Pat. App. No. PCTUS2021/037285 claims benefit of U.S. Pat. App. No. 63/039,242; and the entire contents of which are incorporated herein by reference.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

1. Field of the Invention

This invention relates to orthopedic implants. The implants may be used as spinal implants configured to augment the vertebral body or fuse multiple vertebral bodies to decompress neural elements and alter the alignment of the spine. The implants may also be configured for use within other bones or other joints.

2. Background

In the field of spinal disorders, available literature supports that trauma and degenerative spinal conditions may result in back pain and/or leg pain. These conditions can lead to debilitation, loss of work, independence and life happiness.

Compression fractures account for more than 60 percent of thoracolumbar fractures. The specific types of injuries associated with vertebral compression fractures may include: endplate impaction, wedge impaction fractures, vertebral body collapse, split fractures and coronal split fractures.

Patients with spine issues often start with degenerative disc disease which manifests in collapsing of the disc, which happens due to loss of disc nutrition as aging occurs. This leads to loss of the normal cushioning function provided by the discs between each vertebra. Next, the endplates, which are also affected by the degenerative process, can no longer handle the normally applied stresses, which leads to microfractures in the adjacent vertebral bodies. The chronic factures in a collapsed or fractured vertebral body may then create a cascade of other conditions in the spine, including (but not limited to) degenerative scoliosis, facet joint subluxation and facet joint degeneration, nerve root compression, and further vertebral body collapse.

Studies have also shown that degenerative disc disease and degenerative scoliosis may be associated with significant pain, mental anguish, anxiety, and functional disability as well as diminished self-perception/mental health and decreased function.

Patients with degenerative disc disease associated with degenerative scoliosis, many times, have a collapsing foramen on the concave side of the spine. As this happens the superior facet of the vertebra below slides cephalad and pinches the nerve root in the now narrowed foramen. Currently, there is no good minimal surgical treatment with lasting symptom relief. Common treatments are decompression without fusion, decompression with limited fusion, and decompression with extended (extensive) fusion and reconstruction. Decompression without Fusion Treatments: A collapsing disc and vertebral body, allows the facet from below to come up and encroach into the foramen, causing compression of the nerve root. Some surgeons prefer to take a minimalist approach and try to open the foramen by surgically removing parts of the facet joint and some disc to give the nerve root additional space. While this conservative decompressive procedure without a fusion may be appropriate for selected patients, studies have demonstrated "greater risk of deformity progression, poor outcomes, and higher rates of reoperations" in these cases. It is believed that this is due to failure to address the cause of the narrowed foramen, that being, subluxation of the facet joints secondary to further disc collapse and further microfractures in the vertebral body leading to further wedging.

Decompression with Limited Fusion Treatments: Decompression with limited fusion is applicable for patients whose symptoms are limited to specific and short segments (1-3 levels), but care must be taken in assessing and correcting the sagittal and coronal alignment. Patients with uncorrected misalignment many times have poor outcomes after decompression with limited fusion. Fusions of any kind in the lumbar spine can often start a cascade of events by transferring lumbar spine motion to the unfused segments of the spine above and below the fusion, resulting in more deterioration of the adjacent levels requiring further treatment which is usually additional fusion. This is referred to in the literature as adjacent level disease.

Extended Reconstruction Treatments: Extended reconstruction (>3 levels) of the lumbar spine has been a foundation of correction for adult degenerative scoliosis. However, fusions of this scope also start a cascade of events by transferring the spine motion of the fused to the unfused segments of the spine resulting in the eventual deterioration of the adjacent levels requiring further treatment which is usually additional fusion. Clinical presentation of adjacent segment deterioration, with coronal, sagittal or both deformities above or below the existing fusion causing severe back and/or leg pain often occur, necessitating further treatment and may result in additional levels requiring fusion.

One means of addressing leg pain is to decompress the neural elements. Specifically, the nerves that exit the spinal foramen are particularly venerable to compression as disc height and vertebral wall collapse conspire to narrow the amount of space available to the exiting nerve root. Accordingly, there is a dire need for an implant system and method of use to treat the chronic trauma and fractures resulting in collapsed vertebra and intervertebral disc, and causing back pain and or leg pain that addresses the above shortcomings.

Another means of addressing leg pain is a more traditional decompression and fusion by implanting a device between two vertebral bodies and fusing them together. In this intervertebral procedure, after the neural elements are decompressed, two or more vertebrae may be fused, or joined, together with the implant device to stabilize the spine and permanently stop the movement between bones that is causing pain and ensure appropriate space for exiting nerve roots. The stabilization may also be used to correct alignment of the spine in multiple planes.

For other joints, an implant device similar in design to those disclosed herein, may be used as an arthrodesis implant device in an arthrodesis procedure. In this arthrodesis procedure, adjacent bones of a joint or adjacent bone portions are immobilized by fusing or joining them with an implant device that secures the adjacent bones. The stabilization may also be used to correct alignment of the bones of the joint.

BRIEF SUMMARY OF THE INVENTION

The following summary is included only to introduce some concepts discussed in the Detailed Description below. This summary is not comprehensive and is not intended to delineate the scope of protectable subject matter, which is set forth by the claims presented at the end.

Within this description, the terms far, distal and contralateral are used interchangeably and are intended to be interpreted as defining that one thing is distant from another such as distance from a point of origin, situated away from a point of origin, and pertaining to the other side. Also, the terms near, proximal and ipsilateral are used interchangeably within this description and are intended to be interpreted as defining a short distance away from another such as away from a point of origin, situated toward a point of origin and belonging to or occurring on the same side of a body.

Within this description and the descriptions of the patent applications to which this application claims priority to, the terms anchor frame and vertical member are used interchangeably to refer to the same structural element and are intended to be interpreted as any type of structural element having any position or angle relative to the cage to help secure implant system components to bone and as further described below.

In some of the disclosed embodiments of an implant system having a cage and a staple, the staple is slidable relative to the cage. The slidabilty of the staple relative to the cage provides several features to the implant system. This slidable configuration allows portions of the staple to slide longitudinally in and out, towards and away from the cage. This allows for better control of the alignment, location and positioning of the staple shaft, and when the staple shaft is operably coupled to the staple head in a way that allow the staple head to rotate with the staple shaft, this allows for better control of the alignment and location and positioning of the staple head. This control allows the staple head to be moved through alignments and locations and positions that better accommodate the surface of the bone to better secure the staple and implant device to the bone.

In some of the disclosed embodiments of an implant system having a cage and an anchor frame, the anchor frame is pivotable relative to the cage. The pivotability of the anchor frame relative to the cage provides several features to the implant system. This pivotable coupling allows the anchor frame to move and conform with the surface of the bone and better secure the staple and the implant device to the bone. Because the anchor frame better conforms to the surface of the bone, and because it's pivotably coupled to the cage, the mechanical stresses on the connection between the anchor frame and the cage are reduced and the risk of mechanical failure are reduced.

In some of the disclosed embodiments of an implant system, the implant system is secured to a bone with a compressive force. The ability of the implant system to secure the implant device with a compression force from opposite sidewalls of a bone provides a more secure anchoring of the implant device to the bone as compared to anchoring from one side of the bone. The orientation of the implant device when implanted laterally also provides a lateral platform on the device to anchor additional devices such as tether screws, tulip head screws and rods or tethers or cords to the implant device. The orientation of the implant device when implanted laterally also provides the ability for the implant to be implanted from orientations that take advantage of the surgical benefits of approach orientations such as lateral or oblique.

In one aspect, the present disclosure provides an orthopedic implant device comprising a cage, a staple comprising a staple head and a staple shaft and the staple shaft configured to rotate the staple head from an extended position extended from the cage to a deployed position.

In some embodiments, the orthopedic implant is configured to be implanted across a vertebral body of a vertebrae, a longitudinal axis of the cage is configured to extend laterally across the vertebral body of a vertebrae, and the staple is configured to secure the orthopedic implant to a lateral sidewall of the vertebral body whereby the orthopedic implant device may be implanted from a lateral direction relative to the vertebral body and the staple head is configured to secure the orthopedic implant to a distal lateral sidewall of the vertebral body.

In some embodiments, the orthopedic implant is configured to be implanted across a vertebral body of a vertebrae, a longitudinal axis of the cage is configured to extend laterally across the vertebral body of a vertebrae, and the staple is configured to secure the orthopedic implant to a lateral sidewall of the vertebral body whereby the orthopedic implant device may be implanted from one of an anterior or an oblique direction relative to the vertebral body and the staple head is configured to secure the orthopedic implant to a distal lateral sidewall of the vertebral body.

In some embodiments, the staple shaft is received in a through bore of the cage, and the through bore extends along a longitudinal axis of the cage from a first lateral side of the cage to a second lateral side of the cage.

In some embodiments, the extended position comprises a neutral alignment of the staple head and an extended location of the staple head extended a distance away from the cage, and the deployed position comprises a non-neutral alignment of the staple and an extended location of the staple away from the cage.

In some embodiments, the staple shaft is further configured to move the staple head from an insertion position to the extended position. In some embodiments, the insertion position comprises a neutral alignment of the staple and a non-extended location relative to the cage, and the extended position comprises a neutral alignment of the staple and an extended location of the staple away from the cage.

In some embodiments, the staple shaft is further configured to move the staple head from the deployed position to a stabilization position. In some embodiments, the deployed position comprises a non-neutral alignment of the staple and an extended location of the staple away from the cage, and the stabilization position comprises a non-neutral alignment of the staple and retracted location of the staple retracted towards the cage.

In some embodiments, the staple shaft is received in a through bore of the cage, and the staple shaft is rotatable within the through bore of the cage whereby the staple shaft is configured to move the staple head from the extended position to the deployed position relative to the cage.

In some embodiments, the staple shaft is received in a through bore of the cage, and the staple shaft is longitudinally slidable within the through bore of the cage whereby the staple shaft is configured to slidably move the staple head from an insertion position to the extended position extended away from the cage.

In some embodiments, the staple head comprises one or more staple tine on one end of the staple head and one or more staple tine on an other end of the staple head, and the staple head is a unitary staple head from the one end to the other end.

In some embodiment, the staple shaft is received in a through bore of the cage, and the staple shaft is longitudinally slidable within the through bore of the cage whereby the staple shaft is configured to slidably move the staple head from the deployed position to a stabilization position retracted towards the cage.

In some embodiments, the staple shaft further comprises an engagement portion configured to mate with an engagement tool whereby when the engagement tool is rotated, the staple shaft is rotated and the staple head is moved from the extended position to the deployed position.

In some embodiments, the engagement portion of the staple shaft comprises a proximal portion of the staple shaft with flats.

In some embodiments, the orthopedic implant device further comprises a threaded nut. In some embodiments, the staple shaft has a threaded portion, and the threaded nut is configured to mate with the threaded portion of the staple shaft whereby when the threaded nut is rotated, the threaded nut engages the threaded portion of the staple shaft and the staple head is moved away from the cage. In some embodiments, the staple shaft has a threaded portion, and the threaded nut is configured to mate with the threaded portion of the staple shaft whereby when the threaded nut is rotated, the threaded nut engages the threaded portion of the staple shaft and the staple head is retracted towards the cage. In some embodiments, the staple shaft has a threaded portion and an engagement portion, the engagement portion of the staple shaft is configured to be engaged by a shaft engagement portion of an engagement tool whereby the shaft engagement portion of the engagement tool is configured to rotate the staple shaft and move the staple head from the extended position to the deployed position, the threaded nut configured to be engaged by a nut engagement portion of an engagement tool to rotate the threaded nut, the threaded nut is configured to mate with the threaded portion of the staple shaft whereby when the threaded nut is rotated in a first direction, the threaded nut engages the threaded portion of the staple shaft and the staple head is extended away from the cage, and the threaded nut is configured to mate with the threaded portion of the staple shaft whereby when the threaded nut is rotated in a second direction, the threaded nut engages the threaded portion of the staple shaft and the staple head is retracted towards the cage. In some embodiments, the threaded nut is received in a retaining channel of the cage whereby a longitudinal position of the threaded nut relative to the cage is constrained by the retaining channel.

In some embodiments, the orthopedic implant device of claim 1 further comprising an anchor frame. In some embodiments, the anchor frame is coupled to the cage. In some embodiment, the anchor frame further comprises at least one through hole to accommodate an anchoring element to anchor the anchor frame to a bone. In some embodiments, the anchor frame further comprises at least one anchor frame tooth to secure the anchor frame on a bone. In some embodiment, the anchor frame further comprises at least one through hole configured to receive an anchoring element and couple the anchor frame to a bone.

In some embodiments, the orthopedic implant device further comprises an anchor frame pivotally coupled to the cage. In some embodiments, the anchor frame comprises at least one pivot connection configured to pivotally couple the anchor frame to the cage. In some embodiments, the anchor frame pivots about an axis about ninety degrees to a longitudinal axis of the cage. In some embodiments, the anchor frame comprises at least one pivot connection configured to pivotally couple the anchor frame to the cage, the at least one pivot connection comprises at least one anchor frame pivot element, the cage further comprises at least one cage pivot element, and the anchor frame pivot element is configured to couple with the at least one cage pivot element to pivotally couple the anchor frame to the cage. In some embodiments, the anchor frame pivot element comprises at least one through hole, the at least one cage pivot element comprises at least one protrusion, and the at least one protrusion is configured to be received in the at least one through hole of the anchor frame pivot element to pivotally couple the anchor frame to the cage.

In some embodiments, the cage further comprises at least one cage stop, the staple shaft is coupled to a key, and the at least one cage stop configured to engage the key to influence a movement of the staple head relative to the cage. In some embodiments, the cage stop comprises a radially grooved surface, the staple shaft having an engagement portion configured to mate with an engagement tool whereby when the engagement tool is rotated, the staple shaft is rotated, the key comprising a radially grooved washer having a through hole shaped to be coupled to and mate with the engagement portion of the staple shaft, and the radially grooved washer having a radially grooved surface configured to mesh with the radially grooved surface of the cage whereby when the staple is retracted to a stabilized position, the staple shaft is rotationally locked in a radial position relative to the cage. In some embodiments, the radial position of the staple shaft relative to the cage is one of a finite number of radial positions.

In some embodiments, the orthopedic implant device is configured to alter an endplate surface plane of a vertebral body.

In some embodiments, the orthopedic implant device is configured to alter a distance between a superior endplate surface plane and an inferior endplate surface plane in order to alter a plate height of a vertebral body.

In some embodiments, the orthopedic implant device is configured to alter an angle between a superior endplate surface plane and an inferior endplate surface plane of a vertebral body.

In some embodiment, the orthopedic implant device is configured to alter an angle between an endplate surface plane of one vertebral body and an endplate surface plane of another vertebral body.

In some embodiments, the staple and the cage are configured to secure the cage to adjacent bones of a joint.

In some embodiments, the staple and the cage are configured to secure the cage to adjacent bones portions.

In another aspect, the present disclosure provides an orthopedic implant device comprising a cage, a staple comprising a staple head and a staple shaft, and the staple shaft is longitudinally slidable relative to the cage whereby the staple shaft is configured to slidably move the staple head from an insertion position to an extended position extended away from a distal end of the cage.

In some embodiments, the orthopedic implant device further comprises an anchor frame, and the orthopedic implant device further comprises at least one pivot element configured to pivotally couple the anchor frame to the cage.

In some embodiments, the staple shaft is received in a through bore of the cage, and the through bore extends along a longitudinal axis of the cage from a first lateral side of the cage to a second lateral side of the cage.

In some embodiments, the extended position comprises a neutral alignment of the staple head and an extended location of the staple head extended away from the cage, and the insertion position comprises a neutral alignment of the staple head and a non-extended location of the staple head relative to the cage.

In some embodiments, the staple shaft is further configured to move the staple head from the extended position to a deployed position. In some embodiments, the extended position comprises a neutral alignment of the staple head and an extended location relative to the cage, and the deployed position comprises a non-neutral alignment of the staple head and an extended location of the staple away from the cage. In some embodiments, the staple shaft is further configured to move the staple head from the deployed position to a stabilization position. In some embodiments, the deployed position comprises a non-neutral alignment of the staple head and an extended location of the staple head away from the cage, and the stabilization position comprises a non-neutral alignment of the staple head and retracted location of the staple head towards the cage.

In some embodiments, the staple head is configured to engage a distal lateral side of a vertebral body of a vertebrae to secure the cage to the vertebral body.

In some embodiments, the staple head comprises one or more staple tine on one end of the staple head and one or more staple tine on an other end of the staple head, and the staple head is a unitary staple head from the one end to the other end.

In some embodiments, the staple shaft further comprises an engagement portion configured to mate with an engagement tool whereby when the engagement tool is rotated, the staple shaft is rotated and the staple head is moved from the extended position to a deployed position. In some embodiment, the engagement portion of the staple shaft comprises at least one flat surface on a proximal portion of the staple shaft.

In some embodiments, the orthopedic implant device further comprises a threaded nut, the staple shaft having a threaded portion, and the threaded nut configured to mate with the threaded portion of the staple shaft whereby when the threaded nut is rotated, the threaded nut engages the threaded portion of the staple shaft and the staple head is moved away from the cage.

In some embodiments, the orthopedic implant device further comprises a threaded nut, the staple shaft having a threaded portion, and the threaded nut configured to mate with the threaded portion of the staple shaft whereby when the threaded nut is rotated, the threaded nut engages the threaded portion of the staple shaft and the staple head is retracted towards the cage.

In some embodiments, the orthopedic implant device further comprises a threaded nut, the staple shaft has a threaded portion and an engagement portion, the engagement portion of the staple shaft is configured to be engaged by a shaft engagement portion of an engagement tool whereby the shaft engagement portion of the engagement tool is configured to rotate the staple shaft and move the staple head from the extended position to a deployed position, the threaded nut configured to be engaged by a nut engagement portion of the engagement tool to rotate the threaded nut, the threaded nut is configured to mate with the threaded portion of the staple shaft whereby when the threaded nut is rotated in a first direction, the threaded nut engages the threaded portion of the staple shaft and the staple head is extended away from the cage, and when the threaded nut is rotated in a second direction, the staple head is retracted towards the cage.

In some embodiments, the orthopedic implant device further comprises an anchor frame. In some embodiments, the anchor frame further comprises at least one through hole to accommodate an anchoring element to anchor the anchor frame to a bone. In some embodiments, the anchor frame further comprises at least one anchor frame tooth to secure the anchor frame on a bone.

In some embodiments, the orthopedic implant device further comprises an anchor frame, and at least one pivot element configured to pivotally couple the anchor frame to the cage. In some embodiments, the anchor frame pivots about an axis about 90 degrees to a longitudinal axis of the cage. In some embodiments, the anchor frame pivots about an axis having a range of about 45 degrees to 90 degrees to a longitudinal axis of the cage. In some embodiments, the at least one pivot element comprises at least one anchor frame pivot element, at least one cage pivot element, and the anchor frame pivot element is configured to couple with the at least one cage pivot element to pivotally couple the anchor frame to the cage. In some embodiments, the at least one anchor frame pivot element comprises at least one protrusion, the at least one cage pivot element comprises at least one recess; and the at least one protrusion is configured to be received in the at least one recess to pivotally couple the anchor frame to the cage. In some embodiments, the at least one anchor frame pivot element comprises at least one through hole, the at least one cage pivot element comprises at least one protrusion, and the at least one protrusion is configured to be received in the at least one through hole to pivotally couple the anchor frame to the cage.

In some embodiments, the cage further comprises a cage stop, the staple shaft is coupled to a key, and the cage stop is configured to engage the key to influence a rotational movement of the staple head relative to the cage.

In some embodiments, the cage further comprises a cage stop comprising a radially grooved surface, the staple shaft is coupled to a key, the key comprising a radially grooved washer having a recess shaped to be coupled to and mate with an engagement portion of the staple shaft, and whereby when an engagement tool is rotated, the staple shaft is rotated and the radially grooved surface of the cage meshes with the radially grooved surface on the radially grooved washer to urge the engagement tool and the staple shaft to lock at predetermined rotational angles.

In some embodiments, the orthopedic implant device is configured to alter an endplate surface plane of a vertebral body.

In some embodiments, the orthopedic implant device is configured to alter a distance between a superior endplate surface plane and an inferior endplate surface plane in order to alter a plate height of a vertebral body.

In some embodiments, the orthopedic implant device is configured to alter an angle between a superior endplate surface plane and an inferior endplate surface plane of a vertebral body.

In some embodiments, the orthopedic implant device is configured to alter an angle between an endplate surface plane of one vertebral body and an endplate surface plane of another vertebral body.

In some embodiments, the staple and the cage are configured to secure the cage to adjacent bones of a joint.

In some embodiments, the staple and the cage are configured to secure the cage to adjacent bone portions.

In some embodiments, the staple shaft is received in a through bore of the cage, the through bore extends from a first lateral side of the cage to a second lateral side of the cage, the staple shaft is rotatable within the through bore of the cage whereby the staple shaft is configured to move the staple head from the extended position to a deployed position relative to the cage, the staple shaft is longitudinally slidable within the through bore of the cage whereby the staple shaft is configured to slidably move the staple head from the insertion position to the extended position extended away from the cage, the staple shaft is longitudinally slidable within the through bore of the cage whereby the staple shaft is configured to slidably move the staple head from the deployed position to a stabilization position retracted towards the cage, the staple shaft further comprises an engagement portion configured to mate with an engagement tool whereby when the engagement tool is rotated, the staple shaft is rotated and the staple head is moved from the extended position to the deployed position, the orthopedic implant device further comprises a threaded nut configured to mate with a threaded portion of the staple shaft whereby when the threaded nut is rotated, the threaded nut engages the threaded portion of the staple shaft and the staple head is extended away from the cage, the orthopedic implant device further comprising an anchor frame, and the orthopedic implant device further comprises at least one pivot connection configured to pivotally couple the anchor frame to the cage.

In some embodiments, the orthopedic implant device is configured to be implanted across a vertebral body of a vertebrae, a longitudinal axis of the cage is configured to extend laterally across the vertebral body of a vertebrae, and the staple is configured to secure the orthopedic implant device to a lateral sidewall of the vertebral body whereby the orthopedic implant device may be implanted from an anterior or a lateral direction relative to a proximal lateral sidewall of a vertebral body and the staple head is configured to secure the orthopedic implant device to a distal lateral sidewall of the vertebral body.

In another aspect, the present disclosure provides an orthopedic implant device comprising a cage, an anchor frame, the anchor frame comprises at least one anchor frame pivot element configured to pivotally couple the anchor frame to the cage, and the anchor frame further comprising at least one through hole to receive an anchoring element to secure the anchor frame and the cage to a bone.

In some embodiments, the bone comprises a vertebral body of a vertebrae, and the anchoring element is configured to secure the anchor frame and the cage to a sidewall of the vertebral body.

In some embodiments, the bone comprises a vertebral body of a vertebrae, and the anchoring element is configured to secure the anchor frame and the cage to the bone whereby the cage contacts a surface of the vertebral body.

In some embodiments, the anchor frame is configured with a non-symmetrical dimension about a longitudinal centerline of the cage.

In some embodiments, the anchor frame is configured with a symmetrical dimension about a longitudinal centerline of the cage.

In some embodiments, the anchor frame further comprises at least one anchor frame tooth to secure the anchor frame on the bone.

In some embodiments, the cage further comprises at least one cage pivot element, and the anchor frame pivot element is configured to couple with the at least one cage pivot element to pivotally couple the anchor frame to the cage.

In some embodiments, the orthopedic implant device further comprises a securing element configured to secure the cage and the anchor frame to the bone. In some embodiments, the securing element comprises a staple. In some embodiments, the securing element comprises a staple, the bone comprises a vertebral body of a vertebrae, the staple is slidably coupled to the cage and configured to engage a distal lateral sidewall of the vertebral body, and the anchoring element is configured to engage a proximal lateral sidewall of the vertebral body whereby the anchor frame and the staple secure the cage to the vertebral body. In some embodiments, the securing element comprises a staple, the staple comprises a staple head and a staple shaft, and the staple shaft configured to move the staple head from a first position to a second position. In some embodiments, the first position is an extended position, and the second position is a deployed position. In some embodiments, the first position is an insertion position, and the second position is an extended position. In some embodiments, the first position is a deployed position, and the second position is a stabilization position. In some embodiments, the second position comprises a stabilization position. In some embodiments, the second position comprises a deployed position. In some embodiments, the staple shaft is received in a through bore of the cage, and the staple shaft is rotatable within the through bore of the cage whereby the staple shaft is configured to move the staple head from the first position to the second position. In some embodiments, the staple shaft is longitudinally slidable within the through bore of the cage whereby the staple shaft is configured to slidably move the staple head from the first position to the second position. In some embodiments, the staple shaft is configured to retract the staple head relative to the cage. In some embodiments, the cage further comprising a cage stop, the staple shaft having a key, and the cage stop configured to engage the key to limit a rotational movement of the staple head relative to the cage. In some embodiment, the through bore extends from a first lateral side of the cage to a second lateral side of the cage. In some embodiments, the staple shaft comprises an engagement portion configured to mate with an engagement tool whereby when the engagement tool is rotated, the staple shaft is rotated and the staple head is moved from the first position to the second position. In some embodiments, the engagement portion of the staple shaft comprises at least one flat surface on a proximal portion of the staple shaft. In some embodiments, the orthopedic implant device further comprises a threaded nut, the staple shaft having a threaded portion, and the threaded nut configured to mate with the threaded portion of the staple shaft whereby when the threaded nut is rotated, the threaded nut engages the threaded portion of the staple shaft and the staple head is moved away from the cage. In some embodiments, the orthopedic implant device further comprises a threaded nut, the staple shaft having a threaded portion, and the threaded nut is configured to mate with the threaded portion of the staple shaft whereby when the threaded nut is rotated, the threaded nut engages the threaded portion of the staple shaft and the staple head is retracted towards the cage.

In another aspect, the present disclosure provides an orthopedic implant device comprising a cage, an anchor frame, a staple, the anchor frame, the staple and the cage operably coupled, whereby the anchor frame and the staple are configured to be secured to opposite lateral sidewalls of a vertebral body, and whereby the cage is secured to extend laterally across the vertebral body.

In some embodiments, the staple comprises a staple head and a staple shaft, the orthopedic implant device further comprises a coupling element, and the coupling element configured to engage the staple shaft and operably couple the staple to the cage whereby the coupling element adjusts the positional relationship of the staple head and the anchor frame whereby the staple head and the anchor frame are secured to the opposite lateral sidewalls of the vertebral body by a compression force.

In some embodiments, the staple comprises a staple head and a staple shaft, the cage comprises a through bore extending longitudinally through the cage, the staple shaft received in the through bore to operably couple the cage and the staple, and the anchor frame operably coupled to the cage whereby the anchor frame, the staple and the cage are operably coupled. In some embodiments, the coupling element comprises a threaded nut configured to engage a threaded portion of the staple shaft whereby the coupling element adjusts the positional relationship of the staple head and the anchor frame.

In another aspect, the present disclosure provides a method to secure a first bone portion to a second bone portion, the method comprising, providing an orthopedic implant device comprising a cage, a staple and an anchor frame, the cage coupled to the anchor frame and the staple, inserting the cage and the staple into an opening between the first bone portion and the second bone portion, and securing the anchor frame to the first bone and the second bone by retracting the staple towards the cage and/or anchor frame. In some embodiments, the method further comprises positioning the staple in a stabilized position to secure the staple to the first bone and the second bone whereby the staple further secures the cage to the first and the second bone portions.

In another aspect, the present disclosure provides a method to secure an orthopedic implant device to a vertebral body, the method comprising, providing an orthopedic implant device comprising a cage and a staple, performing an osteotomy procedure through a vertebral body, inserting the cage and the staple into an opening created by the osteotomy procedure, and positioning the staple whereby one or more staple tines secure the cage and the staple to the vertebral body. In some embodiments, the step of positioning the staple comprises moving the staple from a first to a second position. In some embodiments, the first position is a deployed position, and the second position is a stabilized position. In some embodiments, the step of positioning the staple comprises extending the staple from a position relative to the cage to an extended position, rotating the staple relative to the cage to a deployed position, and retracting the staple relative to the cage to a stabilized position whereby one or more staple tines secure the cage and the staple to the vertebral body. In some embodiment, the orthopedic implant device further comprises an anchor frame coupled to the cage and the method further comprises anchoring the anchor frame to the vertebral body by implanting one or more anchoring element through the anchor frame and into the vertebral body. In some embodiments, the orthopedic implant device further comprises an anchor frame coupled to the cage and the method further comprises anchoring the anchor frame to the vertebral body by retracting the staple towards the anchor frame.

Intravertebral Applications

Intravertebral use of the disclosed implant system is intended to restore foraminal height and treat vertebral body wedging, which result from microfractures and collapse of the vertebral body endplates. These microfractures occur because the collapsed disc creates abnormal stress areas in the vertebral body. The resultant vertebral body wedging, secondary to the microfractures, creates both sagittal and coronal deformity, causing back pain thru misaligned facet joints and leg pain due to foraminal stenosis. The source of the back pain can be confirmed by injecting diagnostic local anesthetic agents around the painful facet joint. Correction of these deformities in the vertebral body via osteotomy and placement of the vertebral implant will reduce the back and leg pain by realigning the facet joints and opening the foramen in this select group of patients. This is analogous to the use of high tibial osteotomies for treatment of knee arthritis. The implant design allows for careful and patient-specific sagittal and coronal alignment correction to prevent the clinical outcomes of misalignment.

This osteotomy procedure and implant device can relieve pain symptoms while maintaining lumbar spine mobility and prevent or delay adjacent level disease. The implant device does not have any motion itself but reestablished proper spinal alignment while preserving the intervertebral disc above and below the operated level.

With the disclosed implant system, a vertebral body osteotomy stabilized with the implant device can correct the wedged segment of the spine through the vertebral body. This opens the foramen and relieves the pinched nerve and therefore relieves the patient's radiculopathy symptoms. The implant design allows for careful and patient-specific sagittal and coronal correction to prevent the clinical outcomes of spinal misalignment.

This technology will bridge the gap between a minimally invasive decompression without fusion and more extensive decompressions requiring a fusion procedure and lead to an improved quality of life when compared to current standard surgical techniques and technology. The patient will have relief from back and/or leg pain without a loss of spine mobility, which can significantly reduce or eliminate the risk of adjacent level accelerated degeneration in the other levels of the spine. The custom alignment created with the implant device can prevent the clinical outcomes of spinal misalignment.

Examples of the implant system may comprise a vertebral implant device configured to alter a distance between a superior endplate surface plane and an inferior endplate surface plane of a vertebral body.

Intervertebral Applications

Intervertebral use of the disclosed implant system is intended to fuse opposing vertebral bodies to eliminate painful motion and/or to restore anatomic alignment, height and stability to the spine following a spinal decompression. This fusion eliminates motion between vertebrae and also prevents the irritation and stretching of nerves and surrounding ligaments and muscles.

Intervertebral use of the implant system generally provides an implant that is able to be secured to the inferior and superior endplates of two opposing vertebrae to facilitate a fusion. Dimensions of components of the implant system may also be shaped to provide patient-specific sagittal and coronal alignment to prevent the clinical outcomes of misalignment.

In some examples, the implant system comprises an intervertebral implant device configured to join one vertebral body to another vertebral body.

Applications with Other Joints

Implant devices similar in design to the above implant systems may be used as an arthrodesis implant device in an arthrodesis procedure for other joints. As done for the joining of two vertebrae, an implant device may be provided that is configured to be secured to opposing sides of adjoining bones in a joint to fuse those bones. The stabilization may also be used to correct alignment of the bones of the joint.

In some examples of the implant system, the implant system comprises an arthrodesis implant device configured to join one bone to another bone.

Other objects, features, and advantages of the systems and techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3A shows an example of an inner staple and FIG. 3B shows an example of a distal staple;

FIG. 3C shows a perspective view showing the distal end, FIG. 3D shows a perspective view from the proximal end and FIG. 3E shows a perspective view from the proximal end and a key;

FIGS. 5A-5D illustrate an example of an anchor frame and related components where FIG. 5A shows an example of an anchor frame, FIG. 5B shows an example of cage screws, FIG. 5C shows an example of bone screws and FIG. 5D shows an example of a bone screw anti-backout component;

FIG. 6A shows the anchor frame separated from the cage and FIG. 6B shows the anchor frame coupled to the cage;

FIG. 9A shows an example with multiple distal staples, FIG. 9B shows an example with a single staple and FIG. 9C shows an example with a single staple;

FIG. 10A shows a vertebral body with an osteotomy, FIG. 10B shows an example of an implant device positioned in the osteotomy, FIG. 10C shows a different view of the implanted device, FIG. 10D shows the anchor frame to be positioned proximal to the cage, FIG. 10E shows the anchor frame positioned proximal to the cage, FIG. 10F shows the anchor frame positioned to receive the cage screws, FIG. 10G shows the implant device with the anchor frame coupled to the cage with the cage screws; FIG. 10H shows the anchor frame anchored to the vertebral body with anchoring elements and FIG. 10I shows the anchoring elements secured with an anti-backout component;

FIG. 11A shows a perspective view and FIG. 11B shows a side view;

FIG. 12A shows an example for use with an implant device in an intervertebral application and FIG. 12B shows an example for use with an implant device in an intravertebral application;

FIG. 13A shows the insertion handle assembly alone, FIG. 13B shows the threaded locking rod received in the insertion handle assembly and FIG. 13C shows a partially exploded view of the insertion handle assembly and the threaded locking rod;

FIG. 16A shows the insertion handle assembly partially inserted and FIG. 16B shows the insertion handle assembly fully inserted;

FIG. 18A shows the engagement of the staple drive handle with the staple shaft and nut and FIG. 18B shows the distal end of the staple drive handle assembly;

FIG. 19A shows a top perspective view and FIG. 19B shows a perspective view from the proximal end;

FIG. 21A shows the paddle in an insertion alignment and FIG. 21B shows the paddle in a deployed alignment;

FIGS. 24A-24E show different views of an example of a far-side elevator tool where FIG. 24A shows a paddle handle in an insertion alignment, FIG. 24B shows the paddle handle in an extended position, FIG. 24C shows the paddle handle rotating and FIGS. 24D and 24E show the measuring portion exposed;

FIG. 35A shows a perspective view of the implant system, FIG. 35B shows a side view with anchoring elements, FIG. 35C shows an exploded perspective view of the implant system, FIG. 35D shows an exploded perspective view of an example of an implant system, FIG. 35E shows a detailed view of a called-out portion from FIG. 35D detailing a nut and a washer, FIG. 35F shows an exploded perspective view of an example of an implant system, and FIG. 35G shows a detailed view of a called-out portion from FIG. 35F detailing the cage retaining channel;

FIGS. 36A and 36 B show exploded perspective views of an example implant system where FIG. 36A shows a view from a proximal end and FIG. 36B shows a view from the distal end;

FIG. 37A shows the implant system from a proximal end view and FIG. 37B shows an example implant system from a side view;

FIGS. 40A-40F show different views of an example implant system with the staple in a deployed position where FIG. 40A is a top perspective view, FIG. 40B is a side perspective view, FIG. 40C is a top view, FIG. 40D is a side view, FIG. 40E is a distal end view and FIG. 40F is a proximal end view;

FIG. 41B shows a side perspective view, FIG. 41C shows a top view, FIG. 41D shows a side view, FIG. 41E shows a distal end view and FIG. 41F shows a proximal end view;

FIGS. 42A-42I show different views of an example implant system components where FIG. 42A shows a partially exploded view of the implant system components, FIG. 42B shows a distal end of the exploded cage and anchor frame, FIG. 42C shows details of the staple sleeve, FIG. 42D shows details of the distal end of the outer rod of the engagement tool, FIGS. 42E and 42F show the engagement of the outer rod with a nut, FIG. 42G shows details of the distal end of the inner rod of the engagement tool, and FIGS. 42H and 42I show the engagement of the inner rod with the staple shaft;

DETAILED DESCRIPTION OF THE INVENTION

Figure 1A:
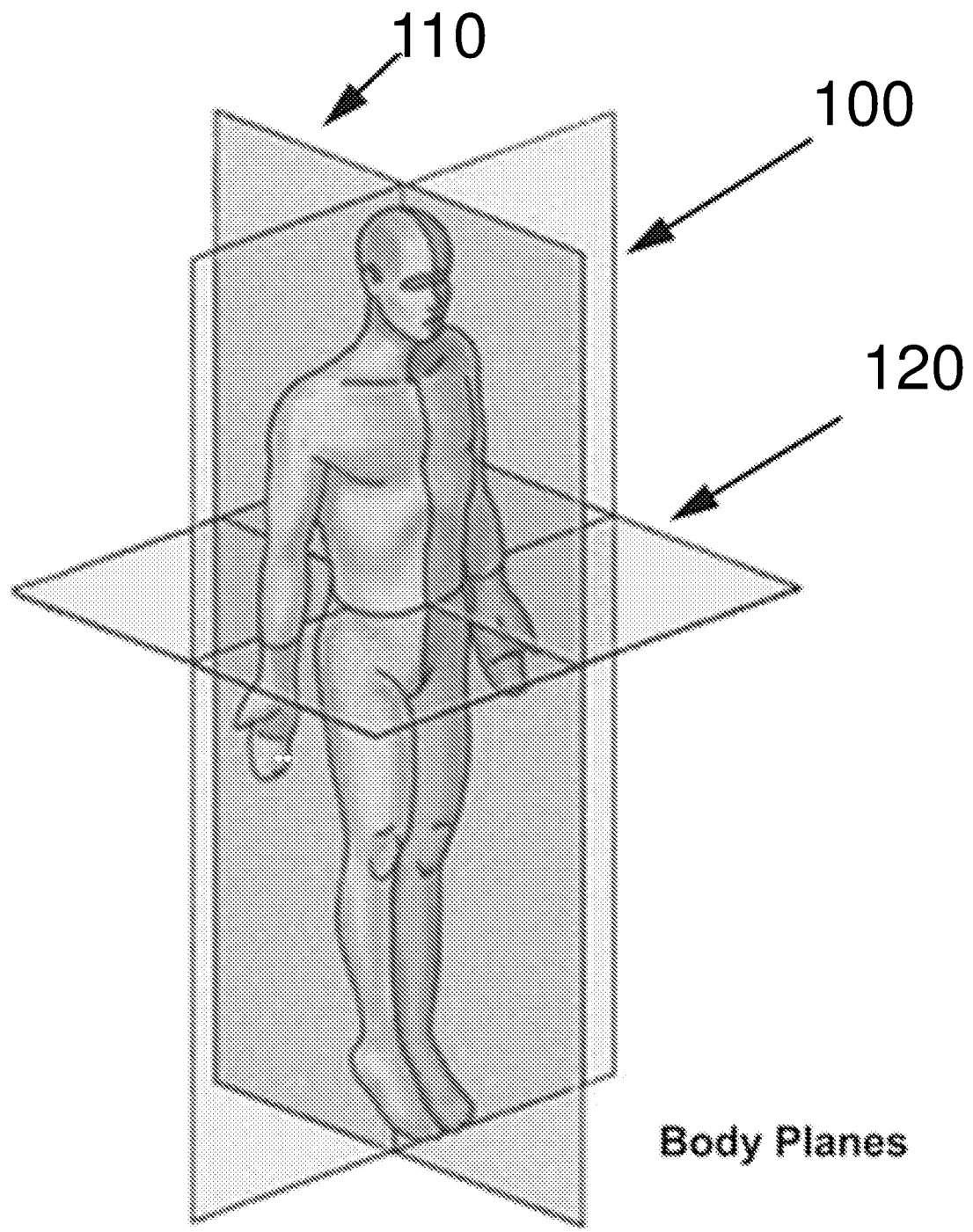
FIG. 1A shows the sagittal, coronal and transverse planes of the human body.

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies to any software and data as described below and in the drawings hereto: Copyright © 2020-2023, NOFUSCO Corporation, All Rights Reserved.

Implant systems and methods of use will now be described in detail with reference to the accompanying drawings. Notwithstanding the specific examples set forth below, all such variations and modifications that would be envisioned by one of ordinary skill in the art are intended to fall within the scope of this disclosure. The implant systems and methods may be used as orthopedic implant systems such as, but not limited to, an intravertebral implant system for use in intravertebral applications, an intervertebral implant system for use in intervertebral applications and an implant system for arthrodesis procedures for other joints throughout the body. The implant systems and methods may comprise an orthopedic implant device such as, but not limited to, an intravertebral implant device, an intervertebral implant device or an implant device for arthrodesis procedures for other joints throughout the body.

Foraminal narrowing is a specific type of spinal stenosis, a spinal condition that occurs when the open spaces between the vertebra (the foramina) narrow. The foramina are bony passageways located between the vertebrae on either side of the spine. Their primary purpose is to provide an exit path for nerves leaving the spinal cord and traveling to other parts of the body.

Minimally invasive spine (MIS) surgery without fusion is generally intended to relieve pressure being applied to the spinal nerves—often a result of conditions such as spinal instability, bone spurs, herniated discs, scoliosis or spinal tumors. In cases where extensive decompressions are required to accomplish the goal of relieving pain, a fusion may become necessary.

Fusion of opposing bones of a joint results in a permanent connection of the bones of the joint to eliminate motion between them. All fusions, including spinal fusion, involves techniques designed to mimic the normal healing process of broken bones where an implant device may be used to hold the vertebrae together, so they can heal into one solid and immobile unit.

Embodiments of the disclosed implant systems may be configured to correct vertebral body deformity in the coronal, sagittal, and axial plane (if needed).

The system may be suitable for indirect foraminal decompressions that require more than a MIS procedure but less than a large decompression and fusion. Embodiments of the disclosed implant systems may be used for 1 and 2 vertebral body interventions.

Embodiments of the disclosed implant systems for use with vertebral applications may be configured to be applied with either an anterior-to-psoas (ATP) or a direct lateral (trans-psoas) approach to the lumbar spine from the concave side of the vertebrae. The ATP approach benefits from the advantages of both anterior and lateral approaches with similar complication rates.

Embodiments of the disclosed implant systems may also be configured to be applied using both ATP and direct lateral approaches from the concave or convex side of a spine with a deformity.

Embodiments of the disclosed implant systems may also be used in a contralateral approach where the far/distal/contralateral side of the vertebral body or bodies, in relation to a point of origin being the approaching side of the procedure, need more correction/separation than the near/proximal/ipsilateral side.

In some embodiments, the implant device generally acts as an opening wedge osteotomy spacer and uses the shape of implant components, such as cage surface planes, to alter the alignment of the vertebral body of a mammalian body.

Although embodiments of the implant device may be positioned from different planes relative to the vertebral body, some embodiments are specifically configured to be inserted and secured from a lateral or an oblique approach angle. These approach angles are particularly beneficial because they are well known to those skilled in the art and reduce the risk of complications from more traditional anterior approach procedures. Insertion from lateral and oblique angles makes it easier to avoid blood vessels, the peritoneal cavity and abdominal muscles during the insertion procedure. This lowers the risk of injury to these vital structures (vessels, nerves & organs) and also minimizes or reduces the need for other surgical specialists, such as vascular surgeons or general surgeons, which may otherwise be required to assist in the procedure.

The ATP approach, as one particular oblique approach, may be used to access the vertebral body and implant the device. With this ATP approach, surgical access is provided to the vertebral body which can sometimes alleviate the need for an additional vascular or general surgeon. With this approach, an oblique incision is made on the patient and abdominal muscles and the retroperitoneal space are bluntly dissected to expose the psoas muscle. The psoas muscle or psoas tendon is retracted posteriorly only as required during certain portions of the procedure to define the surgical corridor and expose the spine and vertebral body for the surgery. Use to the ATP approach provides the opportunity to minimize psoas retraction.

Referring to FIG. 1A showing the sagittal 110, coronal 100 and transverse 120 planes of the human body, embodiments may be used to correct alignment of the spine in the sagittal (110) and coronal (100) planes.

Figure 1B:
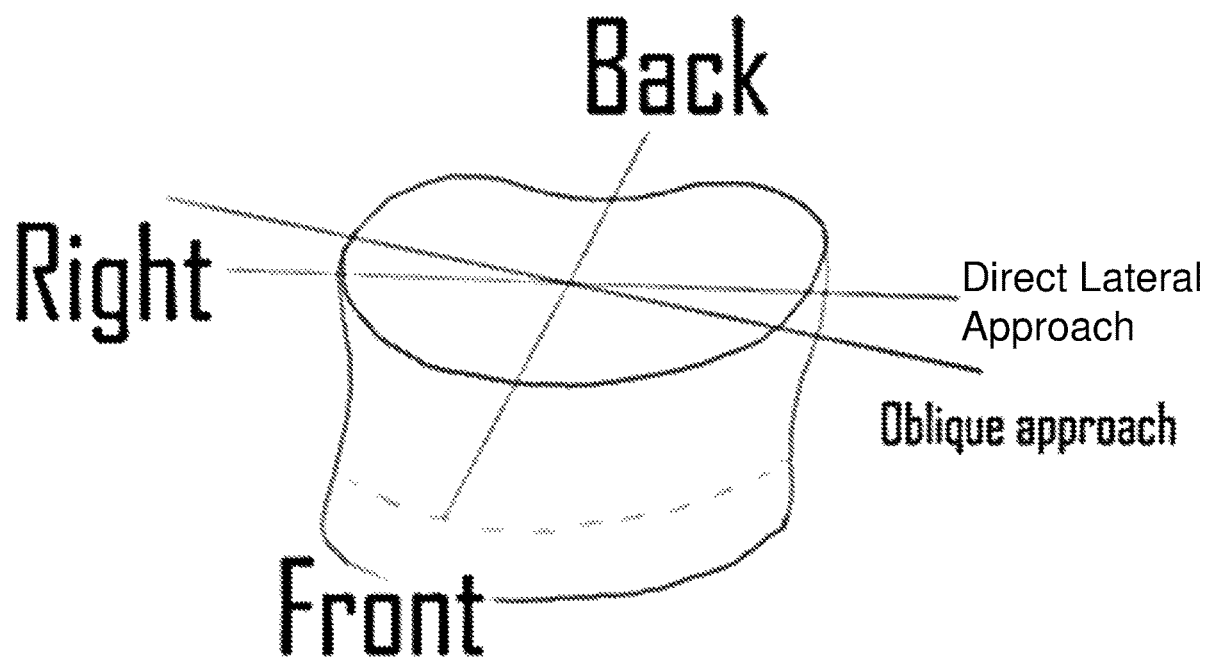
FIG. 1B illustrates the different axis and placement approaches used with an example of an implant systems.

Referring to FIG. 1B, the implant system may be inserted and positioned at and from different angles relative to the vertebral body. The placement and configuration of the implant components dictate the different alignment surface angles of the vertebral bodies. For example, some embodiments of the implant system may be implanted through anterior (front), oblique or lateral (left/right) approaches.

Figure 1C:
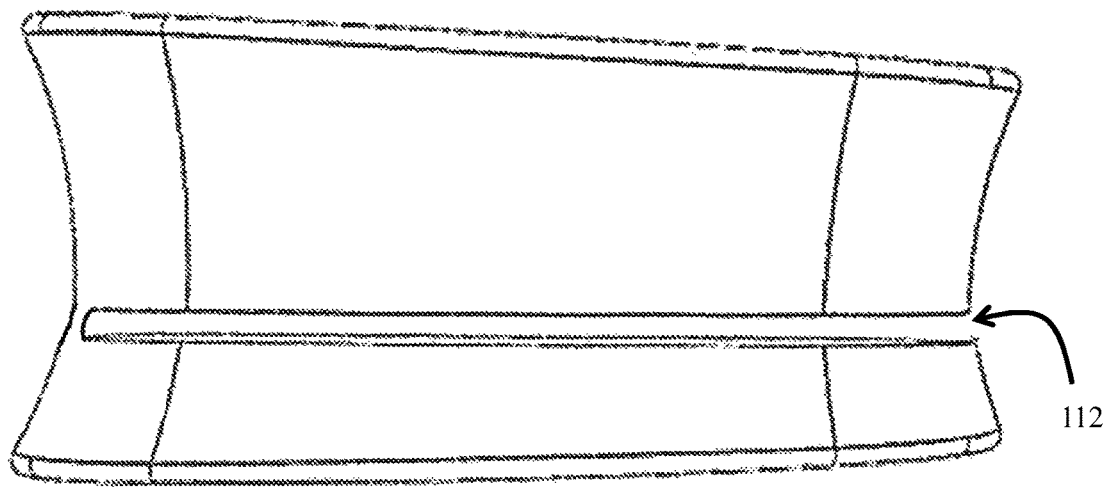
FIG. 1C illustrates an example osteotomy of the vertebral body when viewed in the coronal plane.

Examples of the implant system configured for vertebral intrabody applications are generally used in conjunction with an osteotomy made through the vertebral body inferior to the pedicle as shown in FIG. 1C. As shown, the osteotomy 112 is cut inferior to the inferior aspect of the pedicle and level with the vertebral body's inferior endplate.

In some embodiments, the implant system is configured to preserve the spinal vascular system.

In some embodiments, the configuration of the implant system allows for stabilization and bone fusion within the vertebral body after placement.

In some embodiments, the implant system is configurable. For example, the implant system may be configured to provide different alignments to vertebral bodies and the spine. For example, the implant system may provide configurable dimensions such as different height and angles of the cage surfaces to provide different cage surface planes and different sagittal and coronal angular correction when positioned in the vertebral body.

In some embodiments, the implant system may be a modular system including a self-stabilizing cage which includes deployable and fixed securing elements, an anchor frame fixable to the cage, anchoring elements such as bone fixation screws attachable to the anchor frame and any one of many anti-backout features known in the art to prevent the bone fixation screws from projecting out of the anchor frame.

In some embodiments, the implant system may be pre-packed with bone graft (autogenous, allogenic or synthetic) and the implant system may be configured to allow additional graft material to be post-packed, injected or otherwise placed after positioning of the implant within the vertebral body.

In some embodiments, provisions may be made to couple the implant system to other constructs such as rod/cord-screw systems, flexible tethers and plate systems.

In some embodiments, the implant system generally comprises a cage with a staple and an anchor frame. The staple and the anchor frame may be on opposing sides of the cage to secure the cage to bone. In some embodiments the staple may have features that allow the staple to inserted, extended, deployed and stabilized or secured to the bone. In some embodiments the anchor frame is pivotally coupled to the cage.

In some embodiments, the staple of the implant system may have extension, deployment and retracting features that allow the staple to be moved through multiple positions to secure the implant device to the bone. The movement features may allow the distal staple to be easily moved between an insertion position, an extended position, a deployed position and a stabilized position. These different positions of the staple describe both the rotational alignment of the staple head and the location of the staple head relative to other elements of the implant device.

Insertion position: In the insertion position, alignment of the length of the staple head is in a neutral alignment, generally the orientation of the length of the staple head being coplanar or parallel to a plane extending along the transverse axis of the cage. In this position, the longitudinal location of the staple head relative to the longitudinal axis of the cage is the location as the implant device is being positioned for implanting. In some embodiments, the longitudinal location of the staple head is generally positioned in a non-extended/insertion location close to the distal end of the cage. In some embodiments, the insertion location of the staple head position may have the staple head in an extended location extended away from the cage. In some embodiments, portions of the staple head may be received in a protective recess on the cage.

Extended position: In the extended position, the alignment of the staple head is in the neutral alignment, generally parallel to the transverse axis of the cage. In this position, the longitudinal location of the staple head relative to the cage longitudinal axis is in an extended location extended away from the cage. The extended position generally extends the location of the distal staple head from the cage longitudinally so that the staple head and the staple tines extend beyond the sidewalls of the bone.

Deployed position: In the deployed position, the staple head is rotated to a non-neutral alignment that is other than parallel to the transverse axis of the cage. In this position, the non-neutral alignment of the staple head may be at any angle relative to the insertion and extended position sufficient to allow the staple tines of the staple to be positioned to engage the sidewalls of the bone. The longitudinal location of the staple head relative to the longitudinal axis of the cage is in an extended location extended away from the cage sufficient to allow the staple tines of the staple head to extend beyond the bone. Preferably, the non-neutral alignment in the deployed position is about 90 degrees from the neutral alignment to maximize engagement with the bone.

Stabilized position: In the stabilized position, alignment of the length of the staple head is not parallel to the transverse axis of the cage and sufficient to allow the staple tines of the staple to engage the walls of the bone. In this position, the alignment of the staple head is generally in the non-neutral alignment in the deployed position. In this position, the longitudinal location of the staple head relative to the cage is in a retracted location retracted towards the cage sufficient to allow the staple tines of the staple head to engage or embed themselves in the bone to mechanically engage and stabilize the staple head and the cage to the bone. In this position, the anchor frame provides a counter force for the staple head to be retracted against.

To support the above positions, the staple may comprise the staple head and a staple shaft. The staple shaft may be configured to move and rotate the staple head through the above positions. For example, the staple shaft may be rigidly coupled to the staple head and configured to move the staple head from an extended position to a deployed position by a rotation of the shaft and the staple head. As another example, the staple shaft may be configured to move the staple head from an insertion position to an extended position by slidably moving the staple shaft through a bore of the cage and extending the staple head away from the cage. The staple shaft may also be configured to move the staple head from a deployed position to a stabilization position by slidably moving the staple shaft through a bore of the cage and retracting the staple shaft and staple head towards the cage.

To support the movement of the staple head through the different longitudinal locations of the above positions, the staple shaft may also be configured to move the staple head from an insertion to an extended longitudinal location by having a threaded staple shaft mate with a threaded coupling element such as a nut and rotating the coupling element to extend the staple head away from the cage. The nut may be partially constrained in the cage so that its longitudinal position is held relatively unchanged or within a small longitudinal range when the staple head is extended and retracted. The staple shaft may also be configured to move the staple head from the deployed to a stabilization longitudinal location by having a threaded shaft mate with a threaded coupling element and rotating the coupling element to retract the staple head towards the cage.

To support the movement of the staple head through the different alignments of the above positions, the staple shaft may also have an engagement portion configured to be engaged by a tool to rotate the staple shaft and staple head from the extended alignment to the deployed alignment. To maintain the alignment of the staple shaft in relation to the cage, the engagement portion may be configured to be rotationally stabilized while other implant device elements are moved.

To support the positioning and movement of the staple head through the different alignments and longitudinal locations of the above positions, the staple shaft may also be configured to move the staple head from an insertion to an extended position by having a threaded shaft and rotating the staple shaft in mating threads to extend the staple head away from the cage. The staple shaft may also be configured to move the staple head from the extended position to a deployed position by configuring the staple shaft to rotate the staple shaft and the staple head into the deployed position. The staple shaft may also be configured to move the staple head from the deployed position to a stabilization position by having a threaded shaft and rotating the staple shaft in mating threads of the cage to retract the staple head towards the cage. The staple shaft may also be configured to move the staple head from the deployed position to a stabilization position by having a threaded shaft engaging mating threads of a nut and rotating the nut to retract the staple head towards the cage.

In some embodiments, the staple is positioned on the distal side of the implant to be secured to the distal sidewall of the vertebral body yet control of the positioning of the staple is done by manipulating system elements and features accessible on the proximal side of the implant. These features are particularly beneficial for vertebral procedures where the implants are inserted and secured from a lateral or an oblique approach angle and the implant is implanted across the vertebral body and secured to both lateral sidewalls of the vertebrae. These procedures include the ATP approach to access the vertebral body and implant the implant device.

In some embodiments, components of the implant device may be 3D printed as one unit. For example, the cage and anchor frame of the embodiments shown in FIGS. 40A-42C may be 3D printed as one unit.

In some embodiments, components of the implant device may include lattice or other surface configurations to encourage bone growth and secure the implant device to bone. For example, the cage may be made with portions having lattice structures or it may have a percentage lattice volume such as about 40-70 percent.

The implant device may be manufactured from any suitable material including commercially pure titanium, titanium alloy, polyetheretherketone or any other appropriate material even allogenic bone. In one example, all of the components of the implant device are made of a surgical grade metal such as Titanium (e.g., ASTM F136 Wrought 6Al4V Ti for Implant). The implant device components may be manufactured utilizing conventional machining technology (e.g., milling and turning, mass media and/or electropolish finishing, color anodizing and passivation) or one of the several available methods additive manufacturing methods.

The Implant System:

It is understood that the disclosed implant systems and methods of use may be used with different orthopedic procedures. For illustration purposes only, and not for limitation, an example of the implant system used for intravertebral applications will be described and referred to as a vertebral implant system, an intravertebral implant system, a vertebral implant device and an intravertebral implant device. In this illustrative example, the implant system comprises a vertebral implant device configured for use as an intravertebral implant device. For illustration purposes and not for limitation, one example of the vertebral implant device is shown in FIG. 2.

Figure 2:
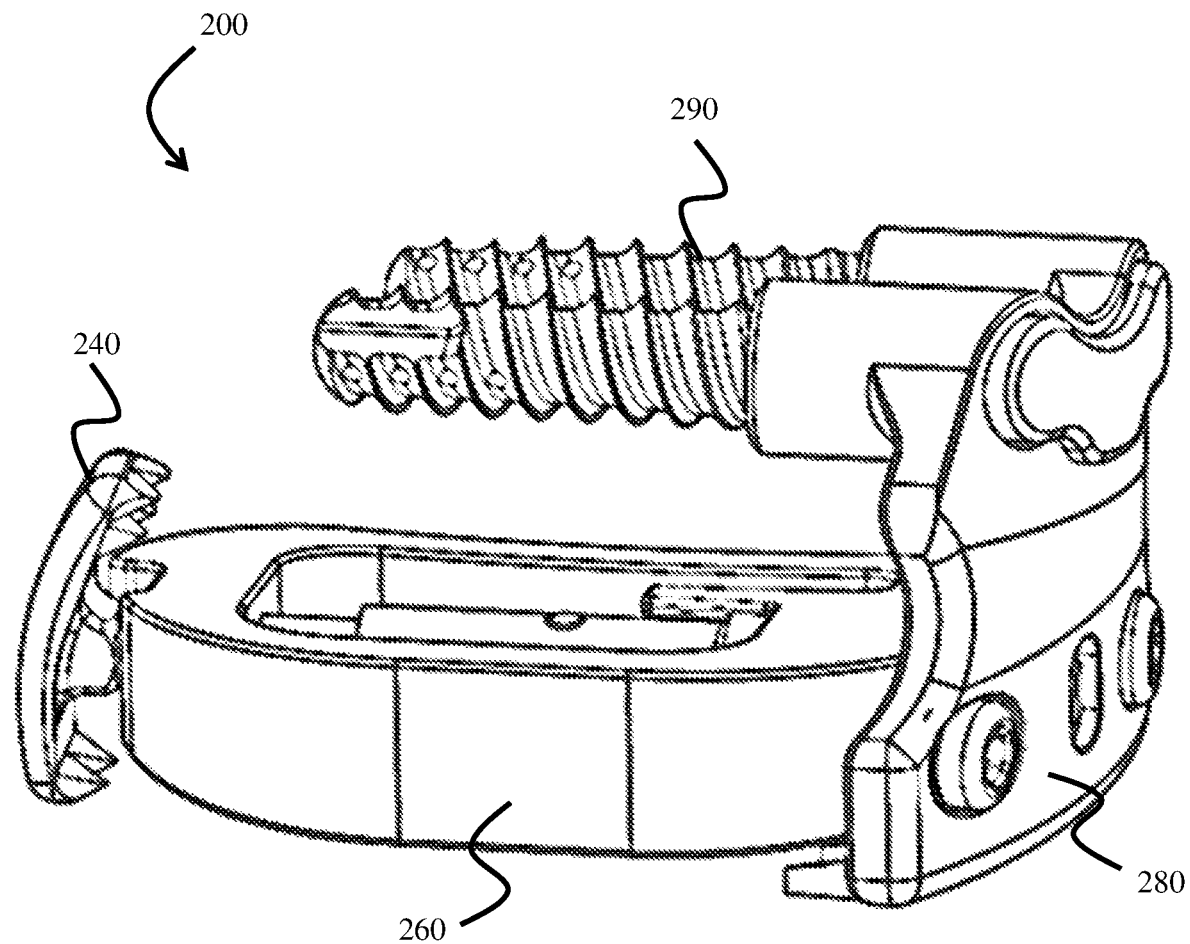
FIG. 2 illustrates an example of an assembled implant device.

As shown in the example of FIG. 2, the vertebral implant system generally comprises an intravertebral implant device 200 comprising a cage 260 and one or more securing element configured to secure the cage 260 to the vertebral body. The securing element may be any suitable element or combination of elements to secure the cage 260 and the implant device 200 to a superior and inferior portion of the vertebral body. In the example shown, the securing element may comprise one or more staple 240 received in, and rotationally and longitudinally adjustable relative to the cage 260. From a proximal end to a distal end, the example shown comprises an anchor frame 280, the cage 260 and a distal staple 240. In some embodiments, the intravertebral implant device 200 further comprises one or more anchoring element configured to anchor the implant system in the vertebral body. The anchoring element may be any suitable element or combination of elements to anchor the implant device 200 to the vertebral body. As shown, the anchoring element may be one or more bone screw 290. As shown, staple 240 is configured to be positioned either inside or outside the boundaries of the vertebral body when implanted. In some embodiments, the intravertebral implant device may further comprise a second inner staple that may be configured to be deployed within the vertebral body. In the example shown, for intravertebral applications, the staple dimensions may be non-symmetrical to account for varied bone dimensions resulting from the osteotomy.

Figure 6A:
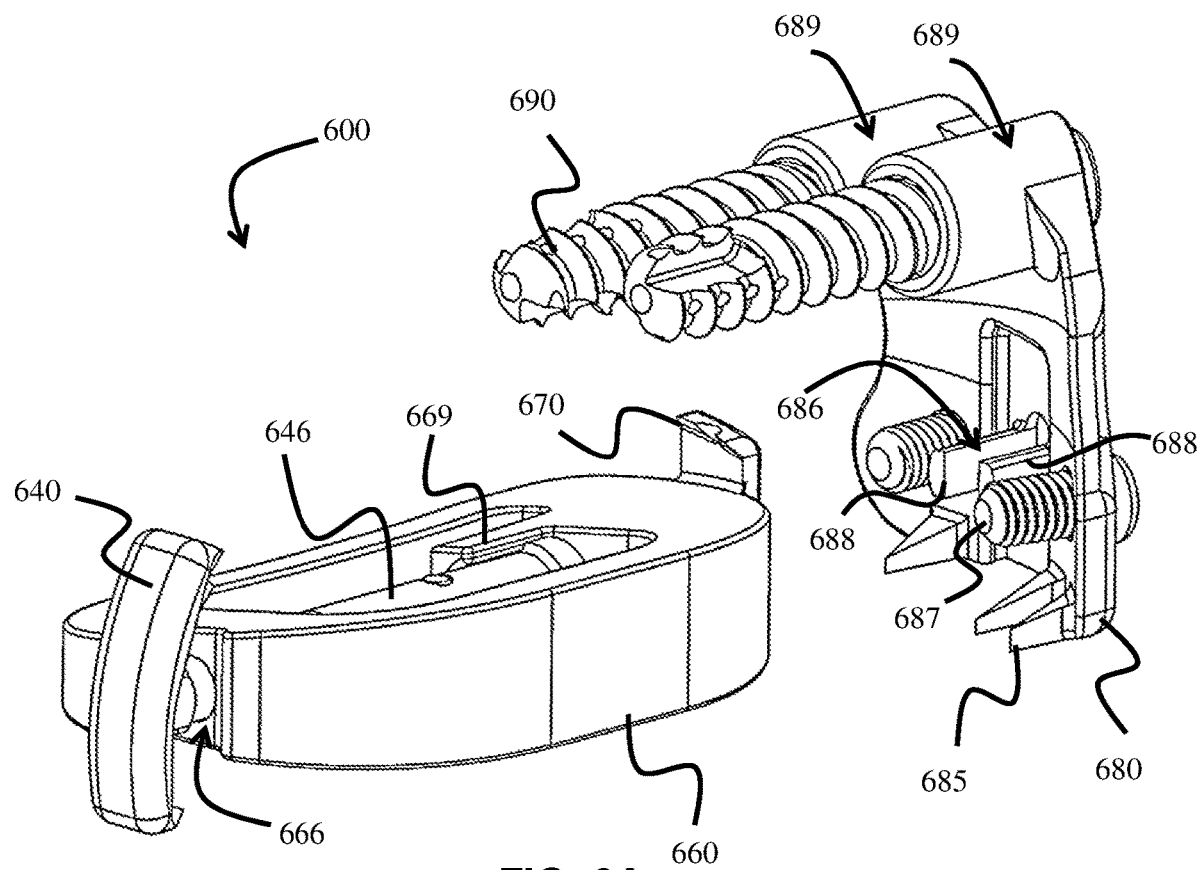
FIGS. 6A and 6B illustrate views of a partially assembled example of the implant device where
Figure 6B:
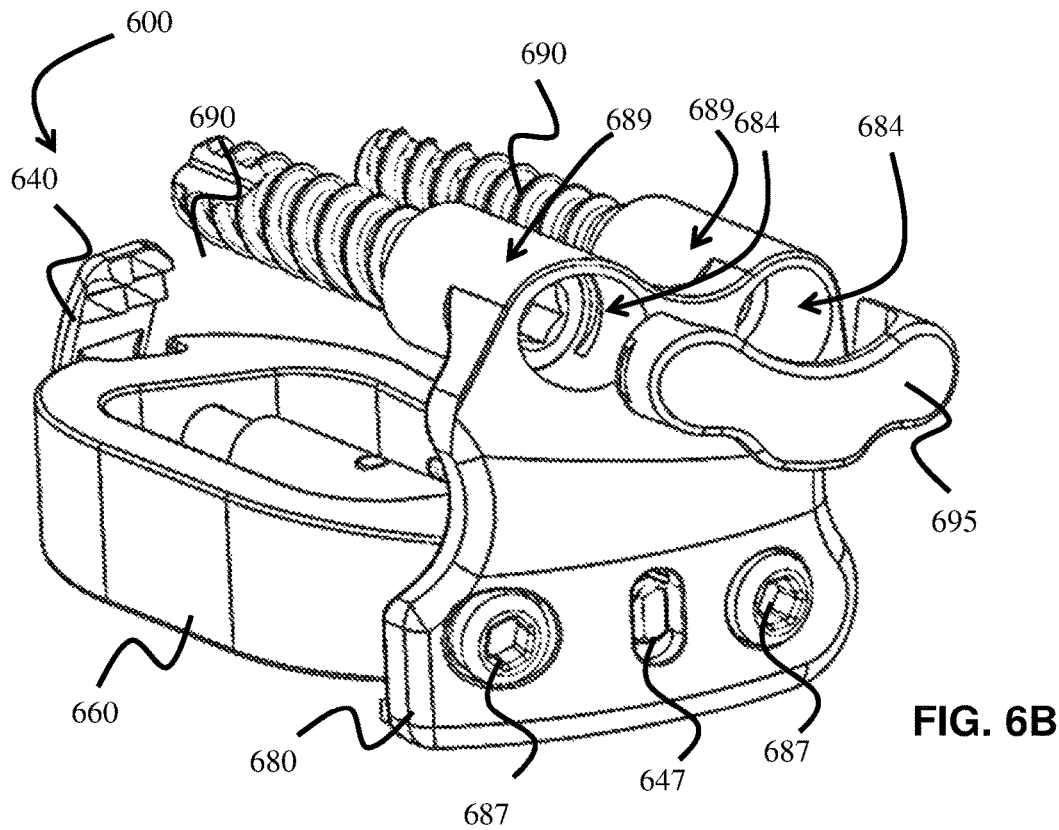
Figure 7:
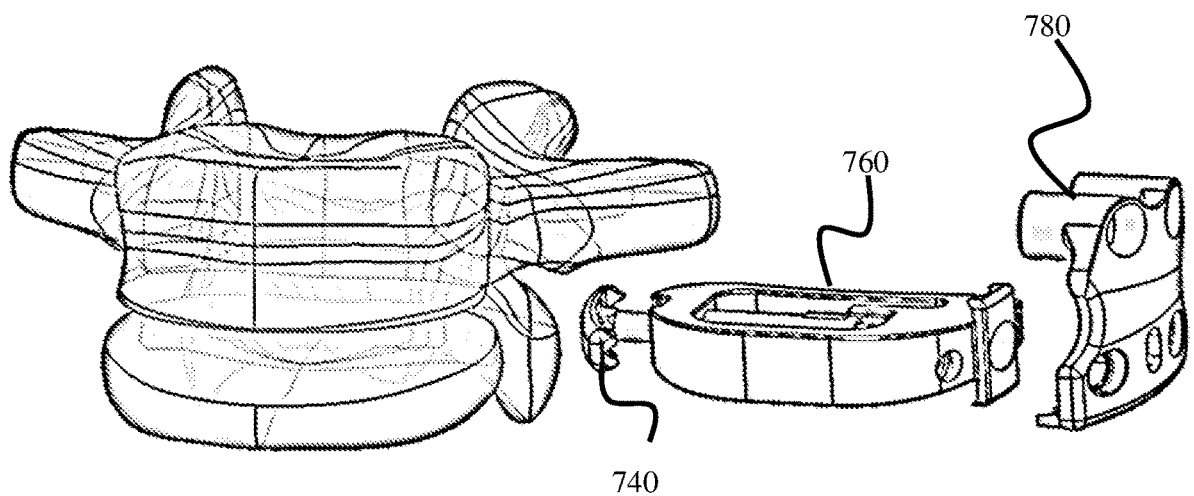
FIG. 7 illustrates an example of the implant device with the cage and anchor frame of the implant partially exploded.
Figure 8:
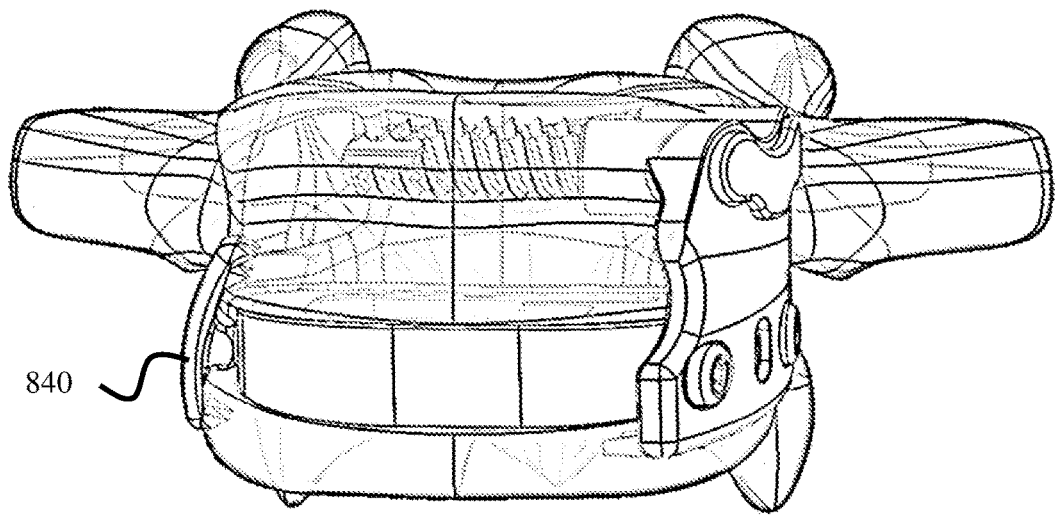
FIG. 8 shows the example of the implant device of FIG. 7 with the components as implanted in a vertebrae.
Figure 9A:
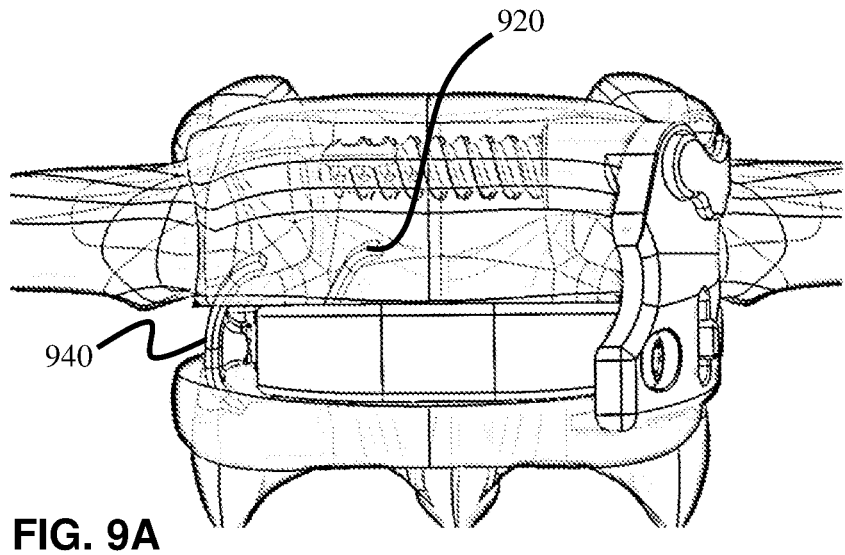
FIGS. 9A-9C illustrate an example of the implant device where
Figure 9B:
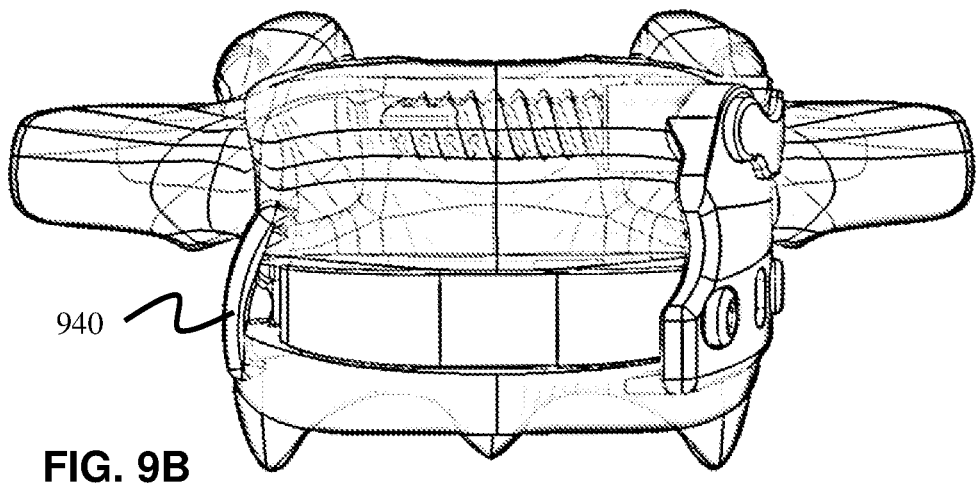
Figure 9C:
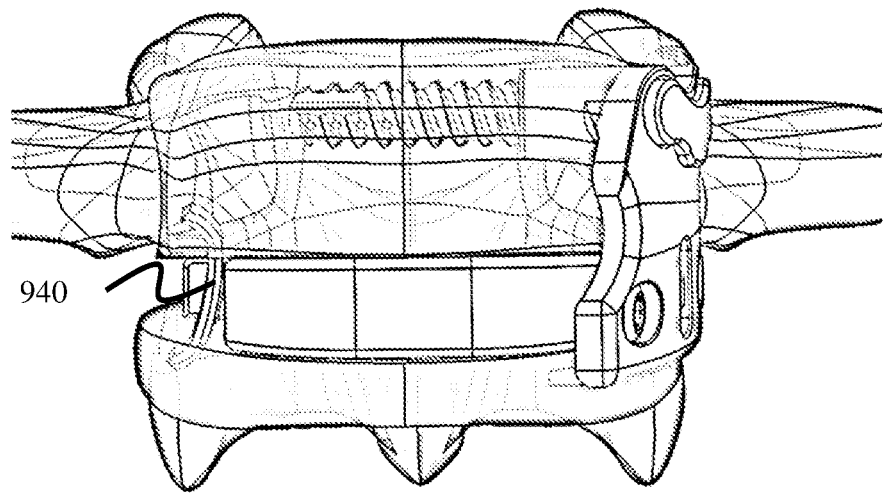

FIGS. 6A-9C further illustrate examples of a vertebral implant device. FIGS. 6A and 6B show additional partially exploded views of the example of the vertebral implant device consistent with the example shown in FIG. 2. FIG. 7 illustrates a partially exploded view of the cage and anchor frame components of a vertebral implant device alongside an example vertebral body with an osteotomy as may be used in an intravertebral application. FIG. 7 shows the distal staple 740 prior to being deployed. FIG. 8 shows the example of FIG. 7 assembled and implanted in a vertebral body with the staple 840 deployed. These figures also embody sagittal only and sagittal plus coronal correction geometries. FIGS. 9A-9C show additional examples of a vertebral implant device assembled and implanted in a vertebral body as used in an intravertebral application. FIG. 9A shows an example with both a distal staple 940 and a second inner staple 920 both of which are intraosseous. It is understood that one staple can be positioned extraosseous (outside the vertebral body) while the other is positioned intraosseous.

Figure 3A:
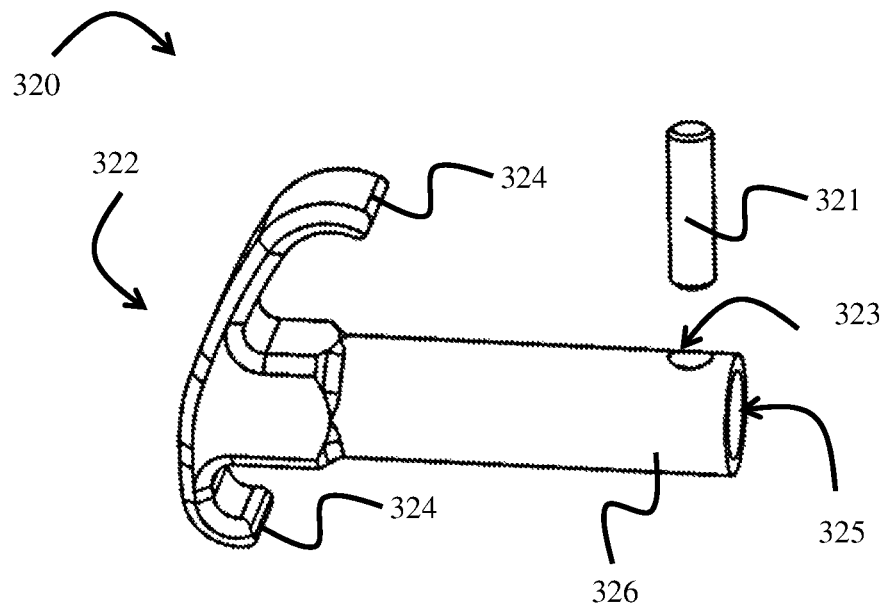
FIGS. 3A-3B show examples of staples where

Referring to FIG. 3A, an example of an inner (intraosseous) staple 320 comprising an inner staple head 322, one or more inner staple tine 324 and an inner staple shaft 326. The inner staple tines 324 may be any shape to secure the staple head 322 in the vertebral body. The inner staple tines 324 are generally configured for intraosseous deployment and are stiff and sharpened to penetrate vertebral bone. In the example shown, the inner staple shaft 326 has an inner staple shaft bore 325 and mating components to mate the inner staple 320 to another element such as the distal staple 340. In the example shown, the mating components comprise a pin 321 and a mating pin hole 323.

Figure 3B:
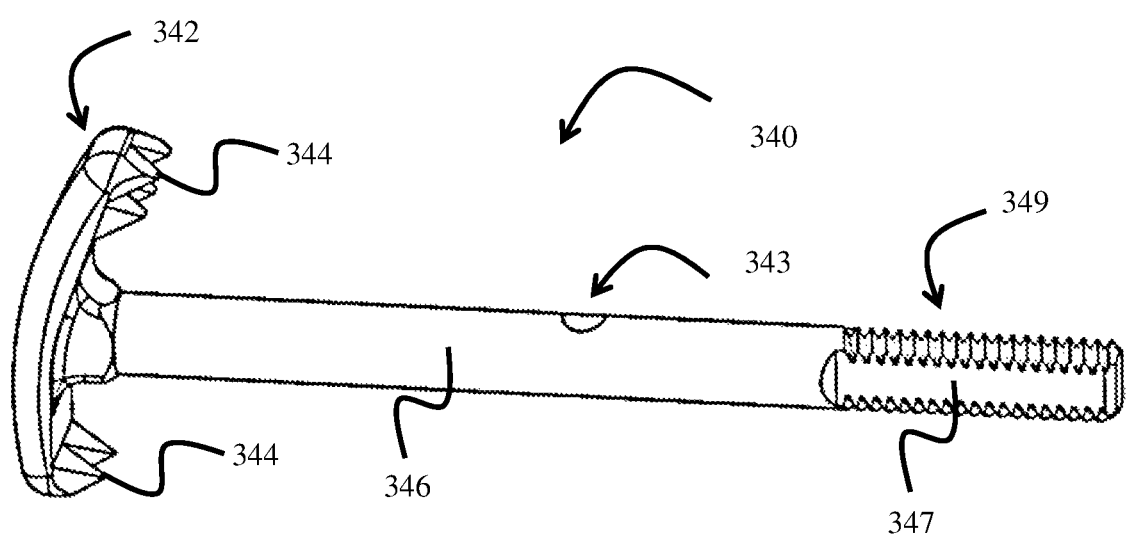

FIG. 3B illustrates an example of a distal staple 340 comprising a distal staple head 342, one or more distal staple tine 344 and a distal staple shaft 346. It is understood that although the example of the staple 340 illustrates a unitary staple head from one end to the other, in some embodiments, the staple head may be comprised on multiple components such as components hinged or otherwise coupled to each other. Like the inner staple tines, the distal staple tines 344 may be any shape to secure the staple in the vertebral body and they are generally stiff and if intended for intraosseous deployment, sharpened to cut through vertebral bone, if intended for external deployment, in the far side of the vertebral body, they will comprise smooth rounded surfaces with the exception of the distal, bone facing staple tine edge 344. In the example shown, the distal staple shaft 346 has mating components to mate the distal staple 340 to another element such as the inner staple 320 such as a pin hole 343 to receive a pin. The distal staple shaft 346 also has an engagement portion 347 at its proximal end configured to provide a means to engage the cage and rotate the distal staple shaft 346 and the distal staple head 342. Engagement portion 347 may comprise any type of profile that can be engaged by a tool to rotate the staple shaft 346. As shown, one example of the engagement portion 347 may be an off-round profile such as a profile with a flat surface (flat) to allow a mating engagement with a tool having a mating recess with a flat to rotate the engagement portion 347 and the staple shaft 346. The distal staple shaft 346 may further include elements to adjustably couple the distal staple 340 to the cage. As shown, the distal staple shaft 346 includes a coupling portion 349 configured to mate with a coupling element. As shown the coupling portion 349 of the staple shaft 346 may be a threaded portion configured to mate with a threaded coupling element such as a nut. The coupling portion 349 of the staple shaft 346 and the coupling element engage each other to function as a coupling device to adjust the longitudinal position of the staple head 342 relative to the cage. In the example shown, the threaded portion and the threaded coupling element are configured to cause the distal staple head 342 to retract towards the cage as the staple shaft 346 is rotated in one direction and extend away from the cage as the staple shaft is rotated in the other direction. In some embodiments, the threaded portion mates with a threaded coupling element, such as a nut (for example only, see example in FIG. 18A), positioned on the staple shaft and engaging the cage.

Figure 3C:
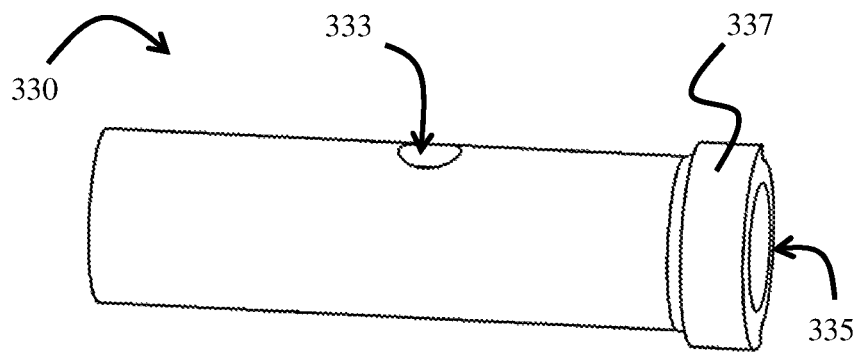
FIGS. 3C-3E show examples of a locking sleeve where
Figure 3D:
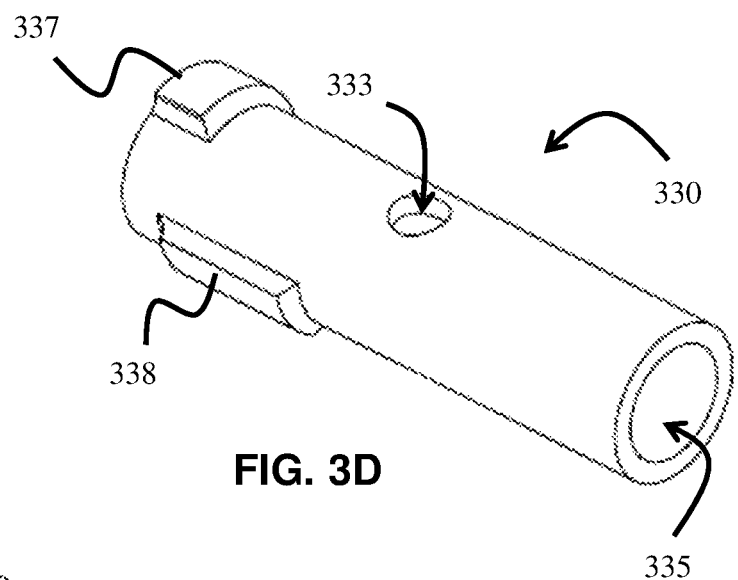
Figure 3E:
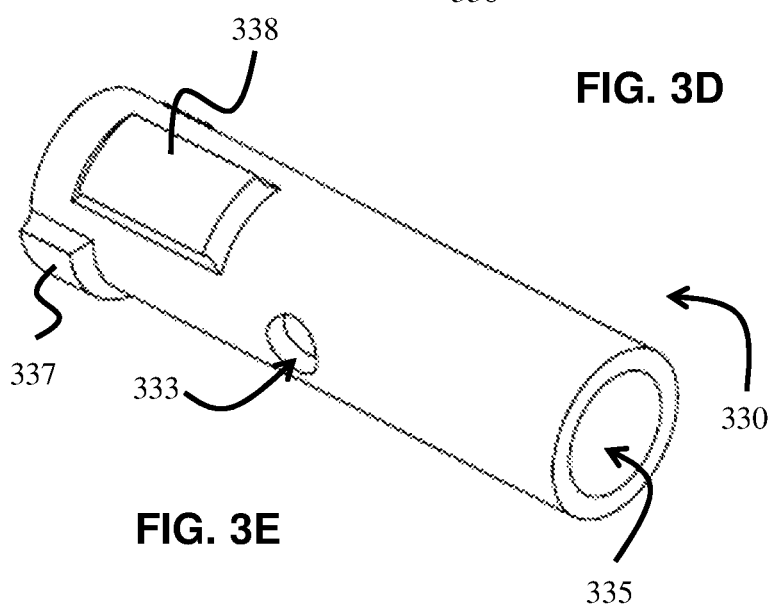

FIGS. 3C-3E illustrate different views of an example of a locking sleeve 330. The locking sleeve 330 is generally a cylindrical sleeve configured to receive one or more staple shaft through a central bore 335. The locking sleeve 330 has a through hole 333 to receive a mating element like a pin to couple the locking sleeve 330 to the one or more staple shaft. The locking sleeve 330 may have one or more staple stop feature to limit the rotation of the sleeve through desired positions. As shown, staple stop 337 on the exterior surface of the locking sleeve 330 is configured to function as a limit to the rotation of the sleeve by having the staple stop 337 physically engage other implant elements to stop the rotation of the locking sleeve 330 and staple shaft at certain positions. The staple stop 337 shown may engage a mated protrusion on the cage, a cage stop, to stop the locking sleeve 330 and the coupled staple shaft in a particular position. The locking sleeve 330 may also have a key configured to keep the locking sleeve 330 in a certain position. As shown, key 338 is a protrusion on the exterior surface configured to mate with a cage stop or other mated protrusion or a locking channel on the cage whereby the rotation of the locking sleeve 330 is stopped and kept in a certain location. Although shown as a separate element, the locking sleeve 330 and its staple stop 337 and key 338 may be integrated into other implant device elements such as the one or more staple shaft or elements coupled to implant device elements.

In an example that uses an inner staple and distal staple together, the distal staple shaft may be received in and through the inner staple shaft bore and the pin may be inserted through both pin holes to couple the two staple shafts. With the shafts coupled, they rotate together such that when the distal staple shaft 346 is rotated through the use of the engagement portion, the inner staple shaft and the inner staple 322 are also rotated.

The locking sleeve may be similarly coupled to multiple staple shafts. The staple shaft may be received in and through the locking sleeve bore and the pin may be inserted through both pin holes to couple the locking sleeve and the staple shafts. With the shafts and sleeve coupled, they rotate together such that when the staple shaft is rotated through the use of the engagement portion, the locking sleeve, the staple shaft and the staple is also rotated.

Figure 4A:
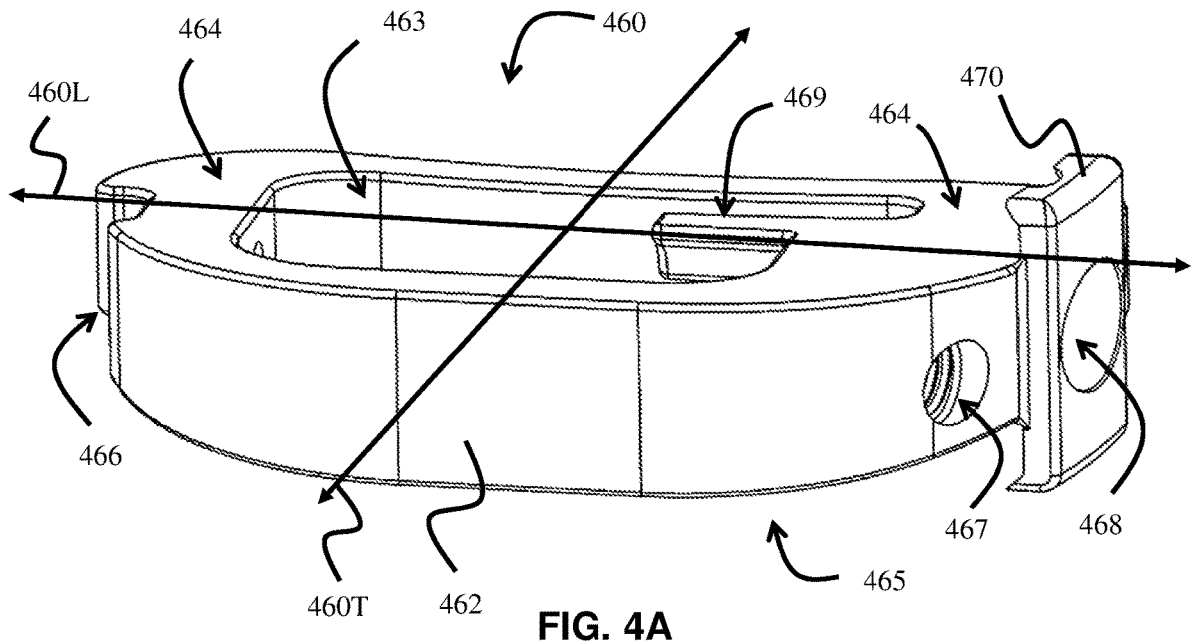
FIG. 4A shows an example of a cage without a staple or staple shaft.
Figure 4B:
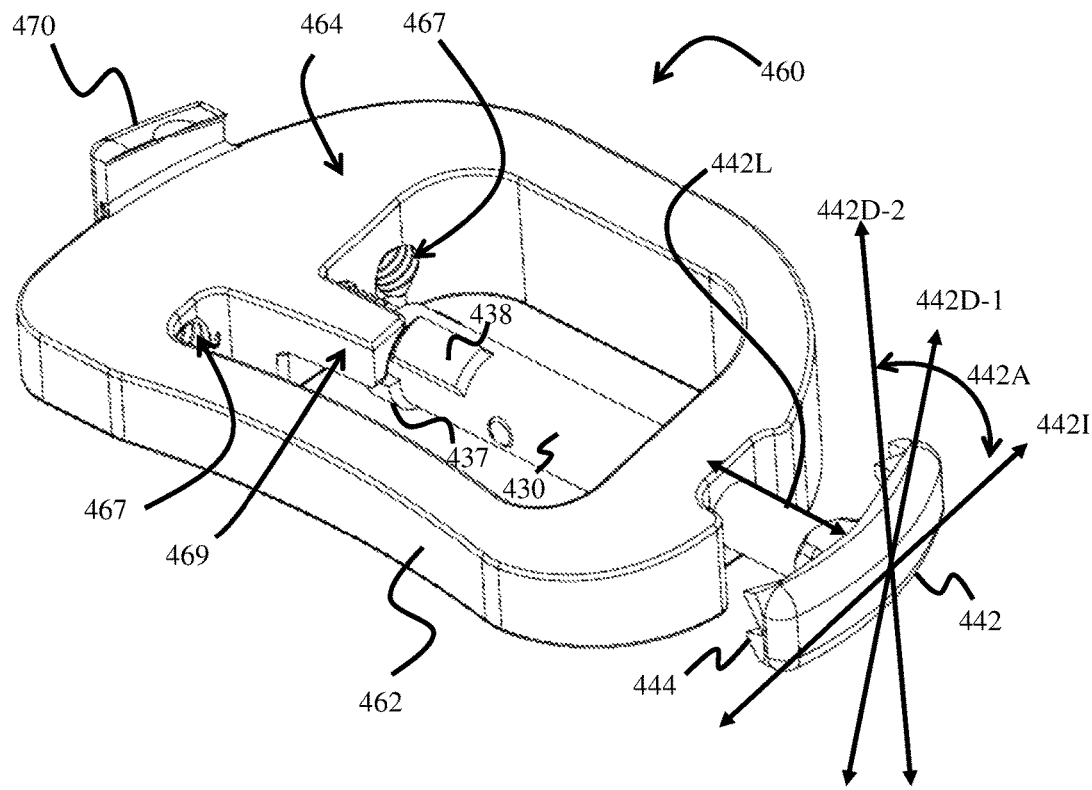
FIG. 4B shows an example of a cage with a staple in an undeployed position.
Figure 4C:
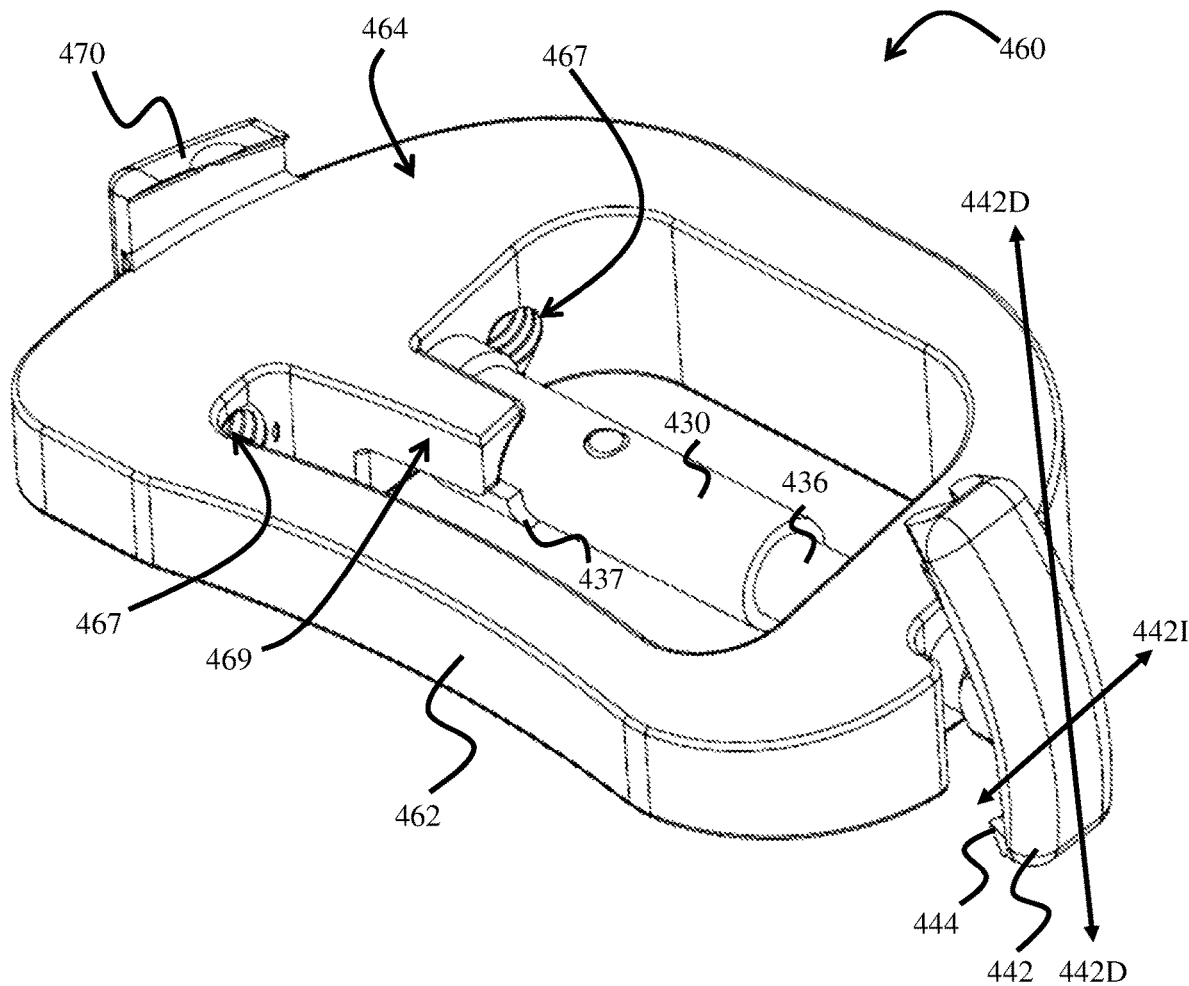
FIG. 4C shows an example of a cage with a staple in a deployed position.

FIGS. 4A-4C illustrate examples of a cage 460. Referring to FIG. 4A, the cage 460 comprises a cage body 462 defining an upper surface 464, a lower surface 465 and a cavity 463. This example shows cage screw recesses 467 to receive cage screws and couple the cage body 462 with other system components. The upper surface 464 defines a cage upper surface plane for the implant device and the lower surface 465 defines a cage lower surface plane for the implant device. The configuration of the cage 460 with a cavity 463 or other gaps within the cage body 462 is to allow for placement of ample bone graft (autogenous, allogenic or synthetic) to reach the osteotomized vertebral body both superior and inferior when the cage 460 is positioned within the vertebral body and facilitate fusion (healing). The dimensions of the cage surface planes (e.g., angles and distances between them) define an offset dimension that is used to alter the planes of the endplates of the vertebral body. For example, the dimensions of the cage define a cage surface angle between the cage upper surface plane and the cage lower surface plane to alter the endplate surface planes of a vertebral body when the cage is implanted in the vertebral body. The dimensions of the cage may also define a distance between the cage upper surface plane and the cage lower surface plane to alter the height defined by the distance between the endplate surface planes of a vertebral body when the cage is implanted in the vertebral body.

The cage may have variable dimensions along its longitudinal axis 460L which defines a cage longitudinal angle between the cage upper surface plane 464 and the cage lower surface plane 465. The cage 460 may also have variable dimensions along its transverse axis 460T to provide a cage transverse angle between the cage upper surface plane 464 and the cage lower surface plane 465. Cages may have various angles to accommodate different insertion positions and to provide different correctional effects onto the vertebral endplates once inserted. In some embodiments, the cage may have variable dimensions along both the longitudinal axis and the transverse axis to provide correction effects in multiple planes once inserted.

In some embodiments, the cage may have a surface treatment or a lattice configuration on one of or both the upper surface of the lower surface to encourage bone growth, apposition and/or adhesion.

Referring to FIG. 4A, the cage 460 also has a through bore 468 extending along its longitudinal length shaped to receive and rotatably couple with the staple shaft so that the staple head 442 can be rotated about a rotational axis of the staple head 442 by a rotation of the staple shaft 436 into a deployed position once it extends into or beyond the far side of the vertebral body. The cage 460 may also have a recess 466 at its distal end to receive and countersink all of or a portion of the staple head when the implant device is being implanted into the vertebra.

Referring to FIGS. 4A, 4B and 4C, the cage 460 may have a cage stop 469 to function as a rotational stop with the staple stop 437 on the locking sleeve 430. The cage stop 469 is a generally a protrusion within the cavity 463 of the cage 460 to stop rotation of the locking sleeve at a position that properly positions the staple head. The cage stop 469 may be an elongated protrusion that in cooperation with the stop 437 and/or key 438 keeps the locking sleeve properly positioned as it and the staple shaft are extended, deployed and retracted into the through bore 468 of the cage 460. This example shows cage screw recesses 467 extending through the walls of the cage body. The cage 460 may also have a recess at its proximal end to receive and countersink the engagement portion of the staple shaft when the implant device is secured to the vertebra. The proximal recess may also retain a coupling element, such as a threaded nut, to mate with a threaded coupling portion of the staple shaft whereby rotating the threaded nut, engaged the coupling portion and slidably extend and retract the staple head relative to the cage.

The cage 460 may also have a proximal tab 470 with tab tines extending outside of the upper and lower surface planes of the cage 460. The tab and tab tines are configured to engage the side wall of the vertebral body and cooperate with the staple to secure the implant device. For example, when the staple is positioned on the distal side of the vertebral body, both the staple and proximal tab 470 secure and stabilize the cage 460 to the superior vertebral body portion and the inferior vertebral body portion of the vertebral body. When the staple is retracted towards the cage, this further secures the staple and the proximal tab 470 to the vertebral body.

Although not shown, the cage 460 may further have additional elements. For example and not for limitation, the cage may have additional threaded holes to receive structures such as additional plates or other hardware and the cage may have additional through holes to allow for insertion of materials through the cage and into the vertebral body. These additional elements may be located on the top, bottom or outside perimeter of the cage.

FIGS. 4B and 4C illustrate various alignments of the staple head 442. As shown, the staple head 442 is in an insertion alignment 4421. The staple head 442 may be rotated through various angles 442A to be put into deployed alignments such as 442D-1 and 442D-2. In some embodiments, the cage may allow the staple to be positioned in 6 degree increments of alignment relative to the cage. FIG. 4B also shows the longitudinal location 442L of the staple head in an extended location in relation to the cage.

With the staple shafts positioned in the cage bore, the staples can be rotatably coupled through a channel in the cage so that the staple can be rotated by a rotation of the shaft into a deployed position. The distal portion of the shaft is positioned through the bore of the cage that defines an opening (not shown) on the distal end of the cage. The proximal portion of the distal staple shaft is also positioned through the bore of the cage and the tab so that it can be exposed to be coupled with a mating tool to rotate the staple shaft.

Consistent with FIG. 4B, during insertion of the intravertebral implant device, the one or more staple head 442 is configured in an undeployed or horizontal position with staple tines 444 positioned generally parallel with the transverse surface planes of the cage 460 to allow it to fit through the osteotomy (or intervertebral space) during insertion. Once the staple head 442 and cage 460 are in the correct position, the engagement portion of the staple shaft 436, such as a hex, flat, D shaped or other non-round profile on the proximal end of the staple shaft 436, is rotated by a mating engagement tool such as a staple drive handle assembly. Consistent with FIG. 4C, by rotating the staple shaft 436 with the engagement portion, the staple tines 444 of the staple head 442 are rotated into a deployed position to engage and secure the staple tines 444 and the implant device in the vertebral body. When anchored in an anchored position, the staple tines 444 may engage the spongy cancellous bone of the vertebral body, or they may engage the compact bone on the distal wall of the vertebral body.

As shown in FIG. 5A, the anchor frame 580 generally provides the structural elements to anchor and further secure the implant device to the vertebral body. Also referred to as a vertical member in patent applications to which this application claims benefit to, the anchor frame may be any type of structural element having any position or angle relative to the cage to help secure implant device components to bone. Although referred to as a vertical member, and although the anchor frame may be generally oriented vertical to a longitudinal surface plane of the cage when the cage is positioned horizontally, the anchor frame may be any a structural element having any shape and having any relative position or angle relative to the cage that helps secure the implant device to the vertebral body. And although illustrated in example embodiments in this description a generally being oriented perpendicular or orthogonal to the longitudinal surface plane of the cage, the orientation of the anchor frame may be at any angle or orientation to secure the implant to a bone such as to the sidewall of a vertebral body. And although the anchor frame is illustrated as a unitary member in some of the example embodiments, the anchor frame may also comprise multiple elements such as struts, trusses or multiple plates and the anchor frame may be configured to be adjustable in one or more dimension. As shown in this example, the anchor frame 580 generally comprises a plate and a structural element to anchor the implant device to the vertebral body. For example, the element to anchor the device to may be one or more through hole 584 to accept an anchoring element. The anchoring element may be any element to anchor the anchor frame 580 to the vertebral body. For example, the anchoring element may be a bone screw 590 (see FIG. 5C). Alternatively, the anchoring element may be an expandable anchor akin to a drywall screw or molly bolt. The anchor frame 580 may also have elements to secure the implant device to other system components. As shown, one example element to secure the implant device to other system components may comprise one or more through hole 582 that may receive a coupling element like a cage screw 587 (see FIG. 5B) to secure an element such as the cage (see FIG. 4) to the anchor frame 580. In some embodiments, one or more shaped prong 583 may be provided that defines a recess 586 shaped to mate with the shape of the shaft engagement portion to lock the shaft in a particular rotational position. The anchor frame 580 may further have at least one anchor frame tooth 585 to further secure the anchor frame into the side of the vertebral body. In some embodiments, a tulip screw head may be used to attach a longitudinal rod or cord or tether between multiple vertebrae. In some embodiments, a bone screw lock 595 (see FIG. 5D) may be provided to provide anti-backout features for the bone screws.

In some embodiments, the features of the anchor frame coupling the cage and the anchoring elements may be provided by other types of anchor frames or multiple anchor frames or a divided element coupled by one or more anchor frame. The anchor frame may be a fixed or adjustable anchor frame and they may be used in combination.

FIGS. 6A and 6B show alternative views of an example of a vertebral implant device 600 showing additional features. Referring to FIG. 6A, the vertebral implant device 600 comprises a cage 660, an anchor frame 680 a staple 640, a tab 670 and anchoring elements 690. As shown in this example, the staple 640 is a convex staple. The cage screws 687 are shown in the cage screw bore of the anchor frame 680 and positioned to be coupled with the cage 660. The anchoring elements 690, here bone screws, are shown in the anchor posts 689 of the anchor frame 680 positioned to be coupled with the vertebral body. Locking arms 688 are shown that define a locking channel 686 for the engagement portion 647 of the distal staple shaft 646. The shape of the locking channel 686 mates with the non-rounded shape of the engagement portion 647 of the shaft when the shaft is in a particular rotational position to lock the shaft in that position. This view also shows the recess 666 on the distal end of the cage 660. As shown, the anchor frame 680 further comprises at least one anchor frame tooth 685 to further secure the anchor frame into the side of the vertebral body. Also shown is a cage stop 669 to function as a rotational stop of the staple shaft 646.

Referring to FIG. 6B, the vertebral implant device 600 comprises a cage 660, an anchor frame 680 a staple 640 and anchoring elements 690. As shown in this example, the distal staple 640 has a convex shape. The engagement portion 647 of the distal staple shaft is shown in and blocked in the locking channel of the anchor frame 680. The anchor frame has one or more through hole 684 to accept an anchoring element such as a one screw. The bone screw anti-backout feature 695 is shown to be positioned within the anchor posts 689 to block the proximal end of the anchoring elements 690, here bone screws, thus to provide anti-backout features for the bone screws.

When assembled and implanted in the vertebral body, the external surface dimension and configuration of the intravertebral implant device are able to correct the relative orientation of a superior endplate surface plane and an inferior endplate surface plane of a vertebral body to alter the alignment of the spine. The external surface configuration of the cage and the intravertebral implant device may be altered by using different configurations of intravertebral implant device components. For example, the cage may be configured to have different cage surface angles in either the coronal or sagittal planes to create different external surface configuration when implanted in the osteotomy. The cage may also be configured to have different heights to create different amounts of expansion when implanted in the osteotomy. Sets of multiple exchangeable cage configurations can provide implant device options to accommodate different vertebrae, different sized patients, different amounts of correction and different orientations of insertion.

Furthermore, some embodiments of the implant system may be configured to alter the alignment of the spine in multiple planes. This multi-plane alignment may be made by the insertion angle of the implant and/or the dimensions of the cage and the resulting cage surface angles.

In some embodiments, additional through holes may be provided in the anchor frame and/or the cage to accommodate additional pedicle screws to further anchor the implant device to the vertebral body. In these embodiments, the pedicle screw may be received in the additional through holes and into the vertebral body.

In some situations, the vertebral body is too small to safely accommodate bone screws as a method to secure the implant. In those situations, the implant may have other anchoring elements to secure the implant device to the vertebral body. The anchoring element may be any element to secure a component of the implant device to the bone. In one example, the anchoring element may comprise one or more teeth extending from the anchor frame to penetrate into the wall of the vertebral body and secure the anchor frame and the implant device.

Figure 25A:
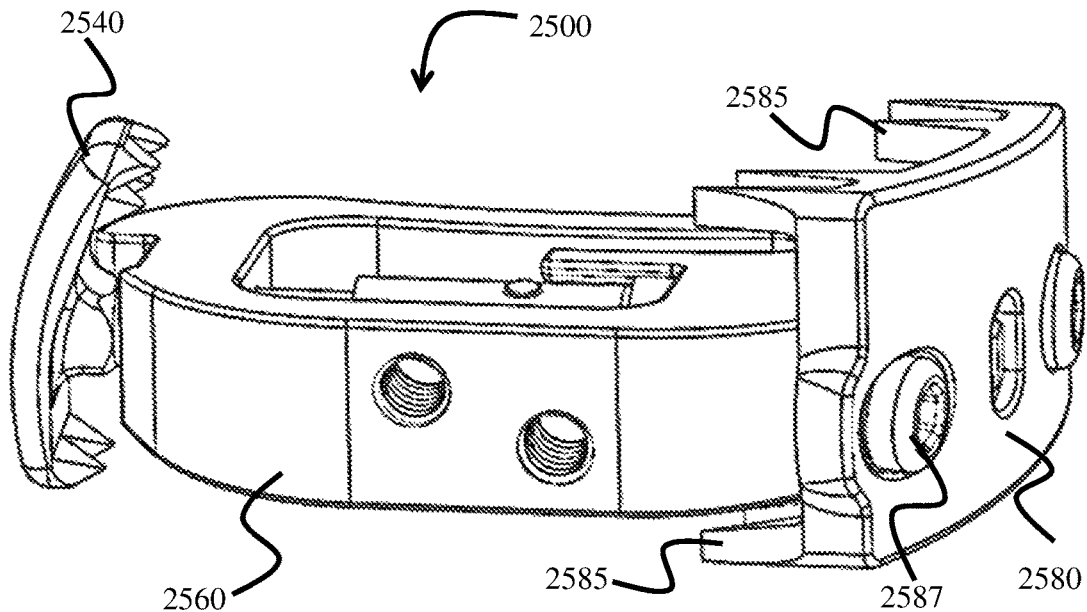
FIGS. 25A-25C show different views of an example of the implant system.
Figure 25B:
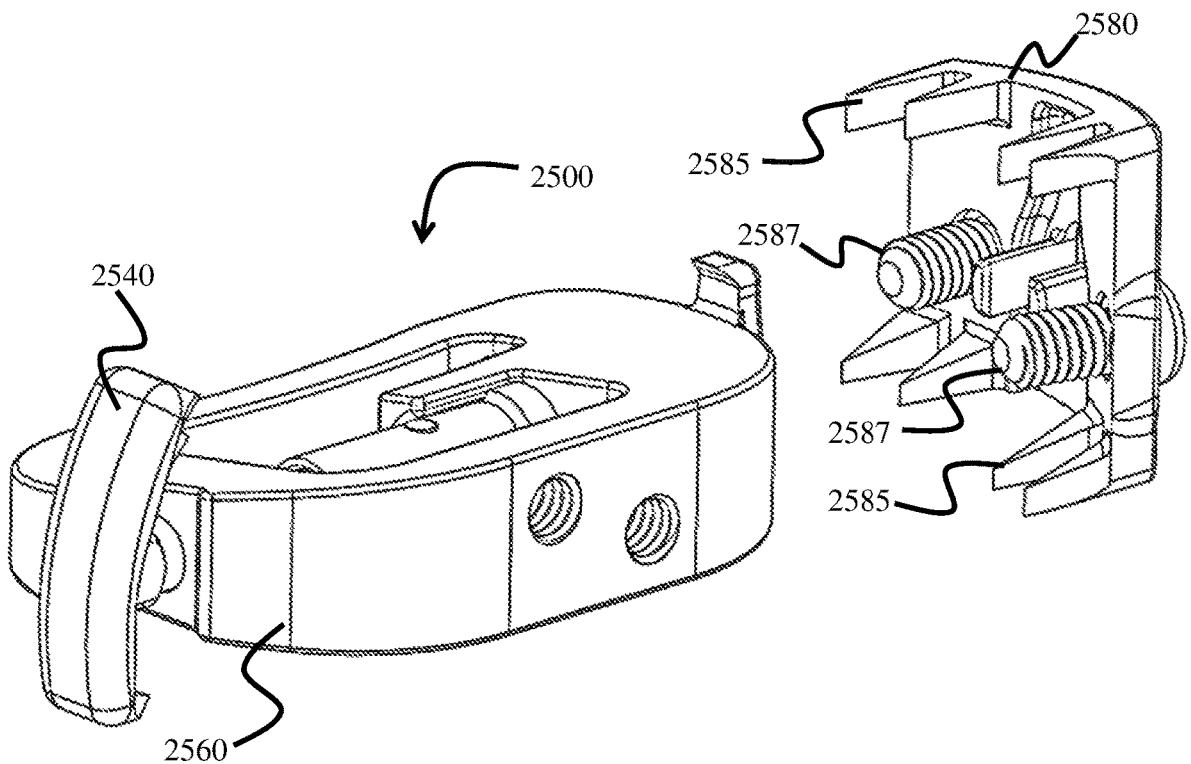
Figure 25C:
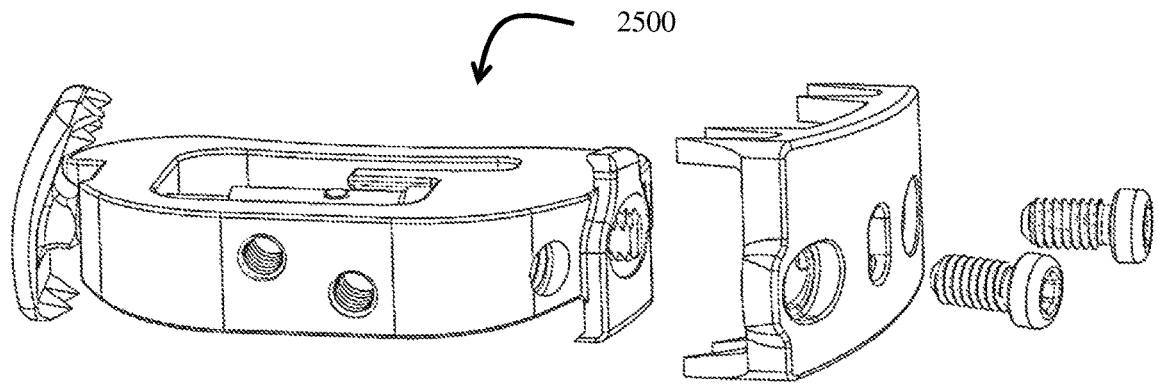
Figure 26A:
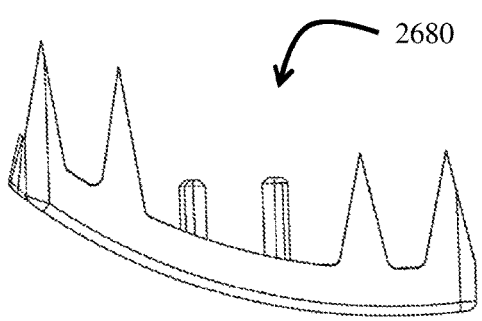
FIGS. 26A-26E show different views of an example of the anchor frame.
Figure 26B:
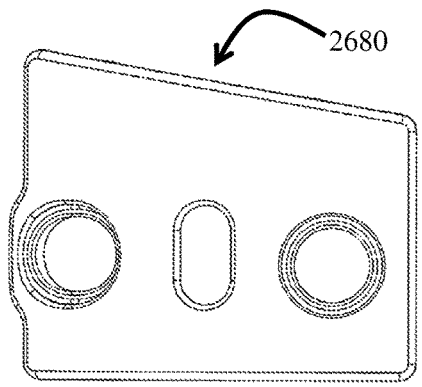
Figure 26C:
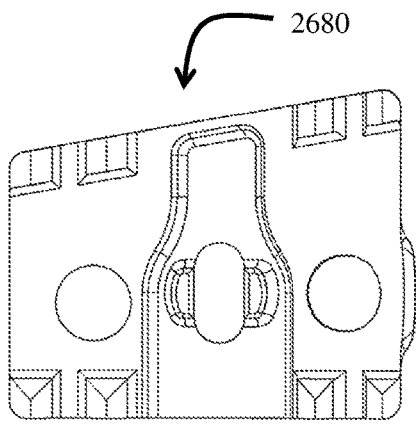
Figure 26D:
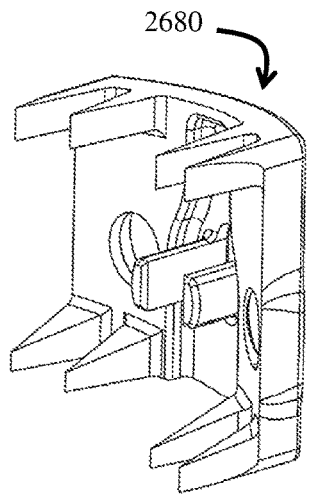
Figure 26E:
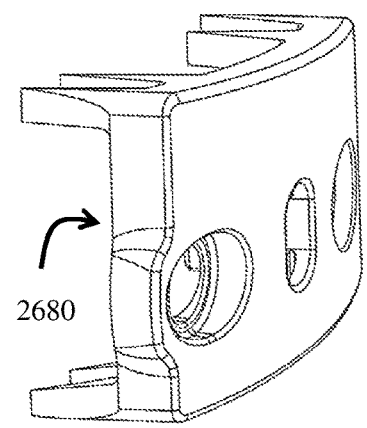

FIGS. 25A-25C show different views of an example of the implant system having teeth as anchoring elements. As shown, this example of the implant device 2500 has a cage 2560, a distal staple 2540 and anchor frame 2580 similar to the example described above. This example includes cage screws 2587 to secure the anchor frame 2580 to the cage 2560. Different than those examples, one or more teeth 2585 are used to secure the implant device 2500 to the vertebral body. FIGS. 26A-26E show different views of an anchor frame 2680 consistent with this example.

Although the examples shown are asymmetrical or non-symmetrical about a horizontal mid-line plane of the implant device, it is understood that some embodiments of the implant components may be configured to create a symmetrical implant device about its mid-line horizontal plane.

The Implant System Used in Intervertebral Applications:

It is understood that the above described implant systems and methods may also be used for intervertebral applications such as an arthrodesis procedure. For example, the implant systems may be able to use the cage to separate two vertebral bodies and the distal staple and the proximal tab or other similar structure may be used to secure the implant device to the superior and inferior vertebral bodies.

Generally, these implant systems have similar features in respect to the horizontal plane so that sufficient structure is available to engage both vertebral bodies. These implant systems may also have retracting features for the distal staple or proximal tab to further secure the implant device to the walls of the vertebral bodies.

Some implant systems may be configured specifically for intervertebral use. For illustration purposes only, and not for limitation, an example of the implant system used for intervertebral applications will be described and referred to as a vertebral implant system, an intervertebral implant system, a vertebral implant device and an intervertebral implant device.

Figure 27:
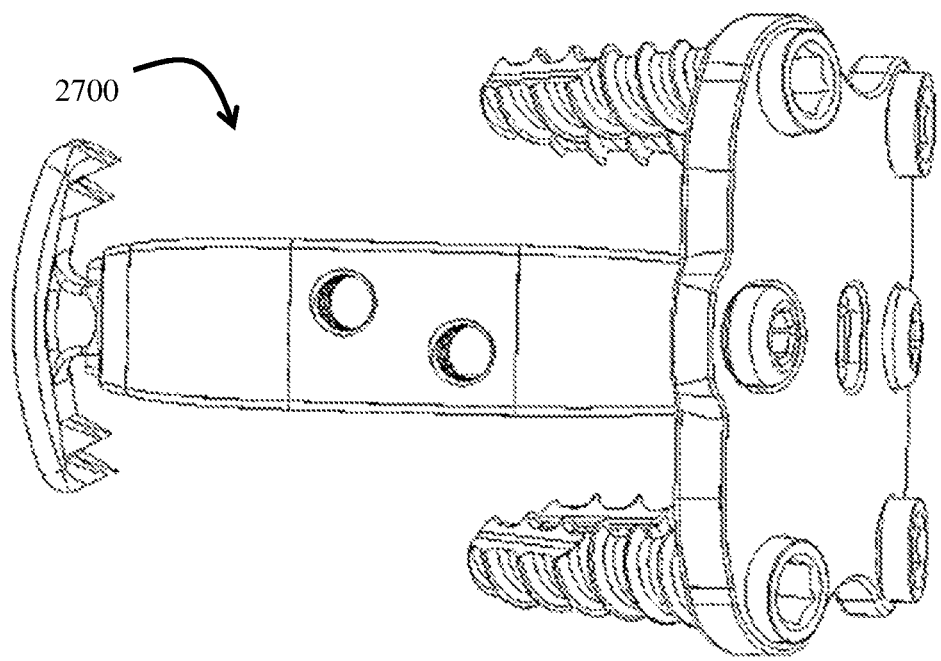
FIG. 27 shows an example of the implant system for use as an intervertebral implant system.

FIG. 27 shows an example of the vertebral implant system 2700 for use as an intervertebral implant system to be positioned between two vertebral bodies. As described above, the cage may be used to separate the bodies and may also be used to correct alignment of the bodies. The distal staple and the anchor frame may be used to secure the implant device in position between the bodies. For intervertebral use, the staple and the anchor frame are more symmetrically extended above and below the cage to secure the cage to the two vertebral bodies.

Figure 28:
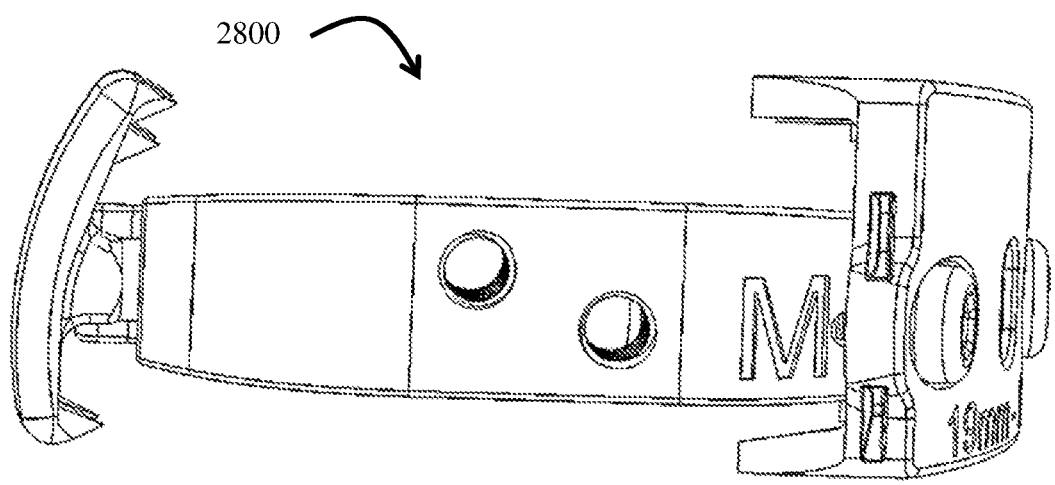
FIG. 28 shows an example of the implant system for use as an intravertebral implant system.

FIG. 28 shows another embodiment of the vertebral implant device 2800 for use as an intravertebral implant system to be positioned between two portions of a vertebral body. For intravertebral use, the staple and the anchor frame are less symmetrically extended above and below the cage to accommodate less bone to secure the cage to the two vertebral body sections. This embodiment is consistent with the embodiments described that use one or more teeth as securing elements.

Figure 29A:
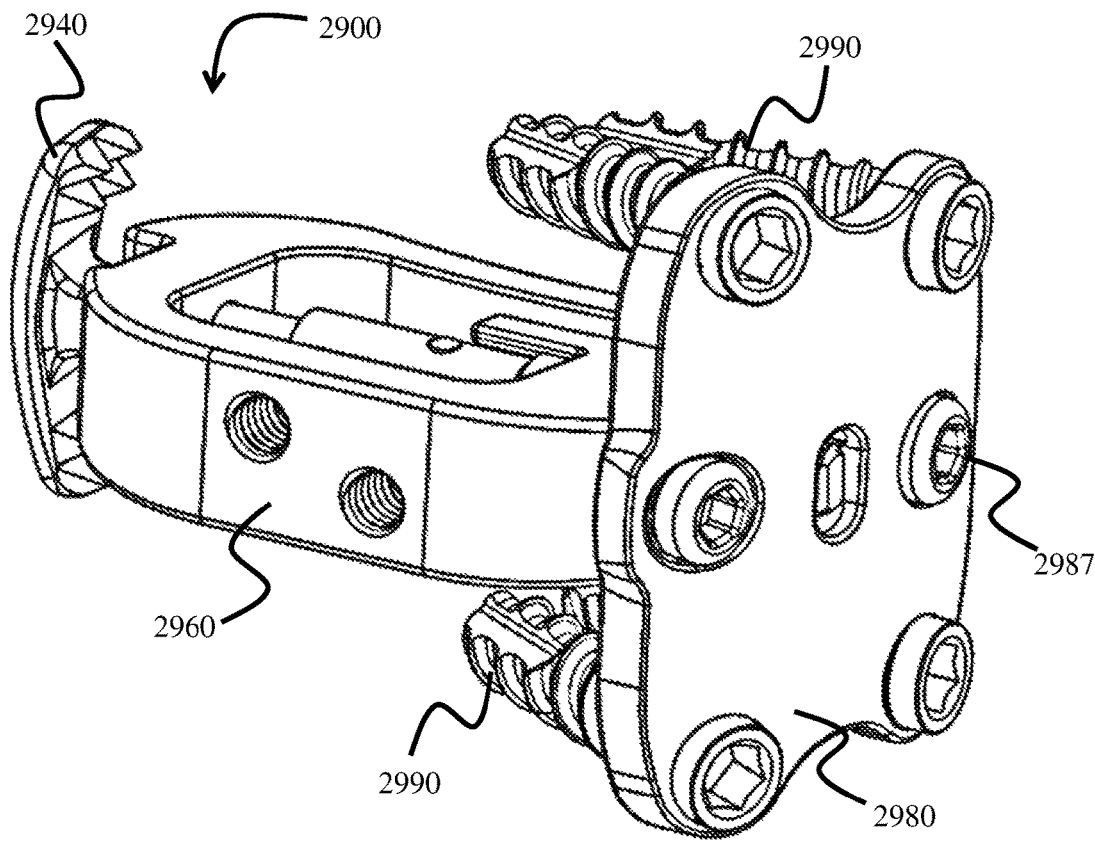
FIGS. 29A and 29B show different views of an example of the implant system.
Figure 29B:
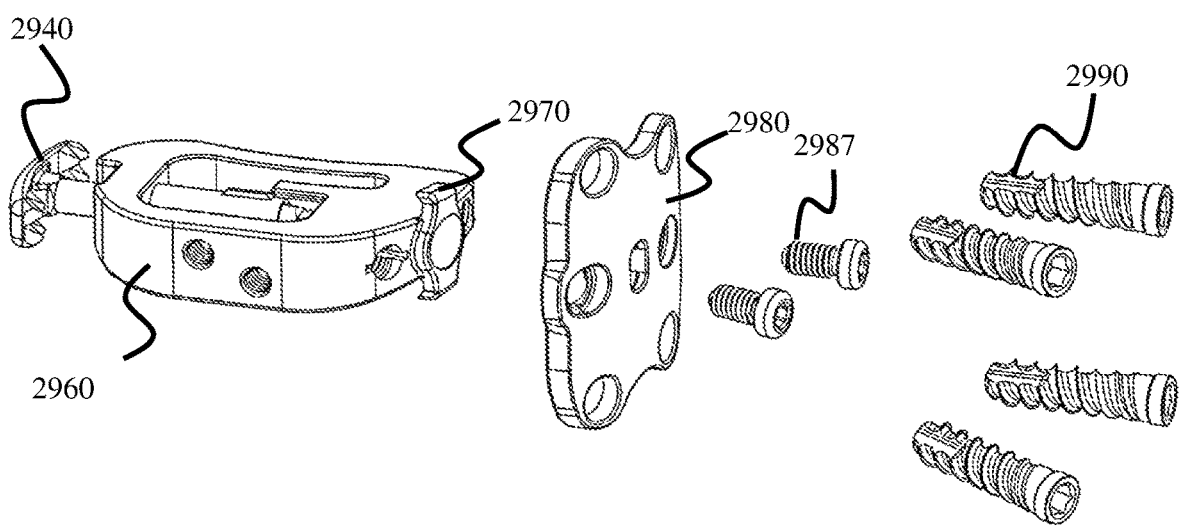
Figure 30A:
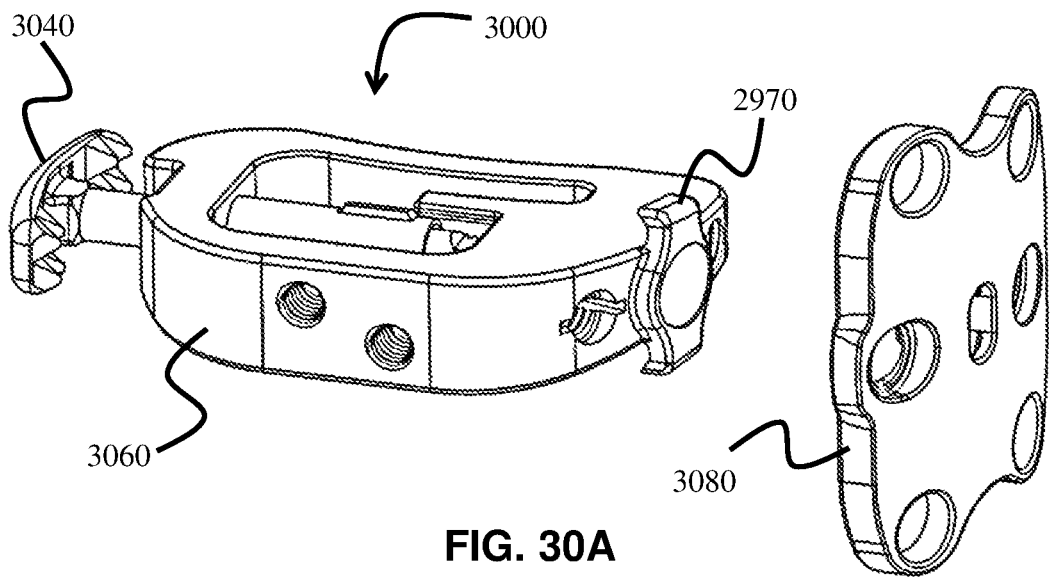
FIGS. 30A and 30B show different views of an example of components of the implant system.
Figure 30B:
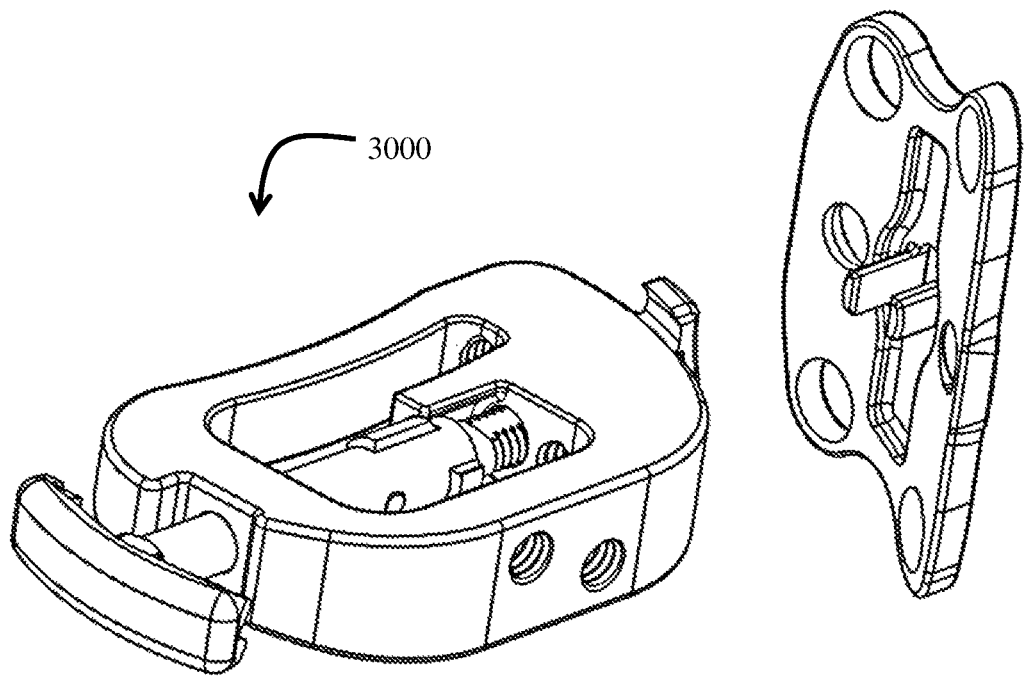

FIGS. 29A and 29B show different views of an example of the vertebral implant system 2900 that use bone screws as anchoring elements 2990. Illustrated are distal staple 2940, cage 2960, anchor frame 2980, anchoring elements 2990 and cage screws 2987. FIGS. 30A and 30B show different views of this example of components of the vertebral implant system 3000 showing the distal staple 3040, the cage 3060, the anchor frame 3080 and the proximal tab 2970.

Figure 31A:
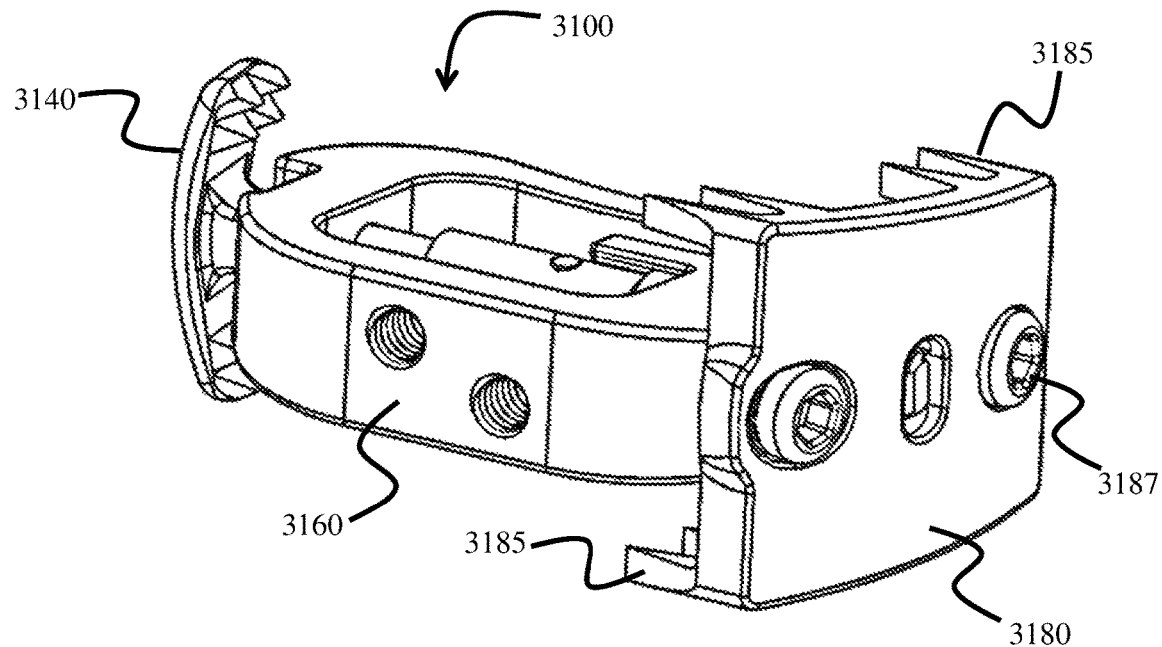
FIGS. 31A and 31B show different views of an example of the implant system.
Figure 31B:
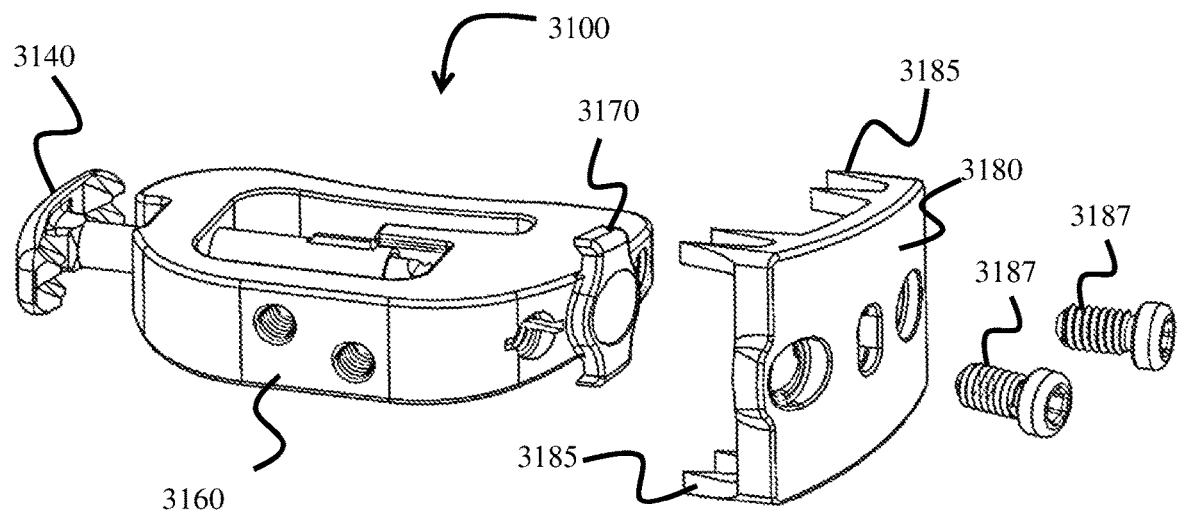
Figure 32A:
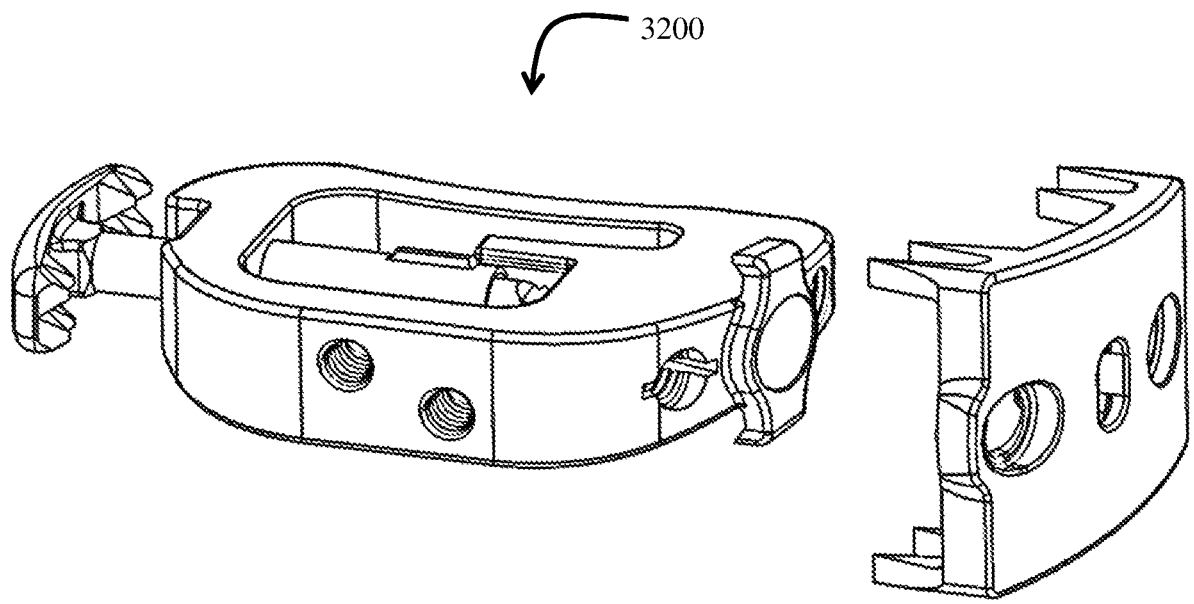
FIGS. 32A and 32B show different views of an example of components of an alternative embodiment of the implant system.
Figure 32B:
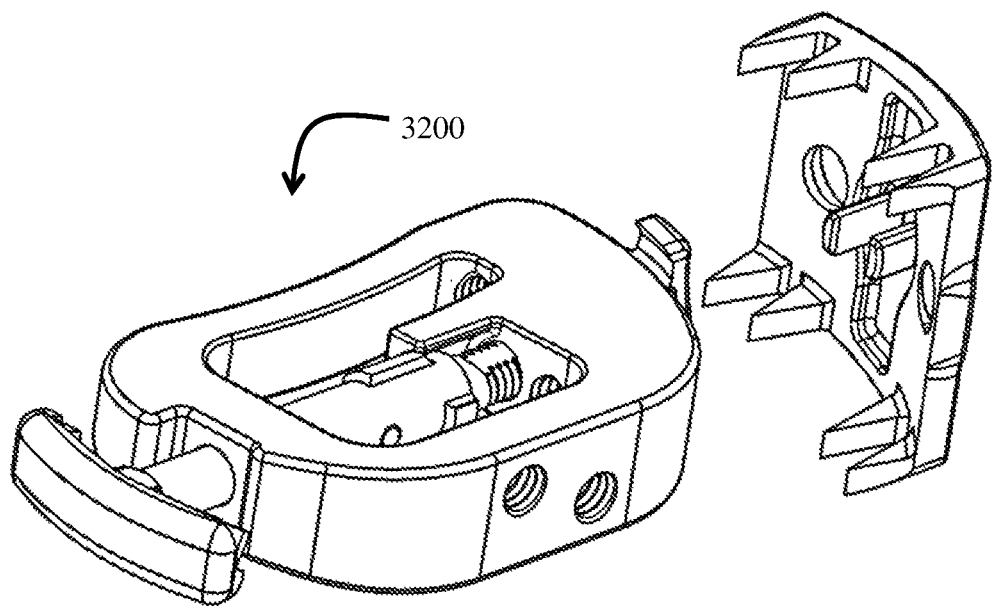

FIGS. 31A and 31B show different views of an example of the vertebral implant system 3100 that uses teeth as anchoring elements 3185. Illustrated are distal staple 3140, cage 3160, anchor frame 3180, anchoring elements 3185, proximal tab 3170 and cage screws 3187. FIGS. 32A and 32B show different views of this example of components of the vertebral implant system 3200 showing the distal staple, the cage, the anchoring elements, the anchor frame and the proximal tab.

Figure 33A:
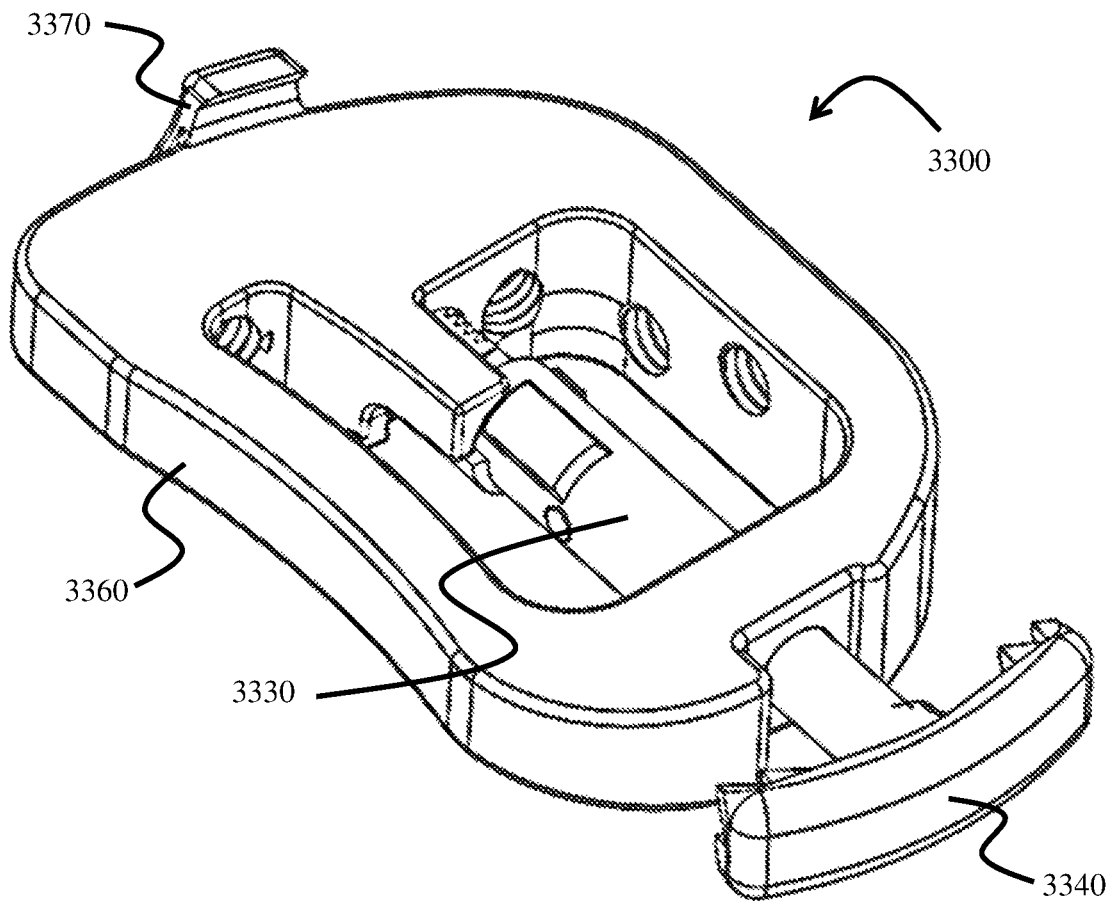
FIGS. 33A and 33B show different views of components of an example of the implant system.
Figure 33B:
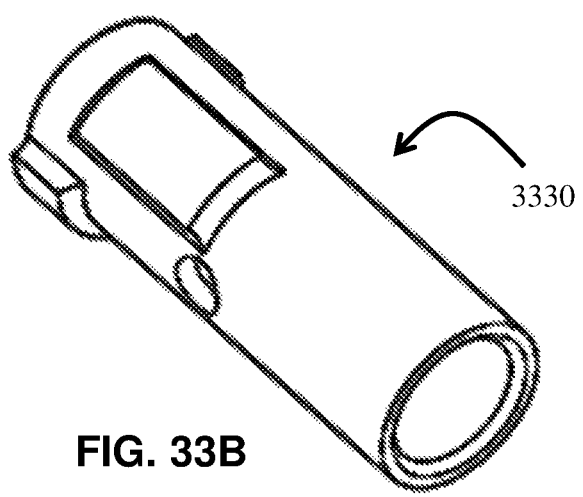

FIGS. 33A and 33B show different detailed views of components of an example of the vertebral implant system in a configuration to be deployed for implanting. FIG. 33A shows an example of the vertebral implant system 3300 having a proximal tab 3370, a cage 3360, a distal staple 3340 and locking sleeve 3330. FIG. 33B shows a detailed view of the locking sleeve 3330.

Figure 34A:
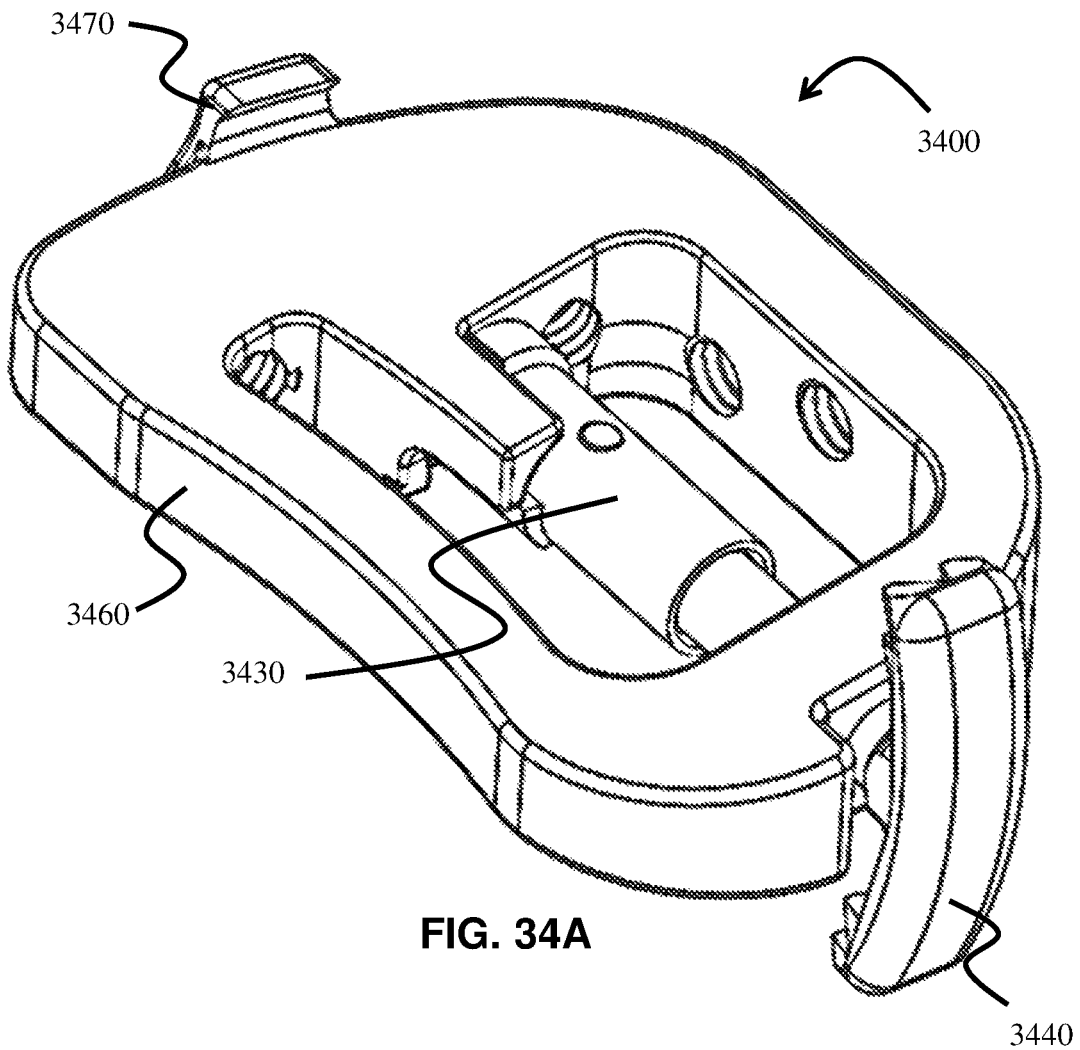
FIGS. 34A and 34B show different views of components of an example of the implant system.
Figure 34B:
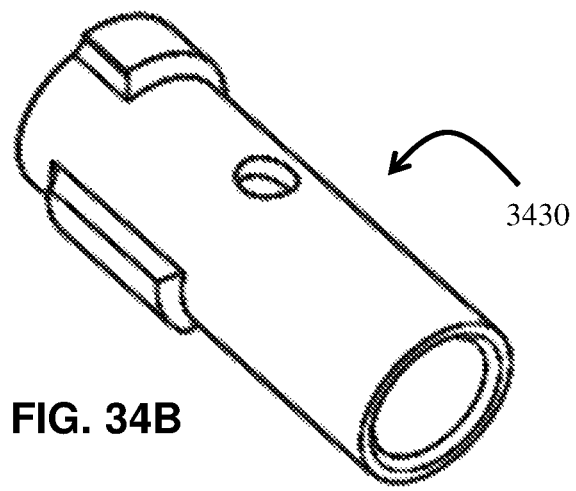

FIGS. 34A and 34B show different detailed views of components of an example of the vertebral implant system reflecting the configuration of the implant device when it is secured to the vertebral bodies. FIG. 34A shows an example of the vertebral implant system 3400 having a proximal tab 3470, a cage 3460, a distal staple 3440 and locking sleeve 3430. FIG. 34B shows a detailed view of the locking sleeve 3430.

The Implant System Used in Arthrodesis Applications:

As the above described systems and devices may be configured for use in intervertebral or intravertebral applications, the implant systems may be used to fuse opposing bones in other body joints in applications such as an arthrodesis procedure.

Figure 35A:
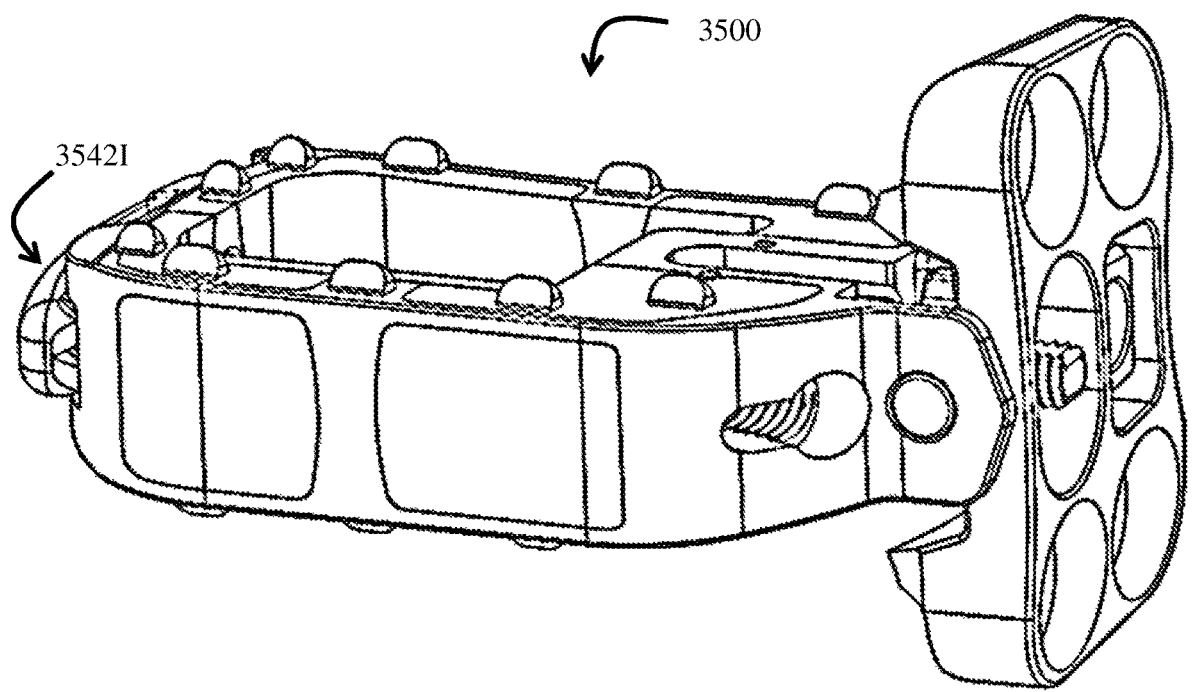
FIGS. 35A-35G show an example of an implant system where
Figure 36A:
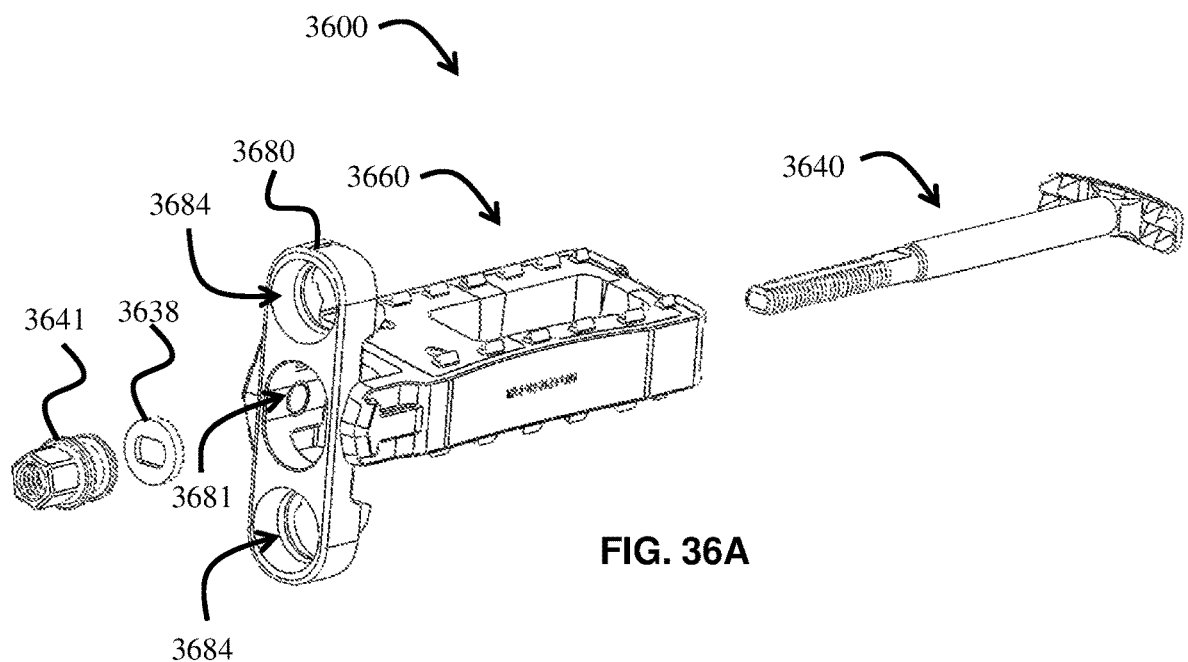

For example, referring to FIGS. 35A and 36A, the implant system may be sized and configured so that the distal staple and proximal tines secure the implant device cage between two bones of a finger or foot/ankle joint.

Similarly, referring to FIGS. 29A and 31A, the implant system may be sized and configured so that the distal staple and the bone screws (in FIG. 29A) or the teeth (in FIG. 31A) secure the implant device cage between two bones of a finger or foot/ankle joint.

Examples of Implant System Tools:

FIGS. 11A-24E, 42D-42I, 44-48 and 50A-52D show examples of tools to be used to insert examples of the implant system. These tools may be used for the implant system whether configured for use as part of an intravertebral body implant system or as part of an intervertebral body implant system. Similar tools may be modified for use with implant systems configured to be used in arthrodesis procedures for other joints throughout the body.

Figure 11A:
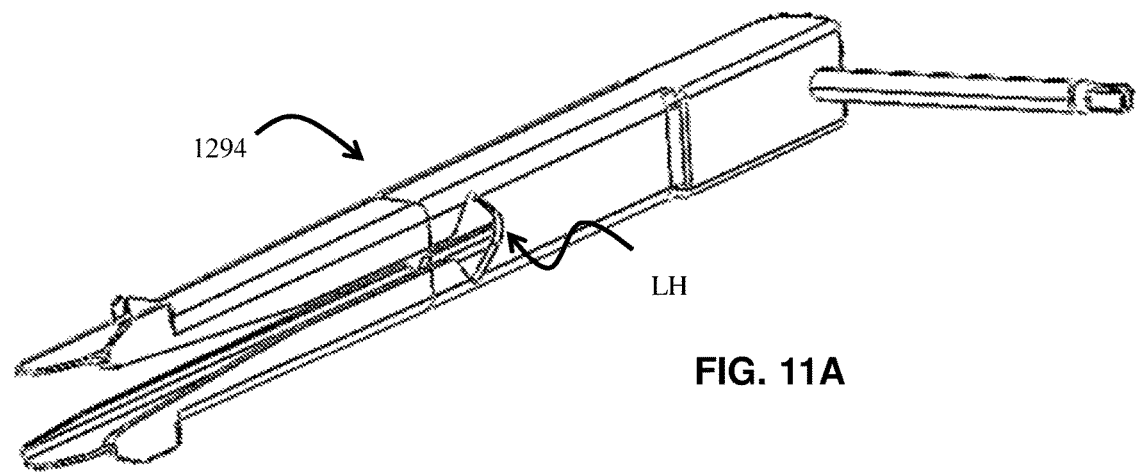
FIGS. 11A and 11B show different views of an example of an implant insertion channel guide where
Figure 11B:
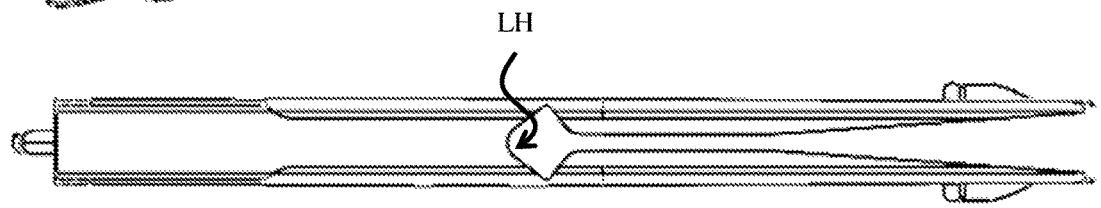
Figure 12A:
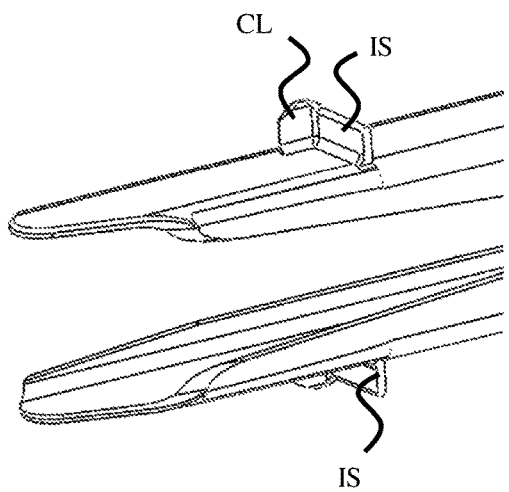
FIGS. 12A and 12B show different view of the distal end of an example of implant insertion channel guide where
Figure 12B:
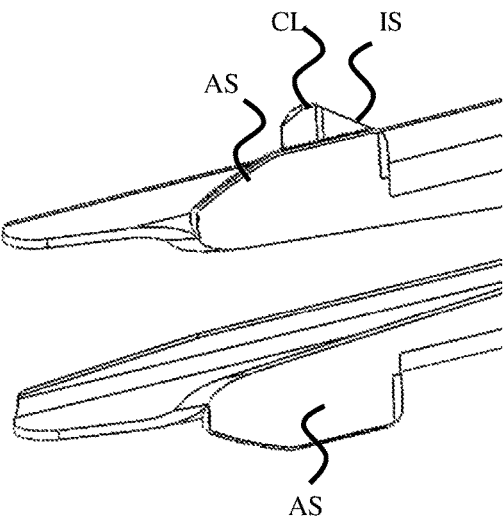

FIGS. 11A and 11B show different views of an implant insertion channel guide 1294. As shown in FIGS. 11A and 11B, the implant insertion channel guide 1294 has a living hinge LH allowing its arms to flex to a closed position if needed. FIGS. 12A and 12B show the distal ends of the implant insertion channel guide 1294 with features to properly position and prevent migration of the channel guide and implant device during insertion of the implant device. These features include a cleat CL to rest against the sidewalls of the bone(s) and prevent anterior migration of the distal end of the channel guide, an insertion stop IS to rest against the sidewalls of the bone(s) and stop insertion of the channel guide, and an anterior stop AS to rest against the sidewalls of the bone(s) and prevent posterior migration of the distal end of the channel guide. FIG. 12A shows an example with these features configured for an interbody implant procedure and FIG. 12B shows an example with the guide features configured for an intrabody implant procedure.

Figure 13A:
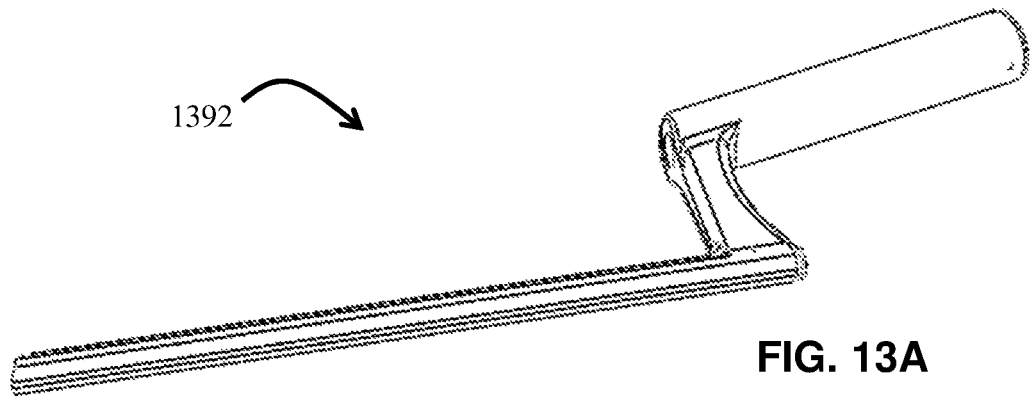
FIGS. 13A-13C show different views of an example of an insertion handle assembly where
Figure 13B:
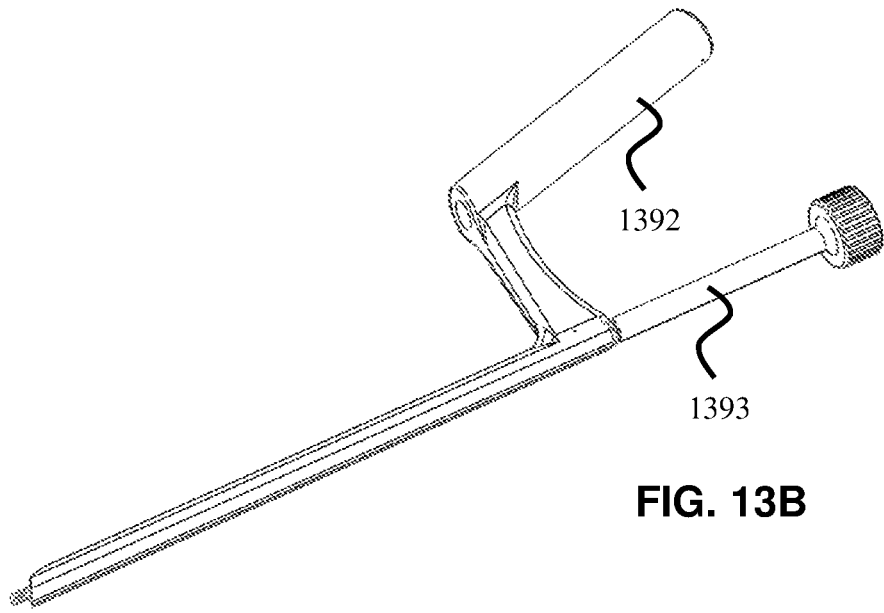
Figure 13C:
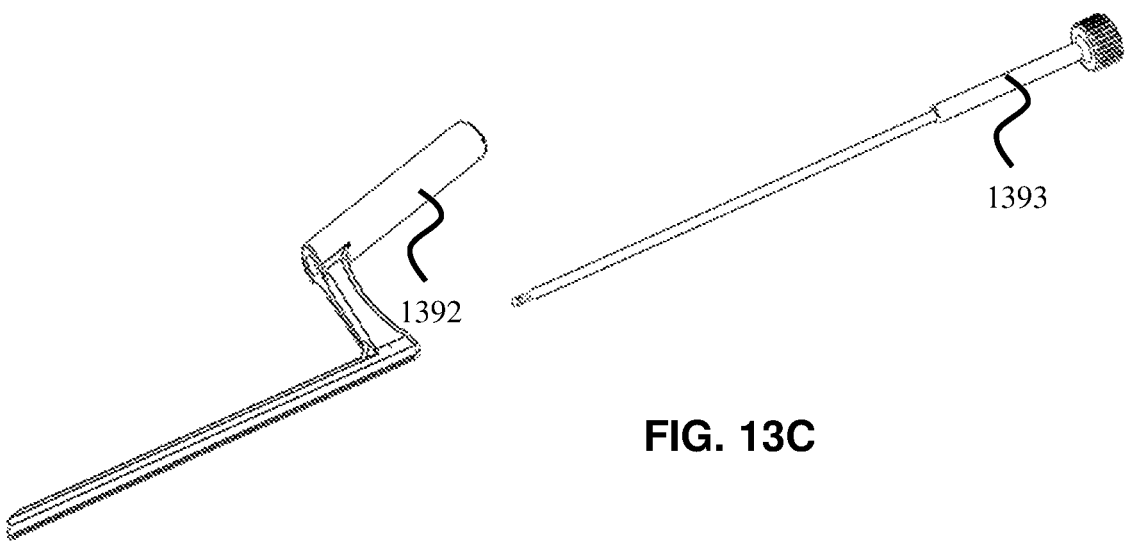

FIGS. 13A and 13B show different views of an insertion handle assembly 1392 and locking rod 1393, for example for use in an ATP procedure, and FIG. 13C shows a partially exploded view of the insertion handle assembly 1392 and locking rod 1393.

Figure 14:
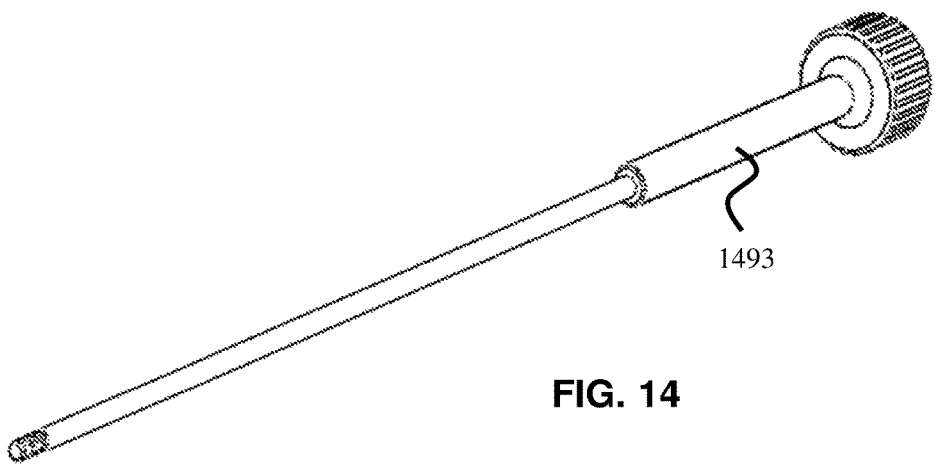
FIG. 14 shows an example of a threaded locking rod.

FIG. 14 shows one example of a modified locking rod 1493 with a knob on its proximal end.

In some embodiments, the locking rod may function as a guide rod to guide multiple tools when using the disclosed implant system. The locking rod may also be hollow and may be used as a tube to deliver material such as bone graft material to the implant device.

Figure 15:
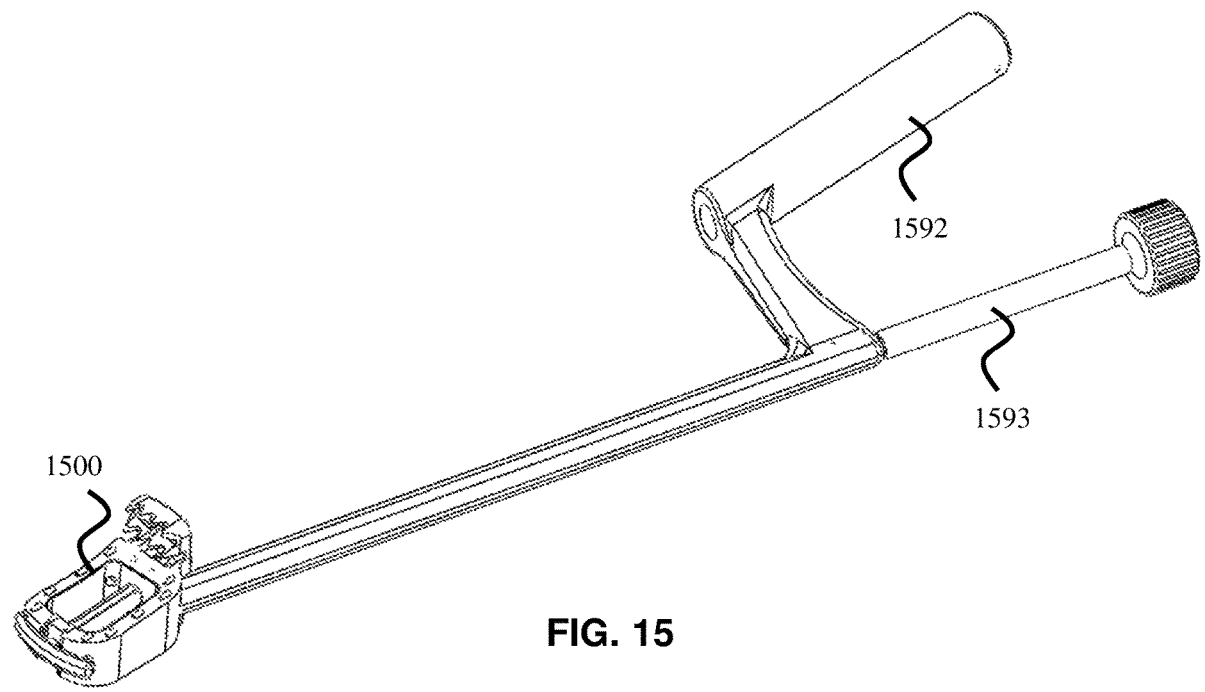
FIG. 15 shows a view of a threaded locking rod received in the insertion handle assembly and coupled to an implant device.

FIG. 15 shows a view of the threaded locking rod 1593 received in the bore of the insertion handle assembly 1592 and coupled to an implant device 1500.

Figure 16A:
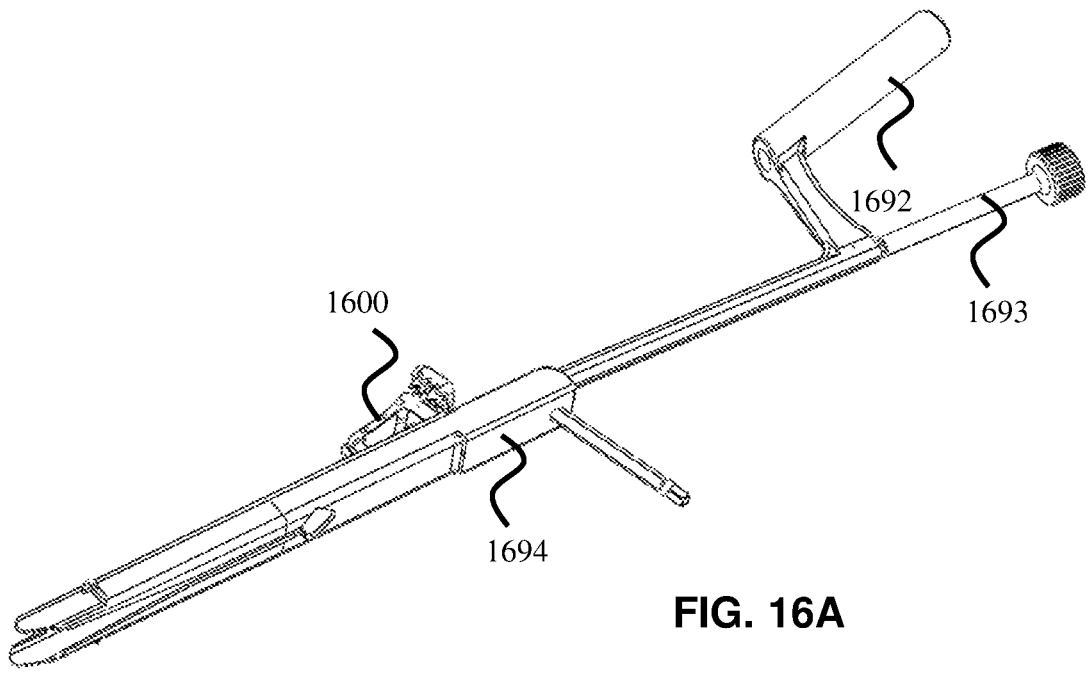
FIGS. 16A and 16B show views of an example of an implant device, an insertion handle assembly in the insertion channel guide where
Figure 16B:
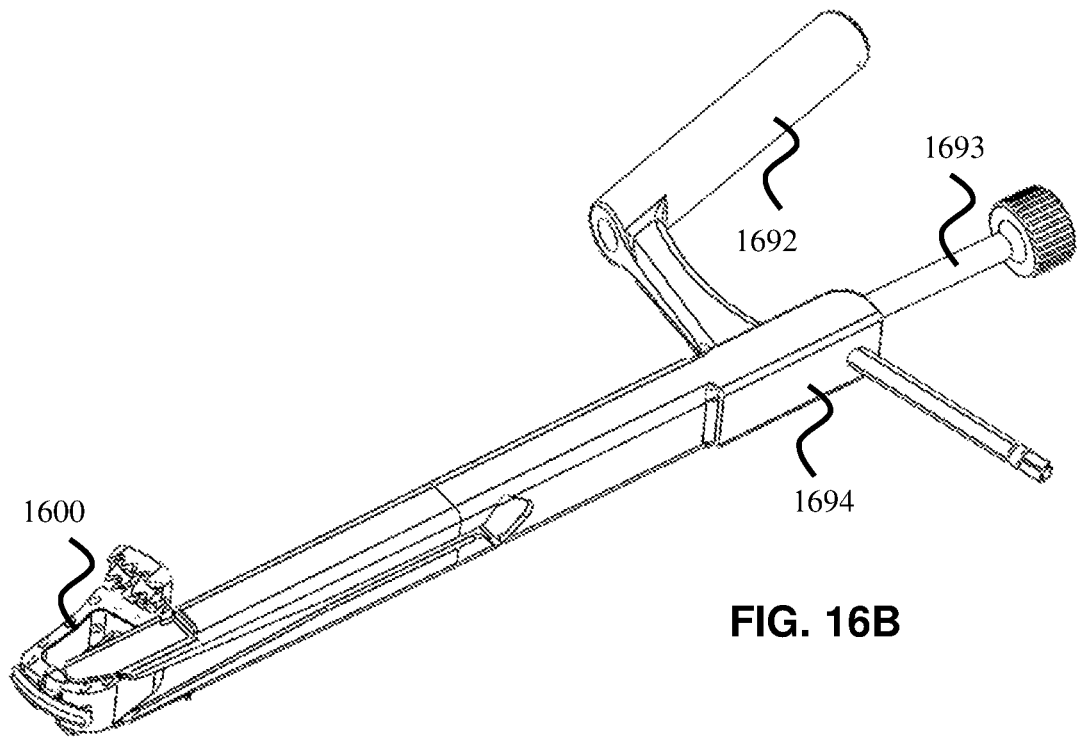

FIGS. 16A and 16B show views of the implant device 1600 and insertion handle assembly 1692 with the locking rod 1693 in the insertion channel guide 1694. FIG. 16A shows the insertion handle assembly 1692 early in the insertion and FIG. 16B shows the insertion handle assembly 1692 and implant device 1600 close to an implant position.

Figure 17:
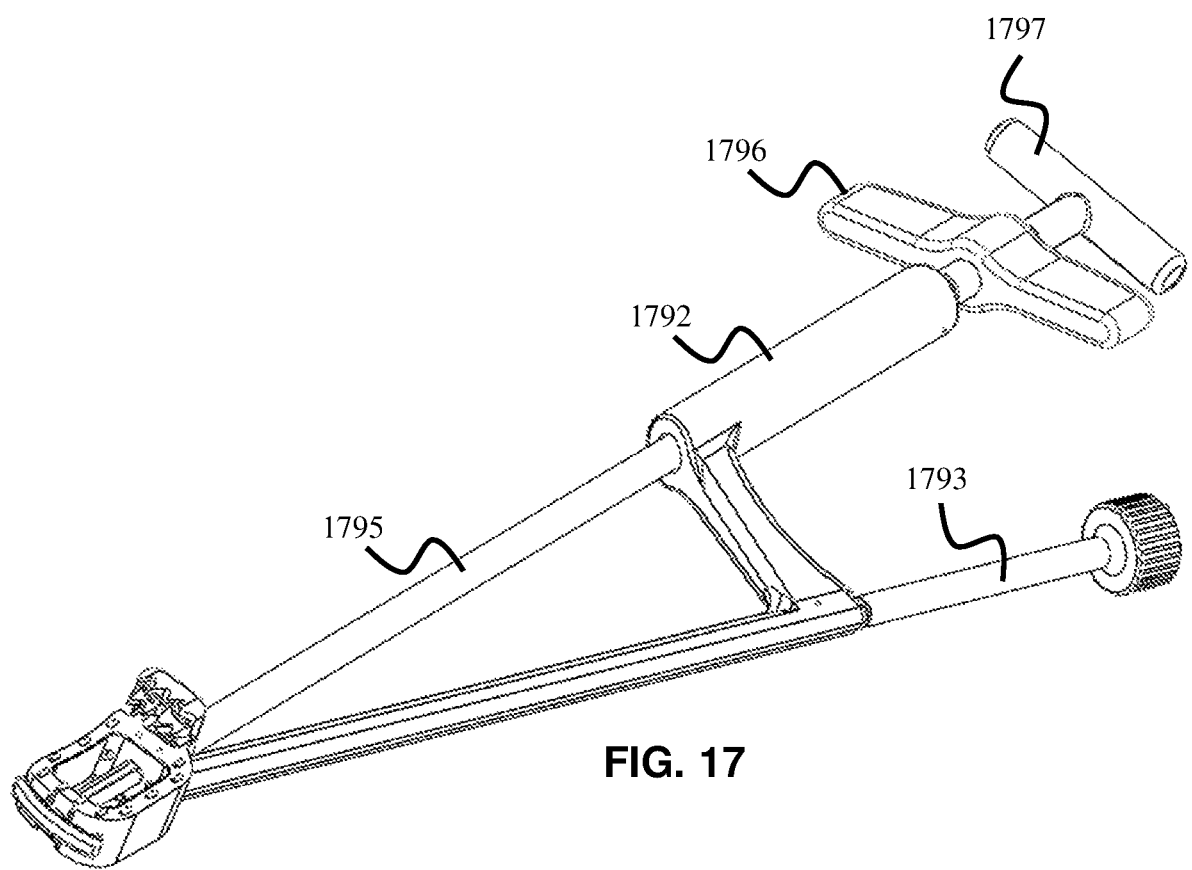
FIG. 17 shows an example of the staple drive handle assembly, the threaded locking rod and the implant device coupled to the insertion handle assembly.

FIG. 17 shows the staple drive handle assembly 1795 and locking rod positioned 1793 in the insertion handle assembly 1792.

This example shows a staple drive handle assembly 1795 having multiple handles coupled to multiple engagement elements. For example, one handle 1797 may be coupled to an inner rod to engage the engagement portion of the staple shaft and another handle 1796 may be coupled to an outer rod to engage the coupling element, or nut. In this example, one handle may turn the inner rod and the staple and the other handle may turn the coupling element, such as the nut, to extend and retract the staple from the cage.

Figure 18A:
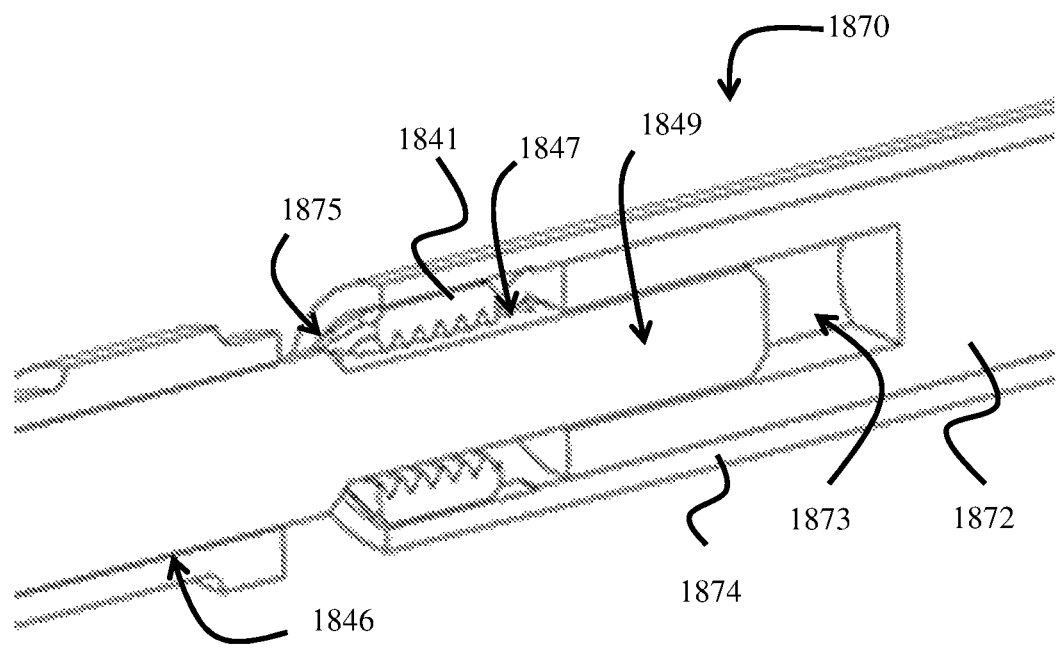
FIGS. 18A and 18B show elements of an example of the staple drive handle assembly where
Figure 18B:
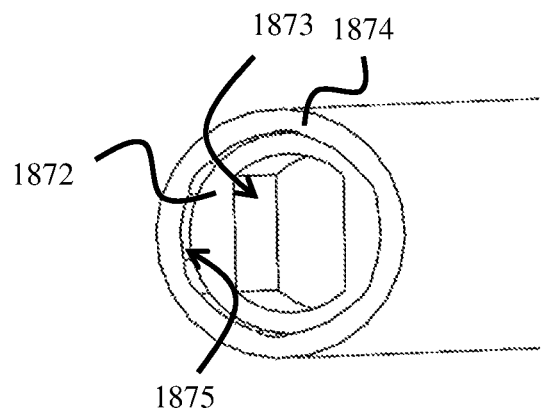

FIGS. 18A and 18B show elements of a staple drive handle assembly 1870 as part of an example engagement tool. In the example shown, the staple drive handle assembly 1870 has an inner drive rod 1872 and an outer drive rod 1874 to engage portions of the staple shaft 1846. FIG. 18A shows an end view of the staple drive handle assembly 1870 and how the drive rods, as engagement tools, engage the staple shaft 1846. The inner drive rod 1872 fits within the outer drive rod 1874 and its distal end is configured to engage the engagement portion 1847 of the staple shaft. The mated coupling of the inner drive rod 1872 and the shaft engagement portion at 1873 with the staple shaft engagement portion 1847 allows the staple shaft 1846 to be rotated so that the staple can be aligned and positioned in the deployed position. In this example, the staple shaft engagement portion 1847 is a portion of the staple shaft with flats and the shaft engagement portion 1873 of the inner drive rod 1872 is a mating recess with flats. The outer drive rod 1874 is configured to engage the coupling element. As shown, the engagement is the outer drive rod with the outer surface of a threaded nut 1841 that mates with the coupling portion, here a threaded portion, of the staple shaft 1846. The coupling of the outer drive rod 1874 and the nut 1841 at the nut engagement portion 1875 allow the nut 1841 to be rotated by the outer drive rod 1874 when the staple drive handle is rotated. This rotation and the mated threading of the staple shaft 1846 and nut 1841 allows the staple shaft 1846 to be slidably extended, rotated and retracted in relation to the cage within the cage through bore. The inner drive rod 1872 and outer drive rod 1874 may be frictionally engaged to allow a turn of the staple drive handle to turn both drive rods until the staple shaft 1846 positions the staple in the "deployed" position. This positioning may be assisted by the stops and keys on the staple shaft and/or locking sleeve and/or the cage that can be configured to stop rotation of the staple shaft 1846 when the staple is in the deployed position. Once the staple is in the deployed position, the outer drive rod 1874 may still be turned by the staple drive handle to turn the nut 1841 and retract the shaft 1846 and staple. FIG. 18B shows an example of the end of the staple drive handle assembly with the inner drive rod with an engagement portion 1873 shaped to mate with the coupling portion 1849 of the staple shaft 1846 and the outer drive rod having an engagement portion 1875 shaped to mate with the exterior surface of the nut 1841.

As shown in FIG. 18A, in some embodiments, the staple drive handle assembly 1870 may be configured to further assist in the deployment of the staple. As shown, the distal end of the staple drive handle assembly 1870 may be configured to push on an element, such as the nut 1841, to push the shaft 1846 and the staple away from the cage and outside of the osteotomy so that it can be rotated and retracted to secure the cage to the vertebral body. As shown, the configuration may include using the distal end of the inner drive rod 1872 to push on the nut 1841 which pushes the staple shaft 1846 and staple further outside of the cage. The movement of the staple and shaft 1846 may be limited in this configuration by a physical limitation. For example, as shown, the distal end of the outer drive rod 1874 may be physically limited to move only a certain distance by hitting a physical stop such as the proximal end of the sleeve or other component. In some embodiments, the rotation and the threading of the staple shaft 1846 and nut 1841 allows the staple shaft 1846 to be extended in a distal direction away from the cage.

Figure 19A:
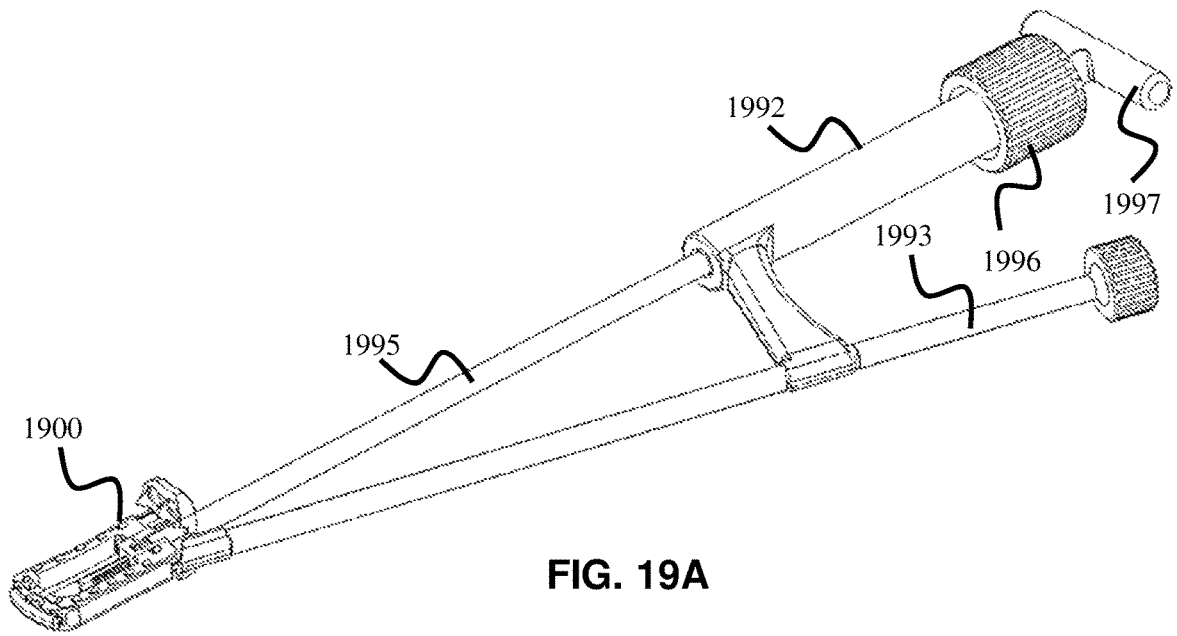
FIGS. 19A and 19B show different views of an example of an insertion handle assembly with a threaded locking rod, staple drive handle assembly and implant device positioned for use in anterior to psoas (ATP) implant procedure where
Figure 19B:
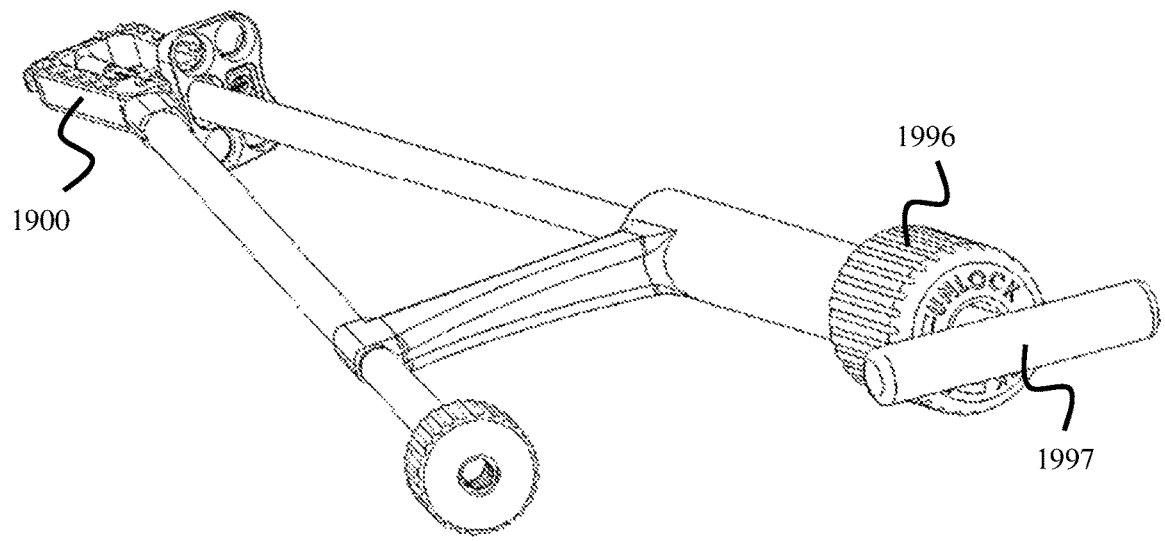

FIGS. 19A and 19B show different views of an example of an insertion handle assembly 1992 with a threaded locking rod 1993, staple drive handle assembly 1995 and implant device 1900 positioned for use in anterior to psoas (ATP) implant procedure. FIG. 19A shows a top perspective view and FIG. 19B shows a perspective view from the proximal end. In this example, the inner rod may be coupled to a handle 1997 to move the engagement portion of the staple shaft and the outer rod may be coupled to a knob 1996 to engage the coupling element.

Figure 20:
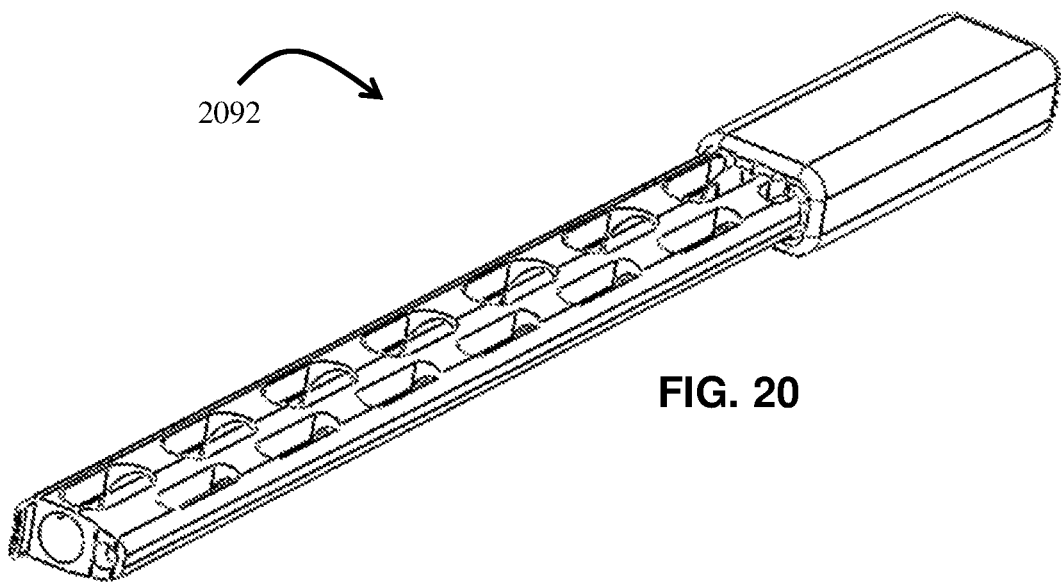
FIG. 20 shows an example of an insertion handle assembly for use in a lateral implant procedure.

FIG. 20 shows an example of an insertion handle assembly 2092 for use in a lateral implant procedure.

Figure 21:
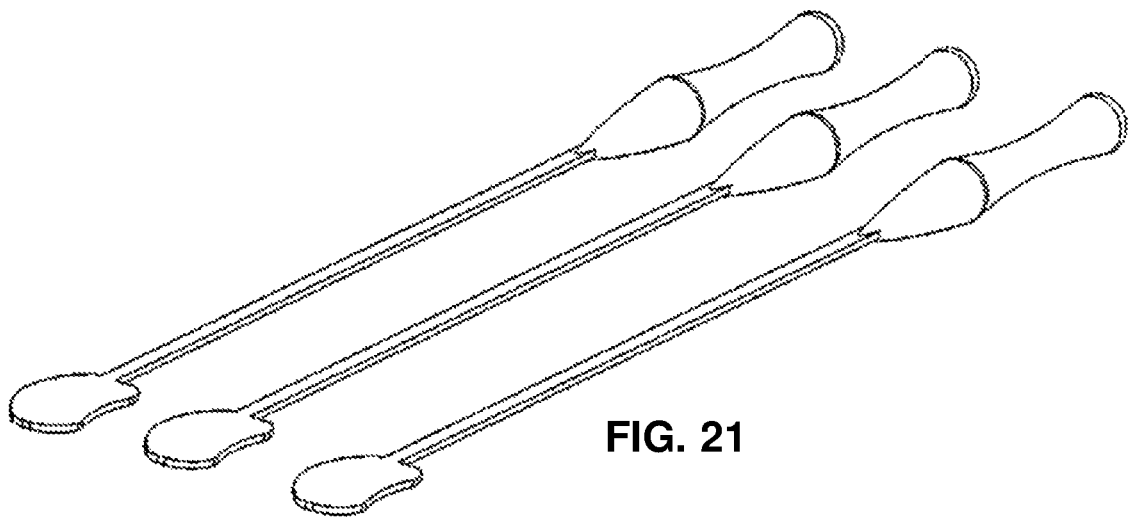
FIG. 21 shows examples of footprint sizer tools.

FIG. 21 shows an example of footprint sizer tools. These vertebral footprint sizer tools are used as templates to place on or near the vertebral body to determine the size of the implant device to be used.

Figure 22:
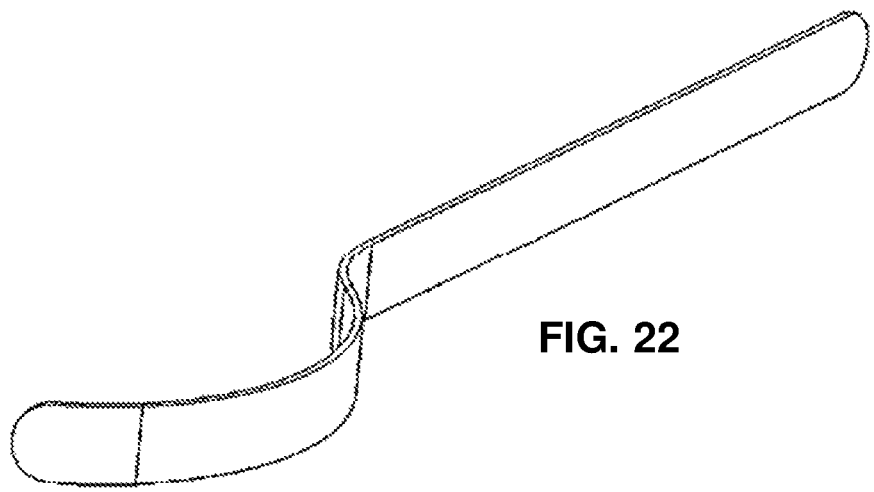
FIG. 22 shows an example of a far side retractor tool.

FIG. 22 shows an example of a far-side retractor tool. The far-side retractor tool may be a malleable tool configured to be positioned around the vertebral body and protect sensitive tissue before and/or during the procedure.

Figure 23A:
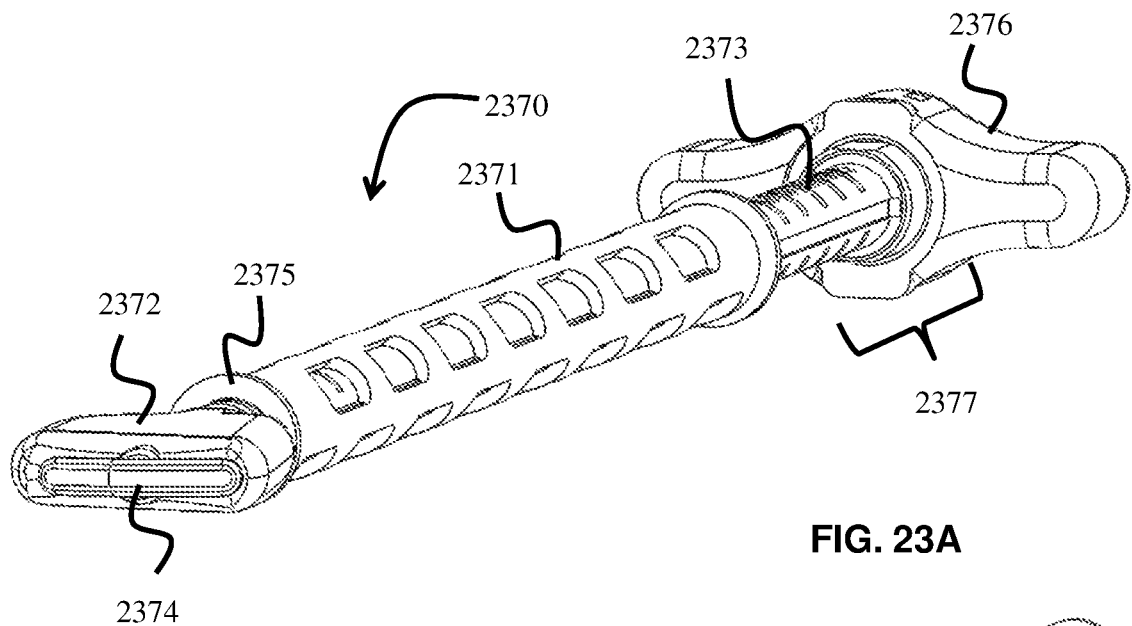
FIGS. 23A and 23B show different views of an example of a far-side elevator tool where
Figure 23B:
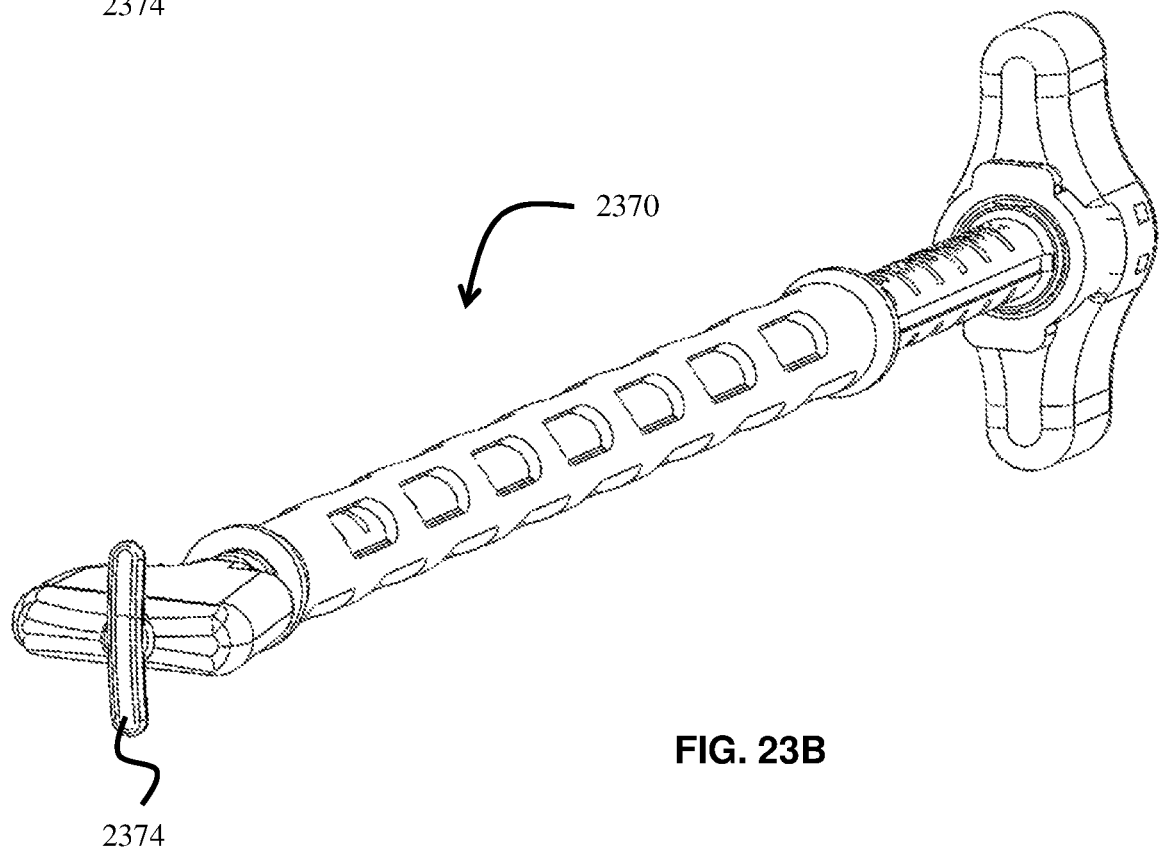

FIGS. 23A and 23B show different views of an example of a far-side elevator tool 2370. The far-side elevator tool 2370 generally is used to prepare the insertion site for the implant device. The far-side elevator tool 2370 comprises a shell 2372, a paddle 2374, an outer sleeve 2371, and inner shaft 2373 and a paddle assembly 2376. The outer sleeve is coupled to the shell 2372 to control its position. A paddle shaft (not shown) is coupled to the paddle 2374 and the paddle handle 2376 to allow the paddle handle 2376 to control the rotational position of the paddle 2374 (see FIG. 23B). The inner shaft 2373 is received in the outer sleeve 2371 and allows for the extension of the inner shaft 2373 in an out of the outer sleeve 2371. The inner shaft 2373 is configured to have an exposed measuring portion 2377 beyond the outer sleeve 2371. The measuring portion 2377 is marked with calibrations so that if an outer sleeve stop 2375 is pushed up against a vertebral body, the calibration identifies the distance from the edge of the vertebral body to a tool component such as the paddle 2374 (see FIGS. 24D and 24E). This distance is used to ensure the paddle 2374 is positioned properly when it is rotated to clear obstructions on the far-side of the vertebral body.

Referring to FIGS. 24A-24E, the paddle handle 2476 is configured to lock relative to the outer sleeve 2471 and the inner shaft 2473 with a shaft lock 2478. The shaft lock 2478 may be disengaged by pulling the handle portion of the paddle handle 2476 away from the inner shaft 2473, opening a lock gap 2479 to allow the handle portion to rotate and rotate the paddle.

Figure 50A:
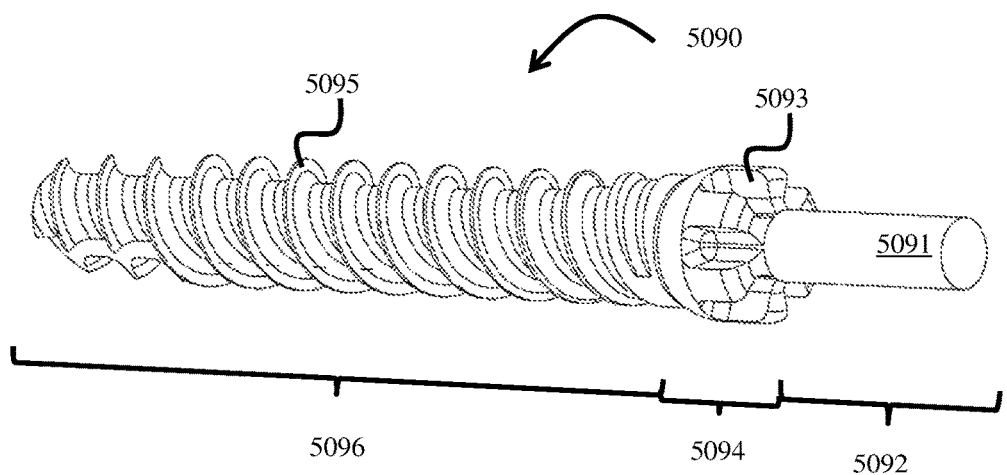
FIGS. 50A and 50B illustrating an example of a tipped bone screw with FIG. 50A showing the tipped bone screw and FIG. 50B showing a screw driver engaged with a tipped bone screw.
Figure 50B:
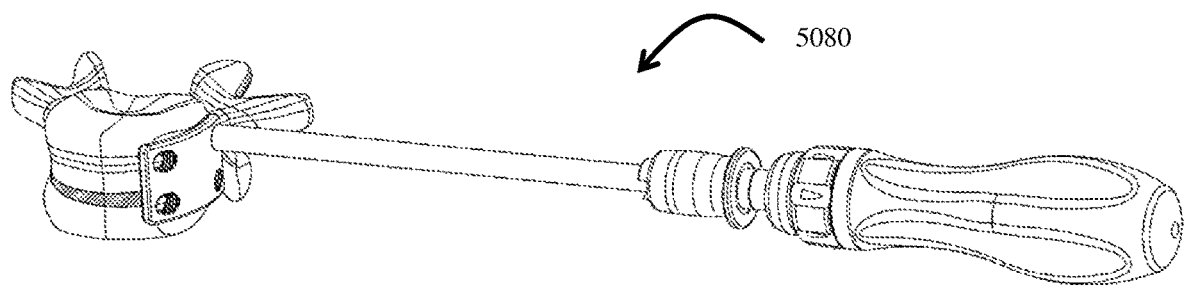

In some embodiments, the bone screws and the anchor frame are secured to each other and the bone through the use of a screw plate alignment system. The screw plate alignment system may comprise elements to frictionally engage and couple the tipped bone screw to the anchor frame. FIGS. 50A-52D illustrate an example of a screw driver, a lock driver and other components that can be used with the tipped bone screw to provide the screw plate alignment system. As part of a screw plate alignment system, FIGS. 50A and 50B illustrate examples of a tipped bone screw with FIG. 50A showing the tipped bone screw and FIG. 50B showing a screw driver 5080 engaged with a tipped bone screw to anchor the tipped bone screw in the vertebral body. Referring to FIG. 50A which shows a tipped bone screw 5090 suitable for providing the features of staple tines for the implant system. The tip portion 5092 of the bone screw is configured to have a surface 5091 that can be frictionally or mechanically engaged by the securing element. The tip portion 5092 may be configured to have features that facilitate this frictional engagement with other screw plate alignment system components. For example, the tip portion 5092 may have a frictional surface, roughened surface or a radially ribbed surface. The bone screw 5090 may have an engagement portion 5094 to mate with a tool, such as a screw driver, to turn and insert the bone screw 5090 into the vertebral body. The engagement portion 5094 of the tipped bone screw 5090 may comprise teeth 5093 to mate with teeth on the screw driver tool. The bone screw 5090 may have a threaded portion 5096 with threads 5095 to allow the bone screw 5090 to be driven into and secured to the vertebral body. The threaded portion 5096 is similar to common bone screws configured to secure the screw to the bone. FIG. 50B shows an example of a screw driver 5080 with a handle and a shaft tipped with an engagement portion to mate with the engagement portion of the tipped bone screw.

Figure 51A:
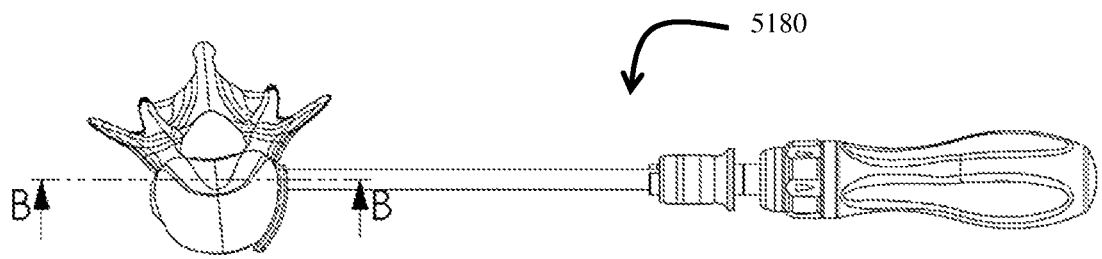
FIGS. 51A-51F illustrate an example of a screw driver with FIG. 51A showing the screw driver engaged with a tipped bone screw, FIG. 51B showing a cross section of the screw driver engaged with the tipped bone screw in a vertebral body, FIG. 51C showing the screw driver positioned to be engaged with a tipped bone screw, FIG. 51D showing details of the screw driver and the tipped bone screw, FIG. 51E showing another view of the screw driver positioned to be engaged with a tipped bone screw and FIG. 51F showing another view of details of the screw driver and the tipped bone screw.
Figure 51B:
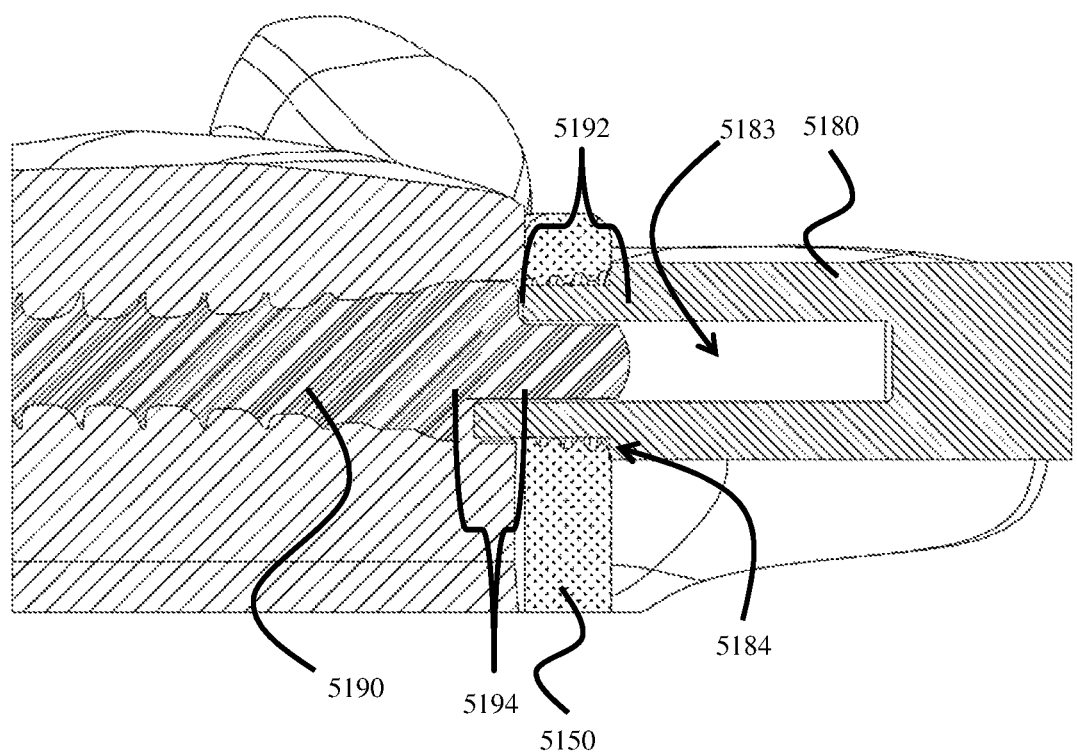

FIGS. 51A-51F illustrate an example of a screw driver. FIG. 51A shows the screw driver 5180 engaged with a tipped bone screw in a vertebral body. FIG. 51B illustrates a cut away profile B-B of FIG. 51A showing an upper staple with tipped bone screw 5190 functioning as a staple tine. As detailed in FIG. 51B, the bone screw is a tipped bone screw 5190 with the tip portion of the tipped bone screw configured to engage a hollow tip of the bone screw driver 5180. The tip portion 5192 is configured to extend beyond the engagement portion 5194 of the tipped bone screw 5190 and be received in a hollow tip 5183 of the bone screw driver 5180. The tip portion 5192 is also configured to secure the tipped bone screw 5190 to a staple plate or directly to an anchor frame 5150 through a screw plate alignment system. FIG. 51B also shows the forward portion of the screw driver 5180 also has a drive stop 5184 that limits the driving of the tipped bone screw 5190.

Figure 51C:
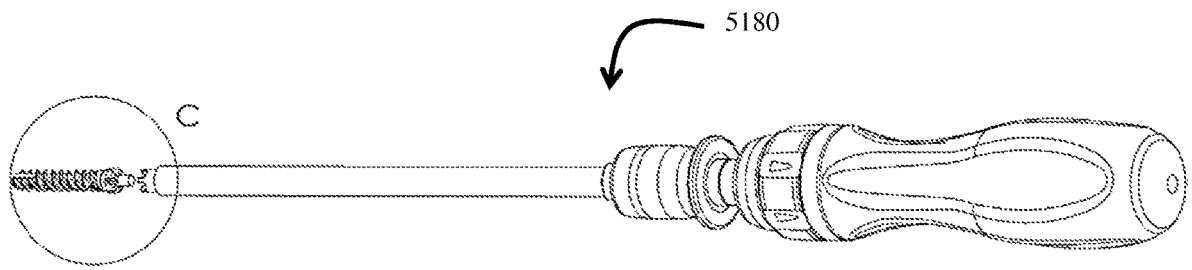
Figure 51D:
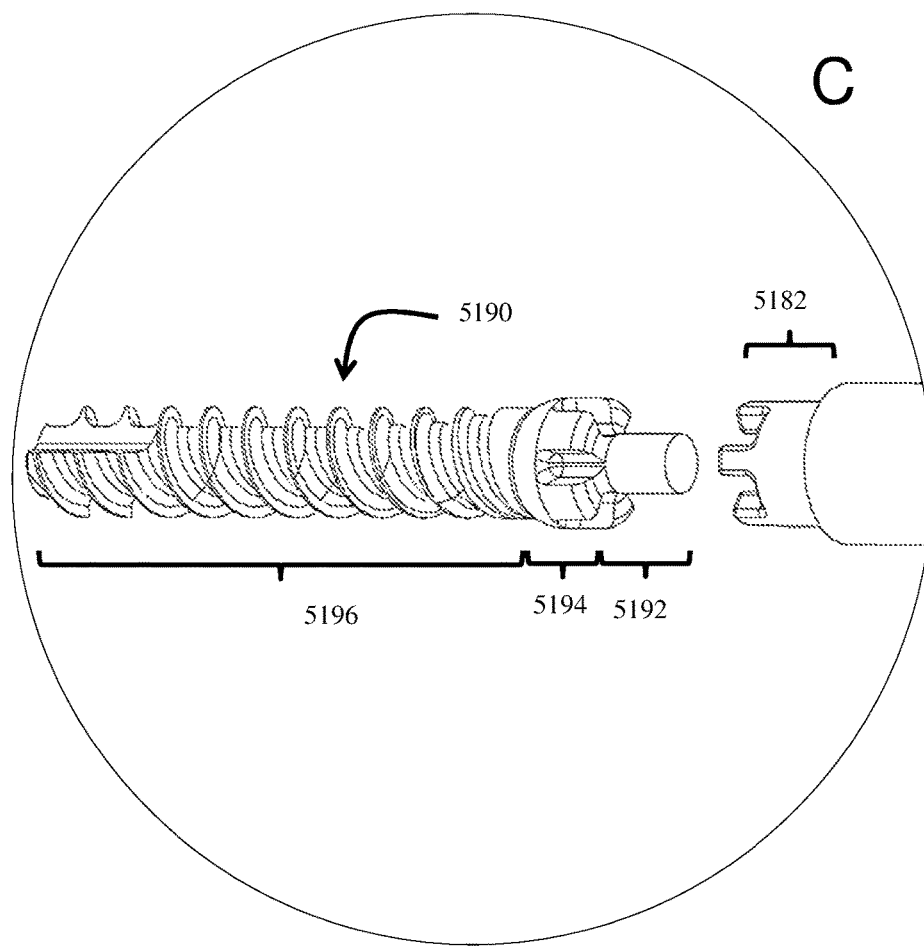
Figure 51E:
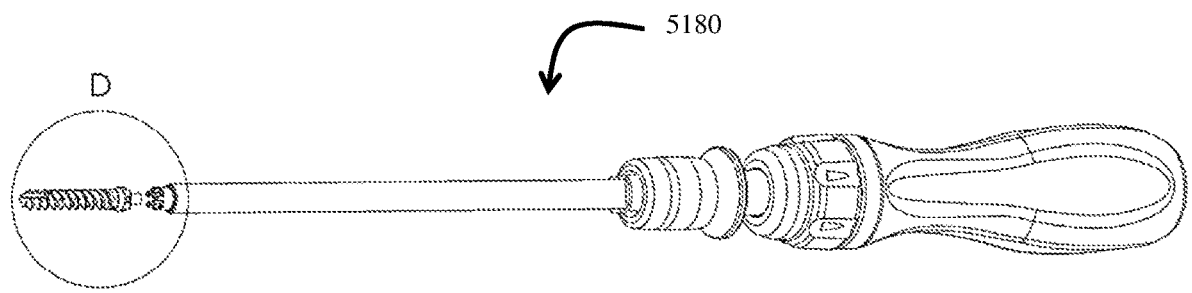
Figure 51F:
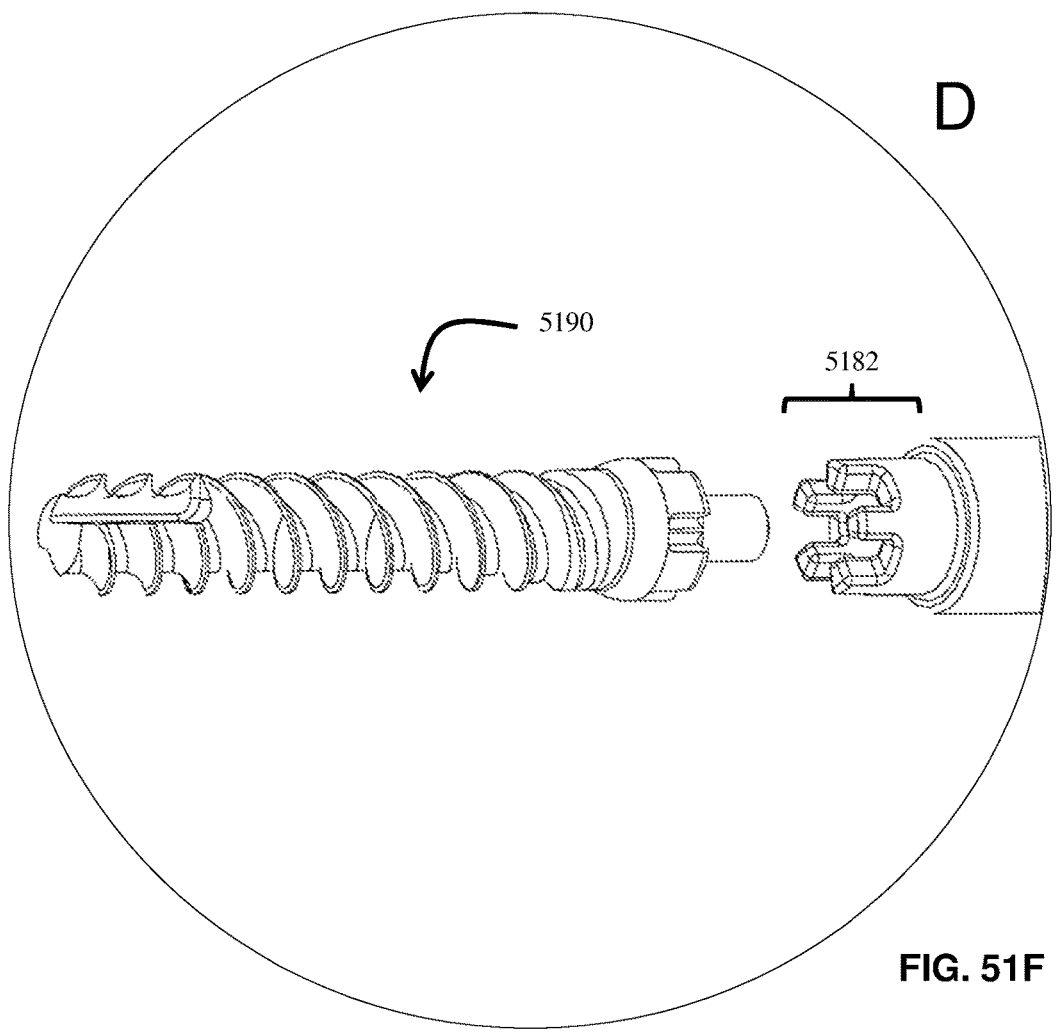

FIG. 51C shows the screw driver positioned to be engaged with a tipped bone screw. FIG. 51D shows details of the screw driver and the tipped bone screw 5190 showing its threaded portion 5196, the engagement portion 5194, the tip portion 5192 and the engagement portion 5182 of the screw driver. As shown, the tip of the tipped bone screw driver 5180 is configured to receive the tip portion of the tipped bone screw 5190 and engage the engagement portion 5194 so that the tipped bone screw 5190 may be turned and driven into the bone. FIG. 51E shows another view of the screw driver 5180 positioned to be engaged with a tipped bone screw 5190 and FIG. 51F showing another view of details of the screw driver engagement portion 5182 and the tipped bone screw 5190.

Figure 52A:
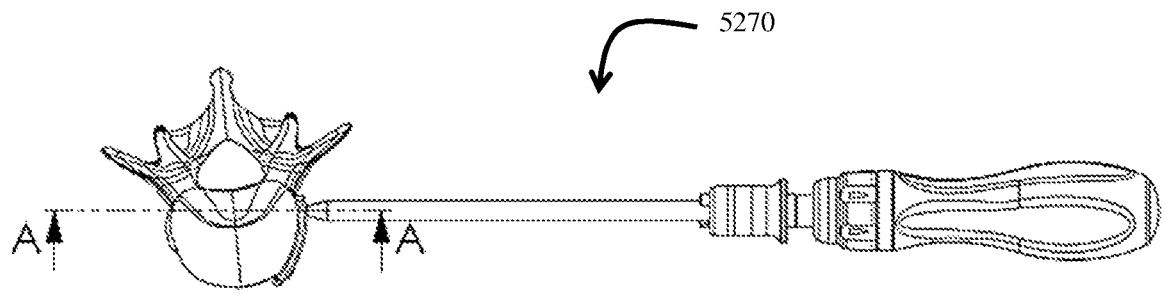
FIGS. 52A-52D illustrate an example of a lock driver with FIG. 52A showing the lock driver engaged with a tipped bone screw, FIG. 52B showing a cross section of the lock driver engaged with the tipped bone screw in a vertebral body, FIG. 52C showing an exploded view of the lock driver and securing element and FIG. 52D showing details of the lock driver and the securing element.
Figure 52B:
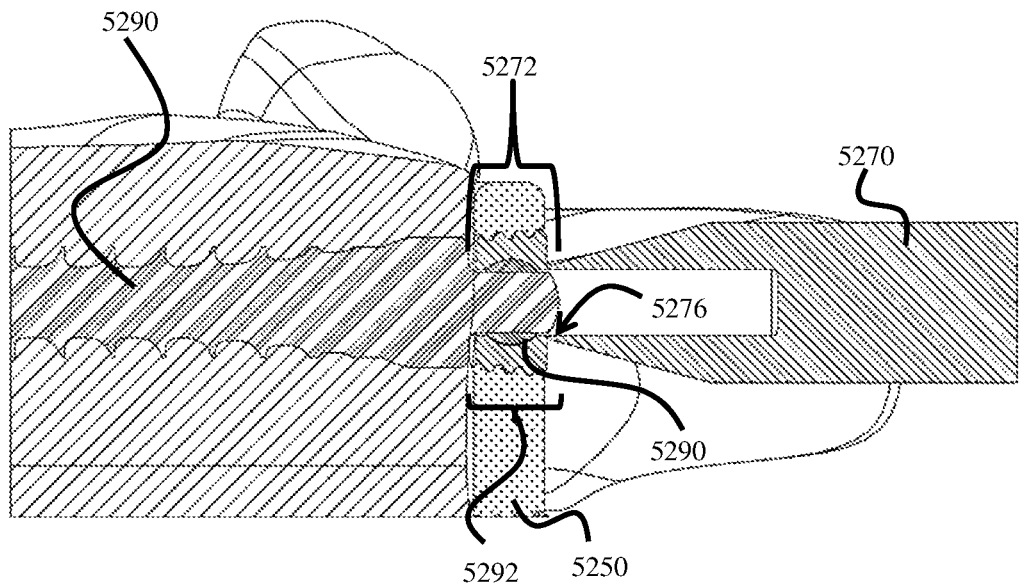

FIG. 52A shows a lock driver 5270 engaged with a tipped bone screw in a vertebral body. FIG. 52B shows a cut-away portion A-A of FIG. 52A showing a screw plate alignment system comprising the tip portion 5292 of the bone screw 5290, the interior surface of the through hole through the plate 5250, a locking element 5272, and a securing element 5279. As shown, the tip of the lock driver 5270 is configured with the locking element 5272. Generally, the locking element 5272 functions to frictionally lock the securing element 5279 around the tip portion 5292 of the bone screw 5290 and hold the securing element 5279 and tip portion 5292 in the through hole of the plate 5250. Also shown is the securing element 5279 positioned within the locking element 5272 so that the securing element 5279 and the locking element 5272 can be positioned over and around the tip portion of the bone screw. The tip of the lock driver 5270 allows the locking element 5272 to be "screwed" or otherwise inserted into the plate 5250 through hole so that the exterior surface of the locking element 5272 engages the interior surface of the plate 5250 through hole. The lock driver 5270 may also be configured to have a "break away" ability to allow the locking element 5272 to break off of the lock driver 5270 and secure the locking element 5272 with the implant system. As shows, a thin portion 5276 of the lock driver at the end of a tapered portion 5275 can be configured to break when a pre-determined amount of torque is applied with the lock driver 5270. With the malleable securing element 5279 in the gap between the tip portion 5292 of the bone screw and the interior surface of the locking element 5272, slight deviations in the alignment of the tipped bone screw 5290 and the plate 5250 are accommodated while still anchoring the bone screw 5290 and securing it to the plate 5250.

Figure 52C:
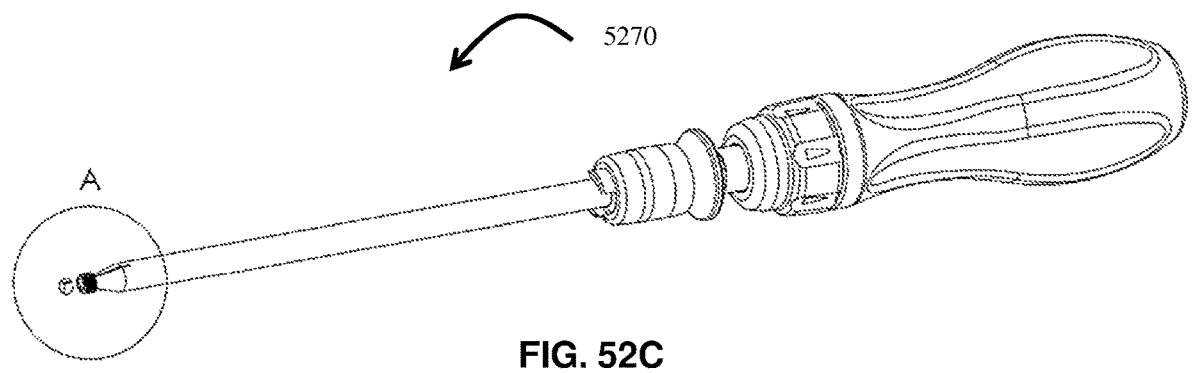
Figure 52D:
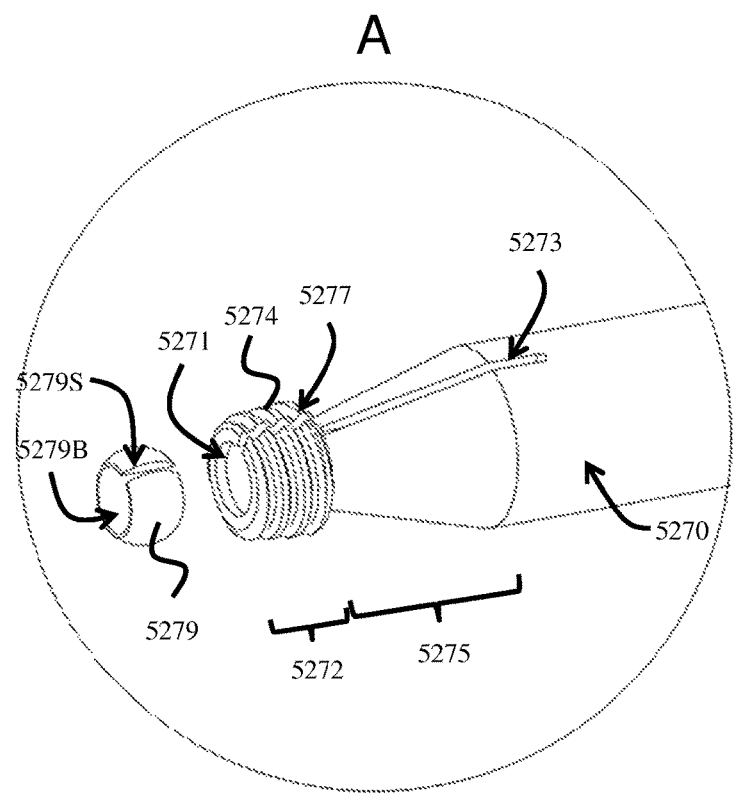

FIG. 52C shows an exploded view of the lock driver 5270 positioned to be engaged with a securing element and FIG. 52D shows details of the lock driver 5270 and securing element 5279. Referring to FIG. 52D, the locking element 5272 may be a hollow cylindrical wedge-shaped portion of the lock driver 5270 to frictionally engage the interior surface of the plate through hole and engage the exterior surface of the securing element. In some embodiments, the outer surface of the locking element 5272 is configured to facility frictional engagement with the plate through hole. For example, the outer surface make be roughened or may be radially threaded with threads 5274. In some embodiments, the locking element 5272 may include a longitudinal slit 5277 along its length to allow the locking element 5272 to reduce its circumference and provide more compressive force on the securing element 5279. In some embodiments, the lock driver 5270 may also include a longitudinal slit 5273 along a portion of its length to allow the locking element 5272 to reduce its circumference.

Also shown in FIG. 52D, the securing element 5279 generally comprises a shaped malleable element configured to frictionally engage the outer surface of the tipped bone screw and the interior surface of the locking element bore 5271. The securing element 5279 may be a hollow cylindrical sphere-shaped element with a through bore 5279B configured to engage the interior surface of the locking element bore 5271 and engage the exterior surface of the tip portion of the tipped bone screw. In some embodiments, the securing element 5279 is a malleable element to deform and mold around the tip portion and deform and mold within the locking element bore 5271 of the locking element 5272. Similar to the locking element 5272, the securing element 5279 may include a lengthwise slit 5279S to allow the securing element 5279 to reduce its circumference and provide more compressive force on the surface of the tip portion of the bone screw.

In some embodiments, the interior surface of the through holes of the plate may be tapered to accommodate the mating, wedge-shaped, locking element. The interior surface of the through hole may be configured to facilitate frictional engagement with the locking element. For example, the interior surface may be roughened or have a radial thread similar to pipe thread.

An Example of the Implant System:

FIGS. 35A-35G illustrate an example of an implant system. Implant systems consistent with this example may be used as intervertebral implant systems, intravertebral implant systems and implant systems configured for use in arthrodesis procedures. For illustration purposes only and not for limitation, this example will be described as used as a vertebral implant system. For illustration purposes only, and not for limitation, an example of the implant system used in an intervertebral application will be described and referred to as a vertebral implant system, an intervertebral implant system, a vertebral implant device and an intervertebral implant device.

Figure 35B:
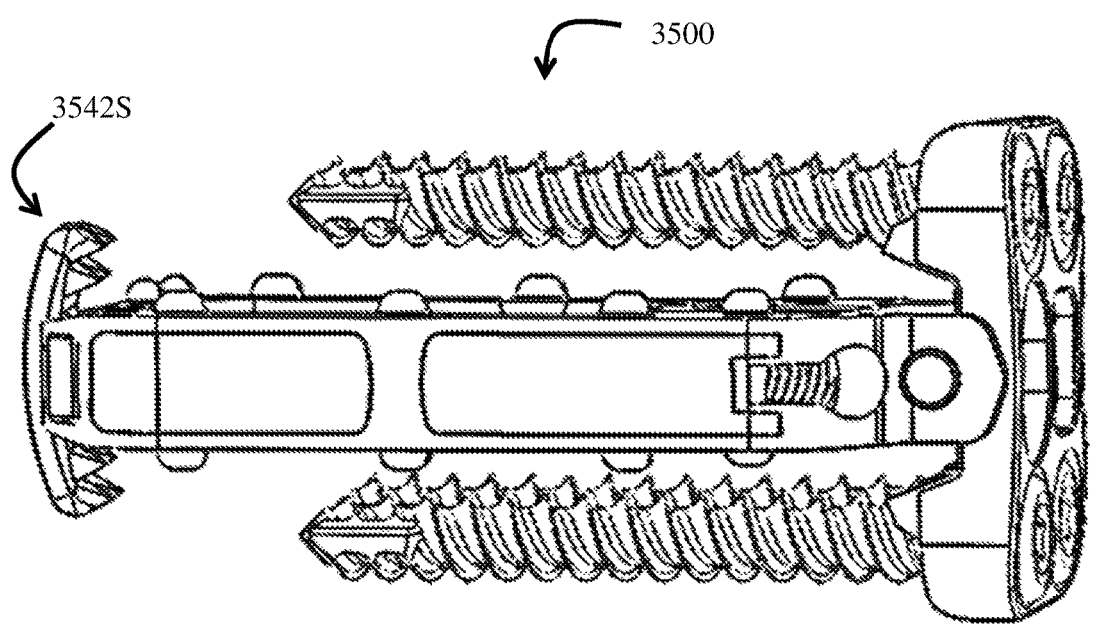
Figure 35C:
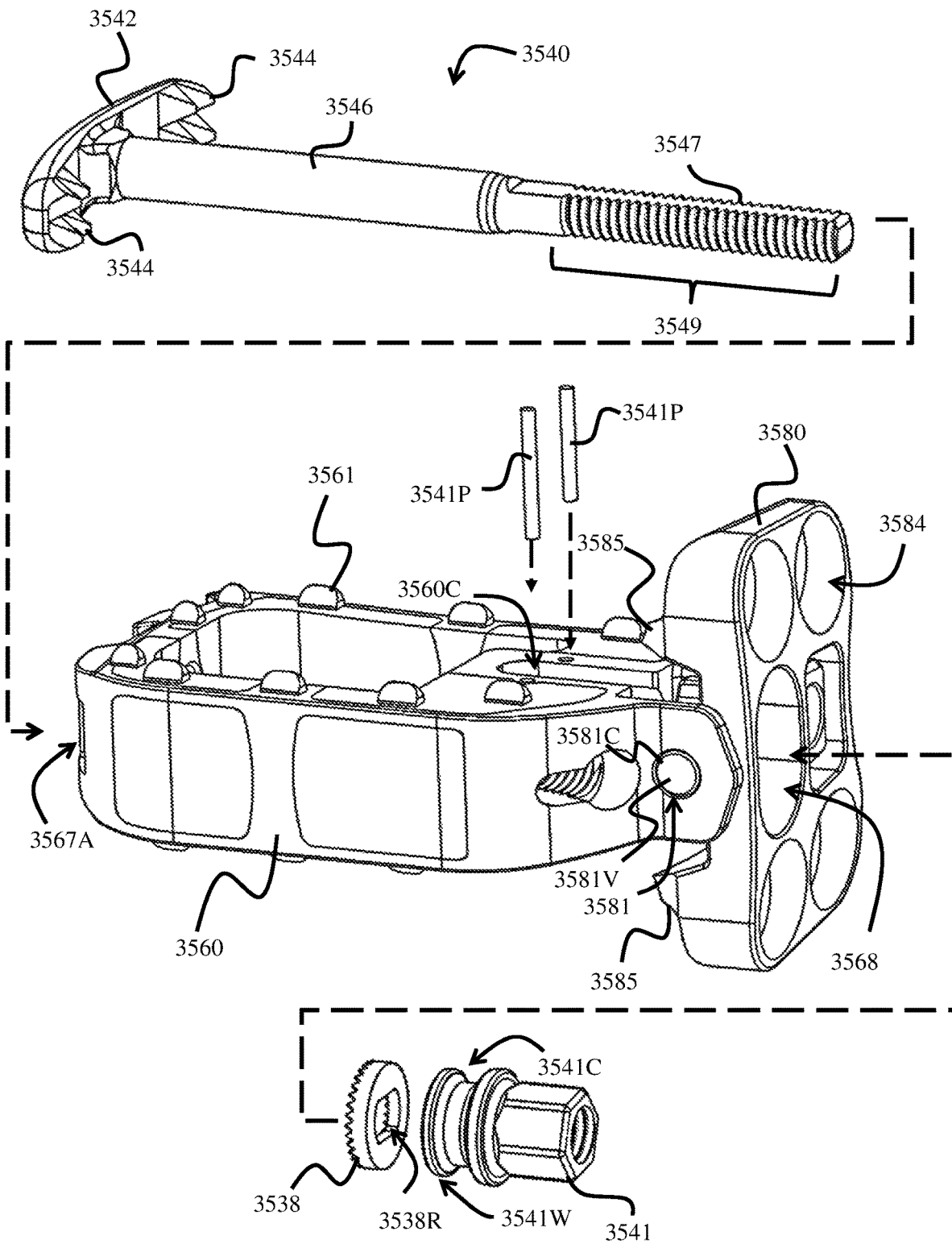

FIGS. 35A-35C show an example of a vertebral implant system comprising a vertebral implant device with FIG. 35A showing a perspective view of the vertebral implant device 3500. FIG. 35A shows the staple in an insertion position 35421 with the staple in the insertion location and in an insertion alignment. FIG. 35B shows an assembled view with anchoring elements with the staple in an example of a stabilized position 3542S where the staple is retracted relative to the cage and in a deployed alignment. FIG. 35C an exploded perspective view of the vertebral implant device 3500.

Referring to FIG. 35C, the vertebral implant device generally comprises a staple 3540, a cage 3560, an anchor frame 3580 and a coupling element 3541. The cage 3560 generally functions as a spacer between bones or between portions of a bone. The staple 3540 generally extends through a longitudinal bore of the cage to mechanically engage a sidewall of the bone to secure it and the cage 3560 to the bone. The anchor frame 3580 also provides features to receive the staple 3540 and secure itself and the cage 3560 to the bone. Together with the staple 3540, the anchor frame 3580 provides a compressive force to secure the cage 3560 to the bone. The coupling element 3541, in this example a nut, provides adjusting device features for the implant system to extend and retract the staple shaft 3546 and staple head 3542 relative to the cage 3560. This extension and retraction caused by the coupling element adjusts the locational relationship between the staple head 3542 and the 3560 and other implant device elements. Some embodiments further comprise a stop and a key to control and secure the angular alignment of the staple 3540 relative to the cage 3560.

Referring to FIG. 35C, the staple 3540 generally comprises a staple head 3542 having staple tines 3544, a staple shaft 3546, a coupling portion 3549 and an engagement portion 3547. The coupling portion 3549 provides a means to extend and retract the staple head and the engagement portion 3547 provides a means to rotate the staple shaft 3546 and the staple head 3542. The engagement portion 3547 may be any configuration that provides the ability to move the staple shaft 3546. In the example shown, the engagement portion 3547 is a proximal portion of the staple shaft 3546 having flats on its outer profile whereby the engagement portion 3547 can mate with a tool, such as a driver with a recess having mating flats, whereby the staple shaft 3546 can be engaged, pushed and rotated with the tool. The engagement portion 3547 may also provide a means to mate with a key 3538 to engage a cage stop to influence the movement of the staple shaft 3546 and the staple head 3542 relative to the cage 3560. The key 3538 may be configured with any surface features such as for example, teeth to mechanically engage a similarly configured mating surface the cage 3560. The key 3538 is also configured to engage the staple shaft 3546 whereby the key influences the movement of the staple shaft 3546 relative to the cage 3560. In the example shown, the key 3538 is a radially grooved washer configured to mesh with a mating radially grooved surface on the cage 3560. In the example shown, the radially grooved washer has a recess 3538R with a profile including flats that mate with the flats of the engagement portion 3547 of the staple shaft 3546. With this example, when the engagement tool is turned, the staple shaft 3546 is turned, the radially grooved washer is turned and the interaction of the radially grooved surface on the cage meshes with the radially grooved surface on the radially grooved washer to urge the engagement tool and the staple shaft 3546 to lock at a finite number of predetermined rotational angles, or radial positions, relative to the cage 3560.

Referring to FIG. 35C, the cage 3560 comprises a body generally having a longitudinal axis extending from the proximal coupling with the anchor frame to the distal bore for the staple shaft and a transverse axis running generally perpendicular to the bore for the staple. The upper surface of the cage defines the cage upper surface plane for the implant device and the lower surface defines the cage lower surface plane. The upper and lower surface planes, the space between them and the angles between them define the correction that can be provided through the implanting of the cage 3560. The cage 3560 has a through bore extending along the longitudinal axis of the cage from a first lateral side of the cage to a second lateral side. The through bore is configured to receive and retain the staple shaft 3546. The central bore of the cage also defines a retaining channel 3560C to accept pins to retain the nut. The retaining channel is configured to receive and retain pins located to capture the nut 3541 so that it may be rotated relative to the cage and the staple shaft 3546 yet maintain its approximate position relative to the longitudinal axis of the cage 3560. In the example shown, the nut 3541 is retained in the retaining channel 3560C with pins 3541P that are received in pin holes that extend from one surface of the cage 3560 into the retaining channel 3560C and into the retaining channel 3541C of the nut 4241. This configuration retains the nut but provides for rotational freedom of movement and some minimal longitudinal translation along the longitudinal axis of the cage. The cage 3560 may further comprises a cage stop (not shown) configured to mate with the engagement surface of the key. In the example shown, the cage stop comprises a radially grooved surface on the inside of the retaining channel 3560C that engages with the radially grooved surface of the washer 3538 to urge the engagement tool and the staple shaft 3546 to lock at predetermined rotational angles relative to the cage 3560. The cage 3560 may further comprises one or more staple tine recesses 3567A to receive the staple tines when the staple head 3542 is in an insertion position. The cage may further comprise one or more retention elements to help the upper and lower surfaces of the cage engage the bone. In the example shown, the retention element comprises one or more cleats 3561. The cage may further comprise a pivot coupler 3581 to pivotally couple the cage 3560 to the anchor frame 3580. The pivot coupler 3581 may be any type of coupling that allows the anchor frame 3580 to move in relation to the cage 3560. In the example shown, the pivot coupler 3581 comprises a cylindrical protrusion received in a through hole on the proximal end of the cage 3560 whereby the anchor frame 3580 pivots about an axis about ninety degrees to a longitudinal axis of the cage. In some embodiments, the anchor frame pivots about an axis having a range of about 45 degrees to 90 degrees to the longitudinal axis of the cage.

Referring to FIG. 35C, the anchor frame 3580 is operably coupled to and generally extends perpendicular to the longitudinal axis of the cage 3560 and comprises securing elements to secure the cage to bone. The anchor frame 3580 may have a through bore 3568 providing access for tools to the nut 3541, the proximal end of the staple shaft 3546 and the central bore of the cage 3560. The anchor frame 3580 may also have through holes 3584 to receive anchoring elements to anchor the anchor frame 3580 and the cage 3560 to the bone. The anchor frame may further comprise a pivot coupler 3581 to pivotally couple the anchor frame 3580 to the cage 3560. The pivot coupler 3581 may comprise an anchor frame pivot element 3581V and a cage pivot element 3581C, both configured to pivotally couple the anchor frame to the cage. In the example shown, the anchor frame pivot element 3581V comprises at least one cylindrical protrusion extending from the surface of the anchor frame 3580 and received in at least one cage pivot element 3581C which comprises at least through hole on the proximal end of the cage 3560 whereby the anchor frame 3580 pivots about an axis about ninety degrees to a longitudinal axis of the cage.

The coupling element is generally configured to mate with the cage 3560 and the staple shaft 3546 to longitudinally move the staple shaft 3546 and the staple head 3542 through different longitudinal locations relative to the cage 3560. In this example, the coupling element is a nut 3541 also configured to be engaged by engagement tools and to allow access for engagement tools to engage the engagement portion 3547 of the staple shaft 3546. In the example shown in FIG. 35C, the nut 3541 is longitudinally fixed relative to the cage 3560 and anchor frame 3580 and engages the coupling portion 3549 of the staple shaft 3546 to extend and retract the staple shaft 3546 and staple head 3542 relative to the cage 3560. The nut 3541 is internally threaded to engage the threaded coupling portion 3549 of the staple shaft 3546 and allow the threaded portion 3549 to extend through the proximal end of the nut 3541 exposing the flats of the engagement portion 3547 of the staple shaft 3546. The nut 3541 has an outer profile to be engaged by an engagement tool to rotate the nut 3541. The nut 3541 is received in the cage retaining channel 3560C and accessible through the through bore 3568 of the anchor frame 3580. The nut 3541 is retained in the cage retaining channel 3560C by the pins 3541P, a nut flange 3541W and a nut retaining channel 3541C. The nut flange 3541W can be sized in relation to the key, in this example the washer 3538, to only be inserted to a certain position in the bore of the cage. The pins 3541P extend through the end bore and into the retaining channel 3541C of the nut 3541. Together, the size of the retaining channel 3560C, the size of the nut flange 3541W and the pins, hold the nut 3541 within the retaining channel 3560C of the cage 3560 and allow the nut 3541 to receive the threaded portion 3549 of the staple shaft 3546 and rotate to longitudinally move the staple shaft 3546 and staple head 3542 relative to the cage 3560.

Figure 35D:
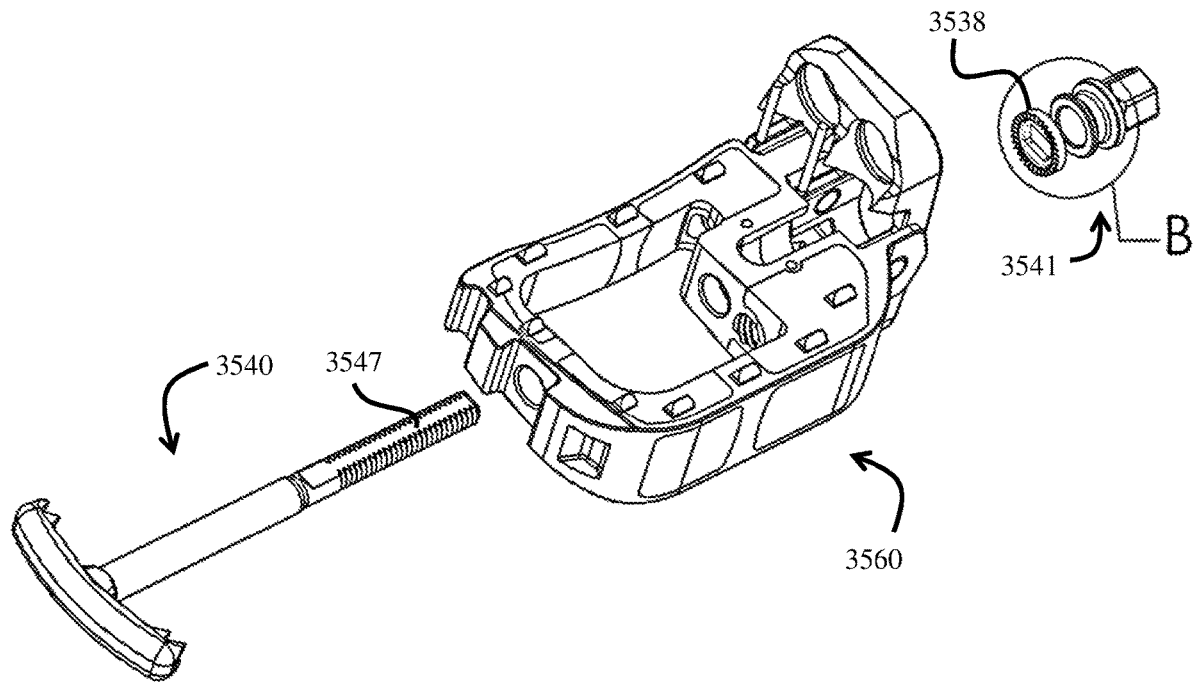
Figure 35E:
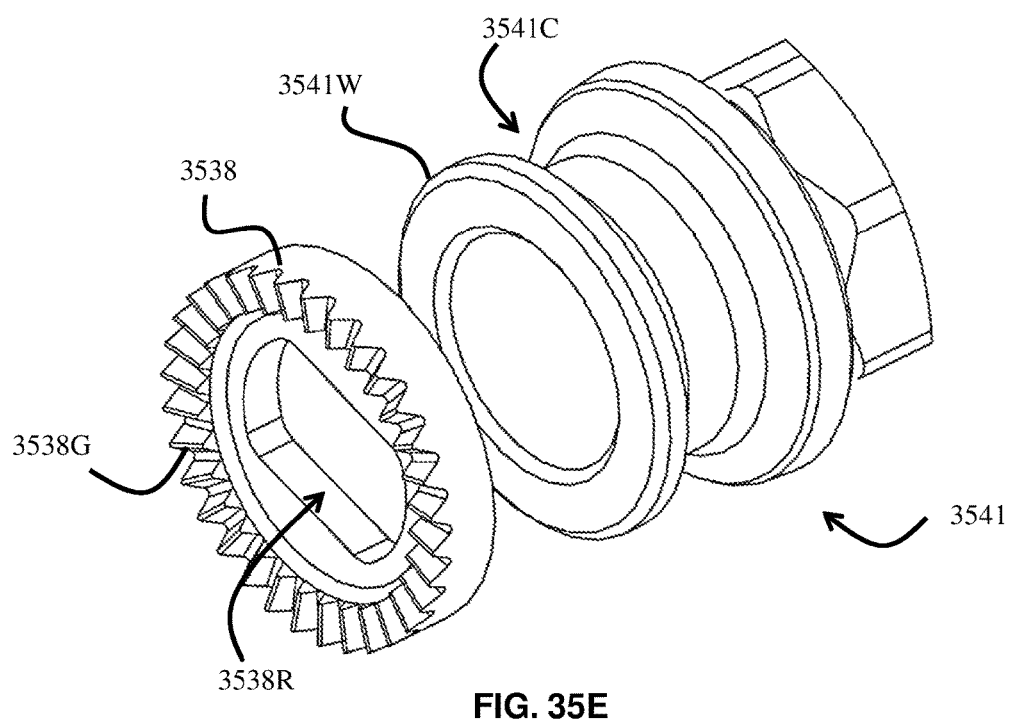

FIG. 35D shows an exploded perspective view of an example of a vertebral implant device showing the staple 3540, the cage 3560, the nut 3541 and the washer 3538. FIG. 35E details callout B of the nut 3541 showing the nut flange 3541W and the retaining channel 3541C. Also shown is the washer 3538 and the radial grooves 3538G and the recess 3538R with the flats to engage the engagement portion 3547 of the staple shaft 3546.

Figure 35F:
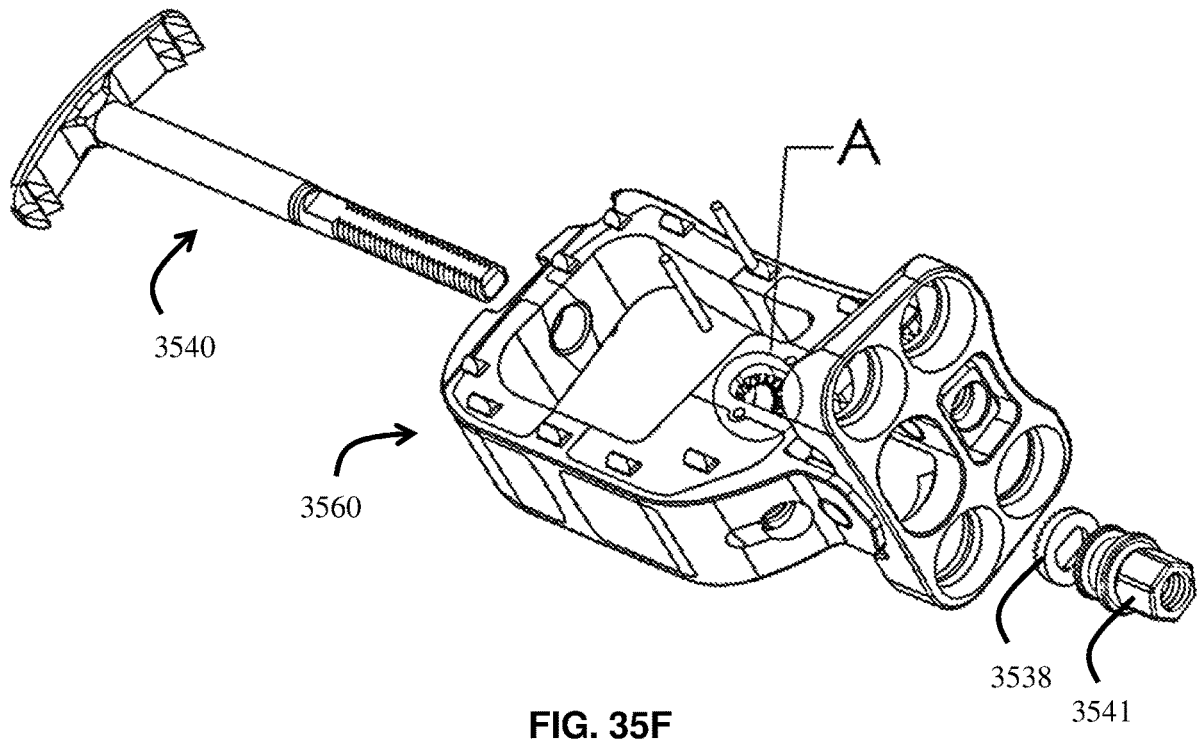
Figure 35G:
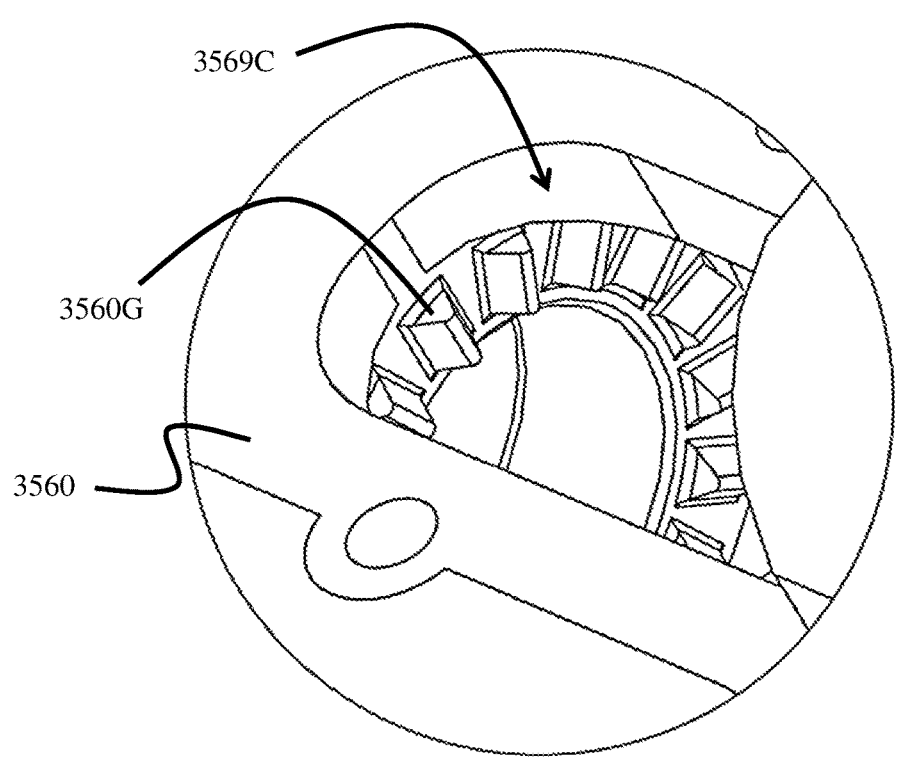

FIG. 35F shows an exploded perspective view of an example of a vertebral implant device showing the staple 3540, the cage 3560, the nut 3541 and the washer 3538. FIG. 35G details callout A of the end bore and retaining channel 3569C of the cage 3560 showing the radially grooved surface 3560G on the cage 3560.

Figure 36B:
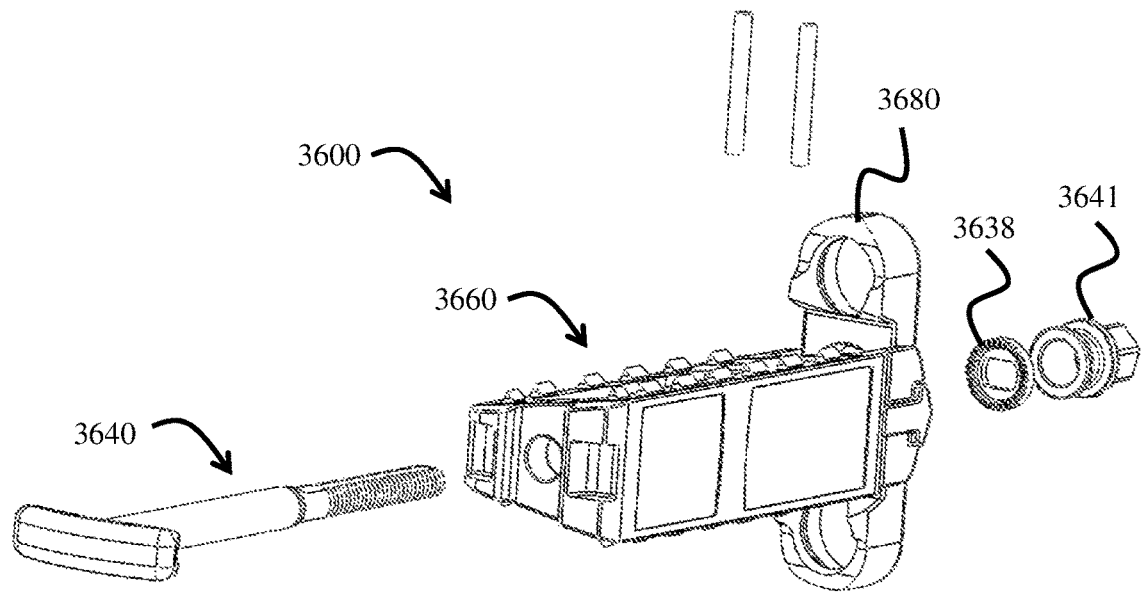

FIGS. 36A and 36B show views of an example of a vertebral implant device 3600 comprising a staple 3640, a cage 3660, an anchor frame 3680, a key 3638 and a nut 3641. FIG. 36A shows an exploded perspective distal view and FIG. 36B shows an exploded perspective proximal view. In this example, the anchor frame 3680 has two through holes 3684 to accommodate anchoring elements to anchor the anchor frame 3680 to a bone. In this example, the pivot coupler 3681 comprises a protrusion on the cage that mates with a recess on the anchor frame to allow the anchor frame to pivot relative to the cage.

Figure 37A:
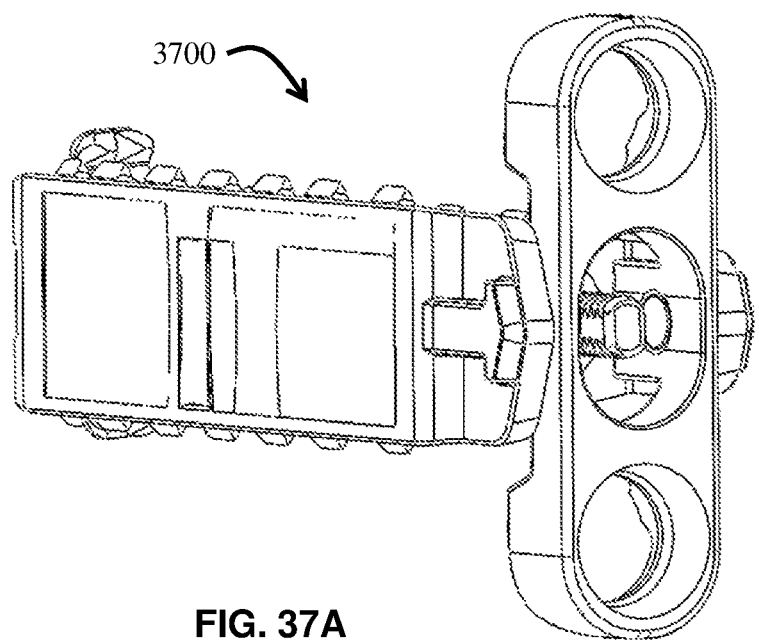
FIGS. 37A and 37B show views of an example implant system assembled where
Figure 37B:
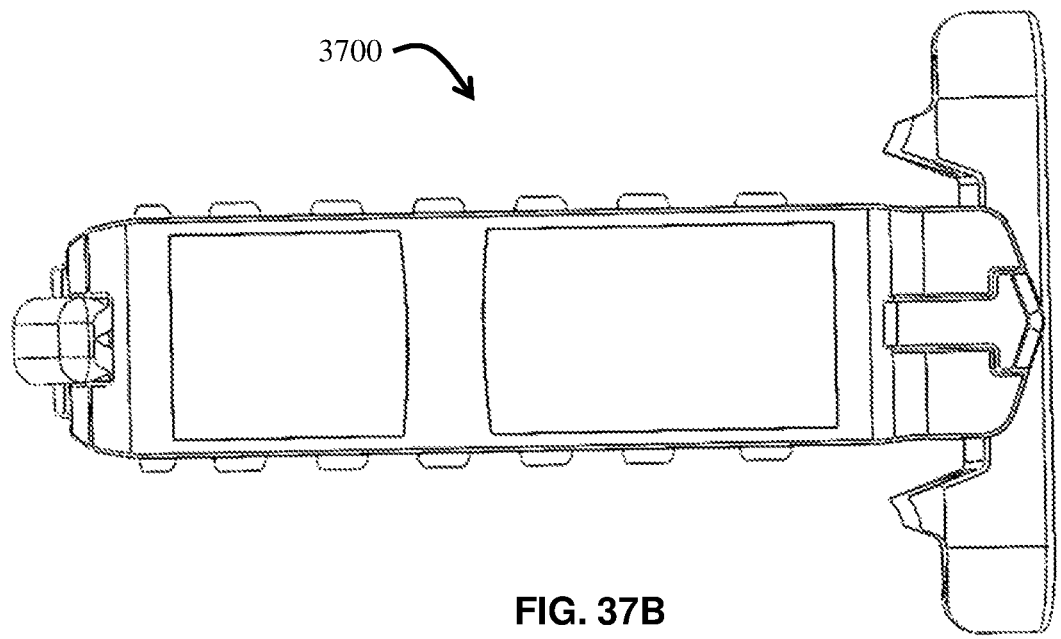

FIGS. 37A and 37B show views of an example vertebral implant device 3700 consistent with FIGS. 36A and 36B. FIG. 37A shows an assembled proximal perspective view and FIG. 37B shows a side view.

Figure 38A:
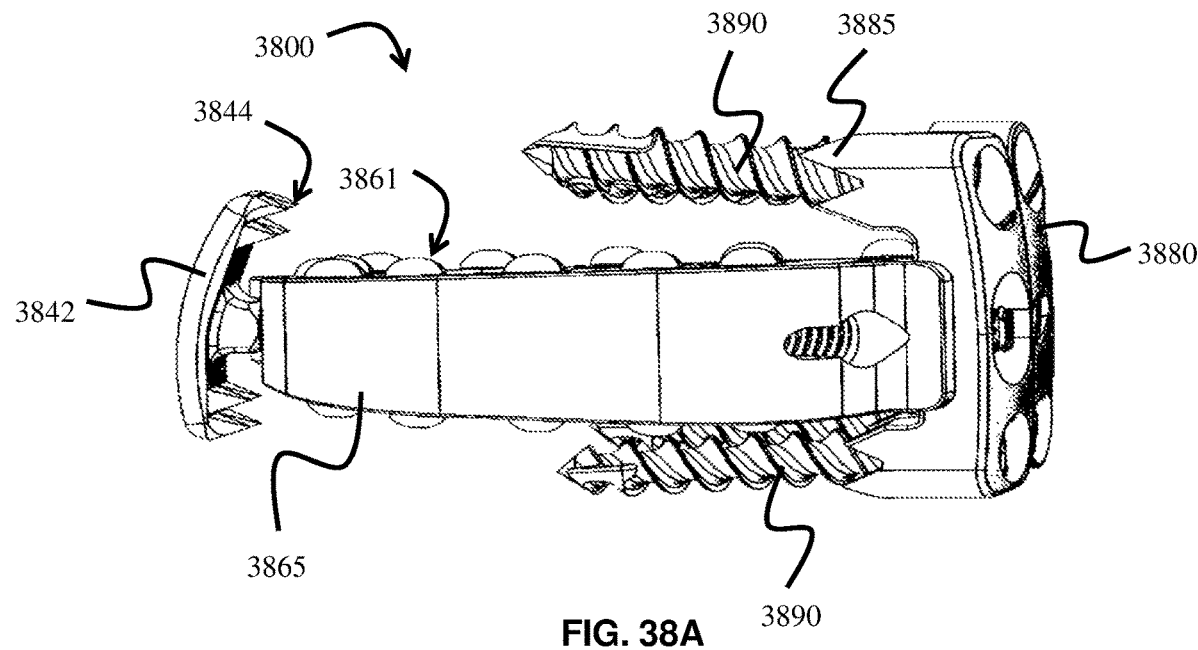
FIGS. 38A and 38B show examples of an implant system with FIG. 38A showing an example configured for use in an intravertebral application and FIG. 38B showing an example configured for use in an intervertebral application.
Figure 38B:
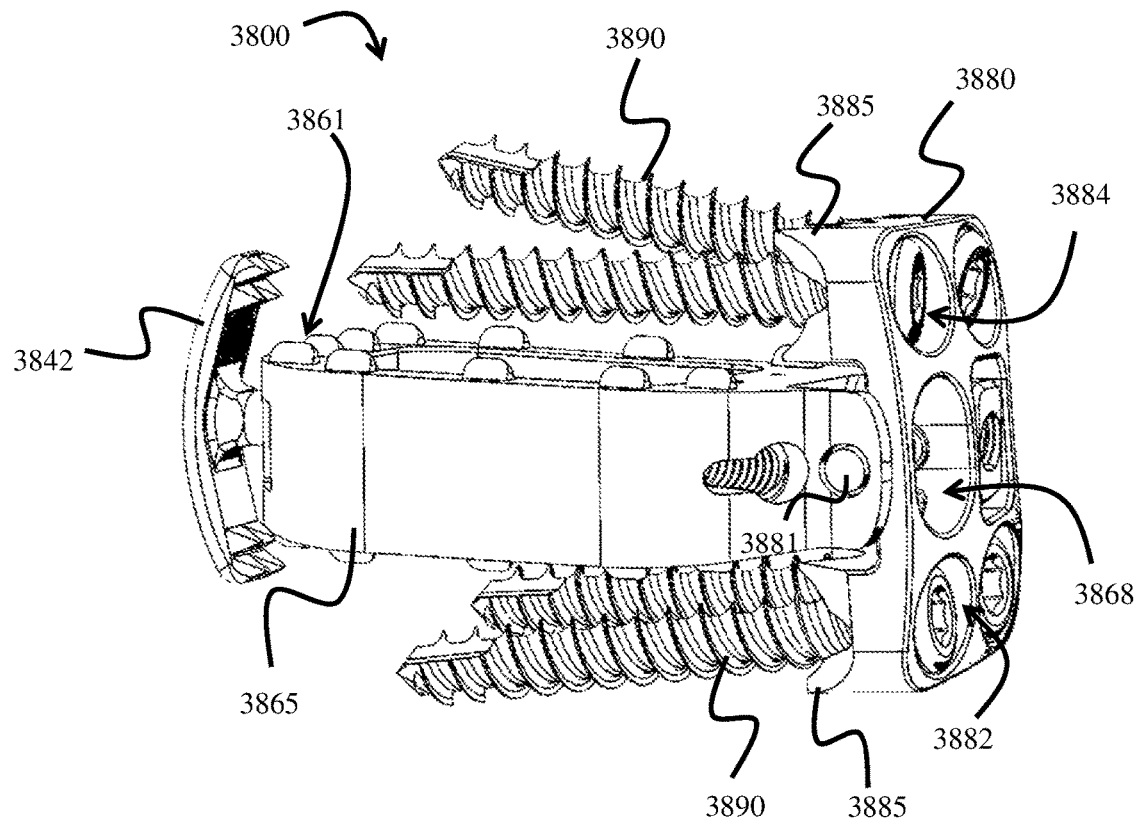

An Example of the Implant System:

FIGS. 38A and 38B illustrate other examples of an implant system. Implant systems consistent with this example may be configured for use as intervertebral implant systems, intravertebral implant systems and implant systems configured for use in arthrodesis procedures. For illustration purposes only and not for limitation, an example of the implant system used in vertebral applications will be described and referred to as a vertebral implant device, an intervertebral implant device or an intravertebral implant device.

FIGS. 38A and 38B show the implant system comprises implant device 3800 having a staple (staple head 3842) and a cage 3865. The implant system is anchored to the vertebral body by the staple head 3842 and one or more bone screws 3890 received in through holes of an anchor frame 3880. The anchor frame 3880 may further comprise longitudinal teeth 3885 protruding from the superior and inferior surfaces to prevent anterior migration of the implant during implantation. The through holes 3884 and 3882 may be unconstrained to allow the bone screws 3890 to be directed axis to optimize boney fixation. As shown, the cage 3865 has a distal/contralateral/far side staple with a staple head 3842 with staple tines 3844 that may be deployed and retracted to secure the cage 3865 to the bone. The cage 3865 may also have cleats 3861 to help secure and stabilize the cage 3865 during and after insertion. The anchor frame 3880 may have additional through holes to allow for access to implant components such as the staple shaft and insertion rod access.

FIG. 38A shows an example implant device 3800 configured for use as an intravertebral implant device. As shown, the implant device 3800 has a less symmetrical dimension in height about a longitudinal centerline of the cage to reflect the limited area to secure implant components to the vertebral body. In this example, the anchor frame 3880 is also rigidly coupled to the cage 3865. As compared to intervertebral examples, the bone screws 3890 may be smaller. For example, a suitable bone screw 3890 may be a 3.5 mm, 4.5 mm or 5.5 mm bone screw. In one example, the superior bone screws are 5.5 mm and the inferior bone screws are 4.5 mm.

FIG. 38B shows an example of the implant device 3800 configured for use as an intervertebral implant device. In this example, the anchor frame 3880 comprises a proximal/ipsilateral/near side anchor frame 3880 operably coupled to the cage 3865 with a pivot connection 3881. The pivot connection 3881 may be any type of connector to pivotally or hingedly couple the anchor frame 3880 to the cage 3865 and allow the implant device 3800 to pivot relative to the cage and accommodate specific anatomy and ensure stability. The pivot connection 3881 may comprise an anchor frame pivot element and a cage pivot element, both configured to pivotally couple the anchor frame to the cage. The anchor frame 3880 has a through hole 3868 to allow insertion tools to access the proximal end of the staple shaft and other proximal components. The anchor frame 3880 may be secured to the bone with bone screws 3890 superior and inferior to the cage 3865 that are received through integrated superior and inferior through holes 3884 and 3882 respectively. The bone screws 3890 may be any size suitable to secure the anchor frame 3880 to the bone. In some embodiments, the superior bone screws may be 3.5 mm, 4.5 mm or 5.5 mm bone screws. In some embodiments, the inferior bone screws may be 3.5 mm, 4.5 mm or 5.5 mm bone screws.

Figure 39A:
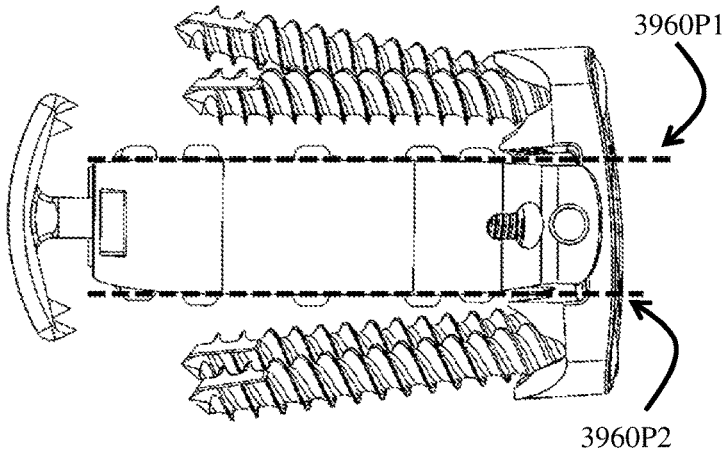
FIGS. 39A-39D show examples of an implant system with FIG. 39A showing a side view of an example configured for use in an intervertebral application to correct lordosis, FIG. 39B showing a proximal end view of the example of FIG. 39A, FIG. 39C showing a side view of an example configured for use in an intervertebral application to correct lordosis and coronal alignment, and FIG. 39D showing a proximal end view of the example of FIG. 39C.
Figure 39B:
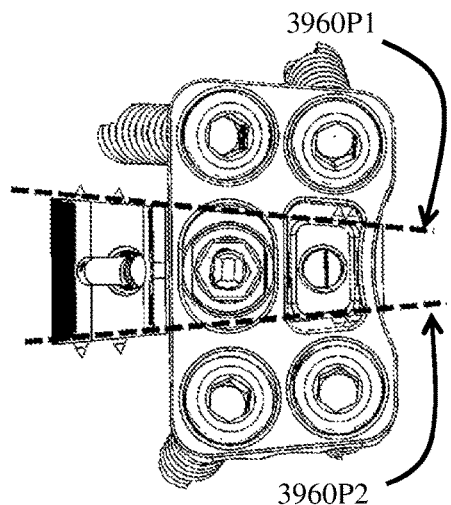
Figure 39C:
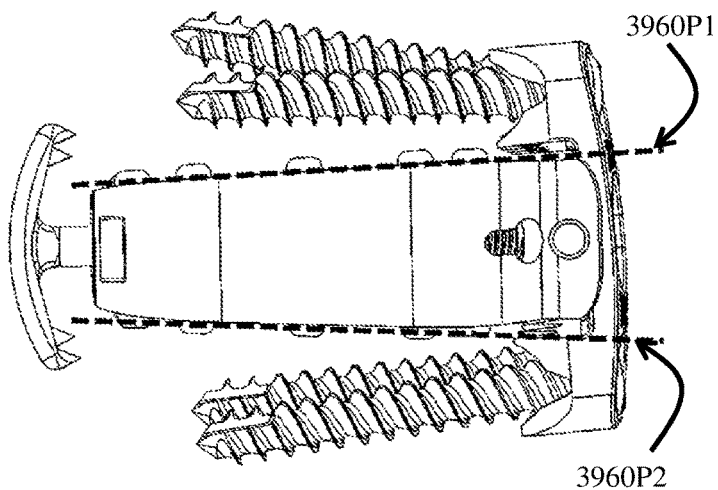
Figure 39D:
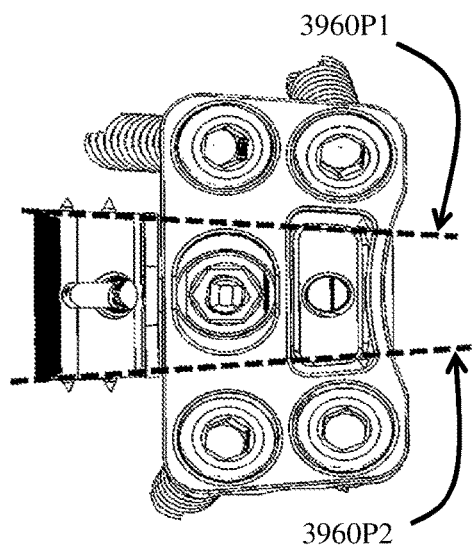

FIGS. 39A and 39B show views of an implant device consistent with the example of FIG. 38B with the exterior surface planes 3960P1 and 3960P2 of the cage at angles configured for lordosis correction only. FIGS. 39C and 39D show views of an implant device consistent with the example of FIG. 38B configured for lordosis and coronal correction.

Figures 40A, 40B, 40C:
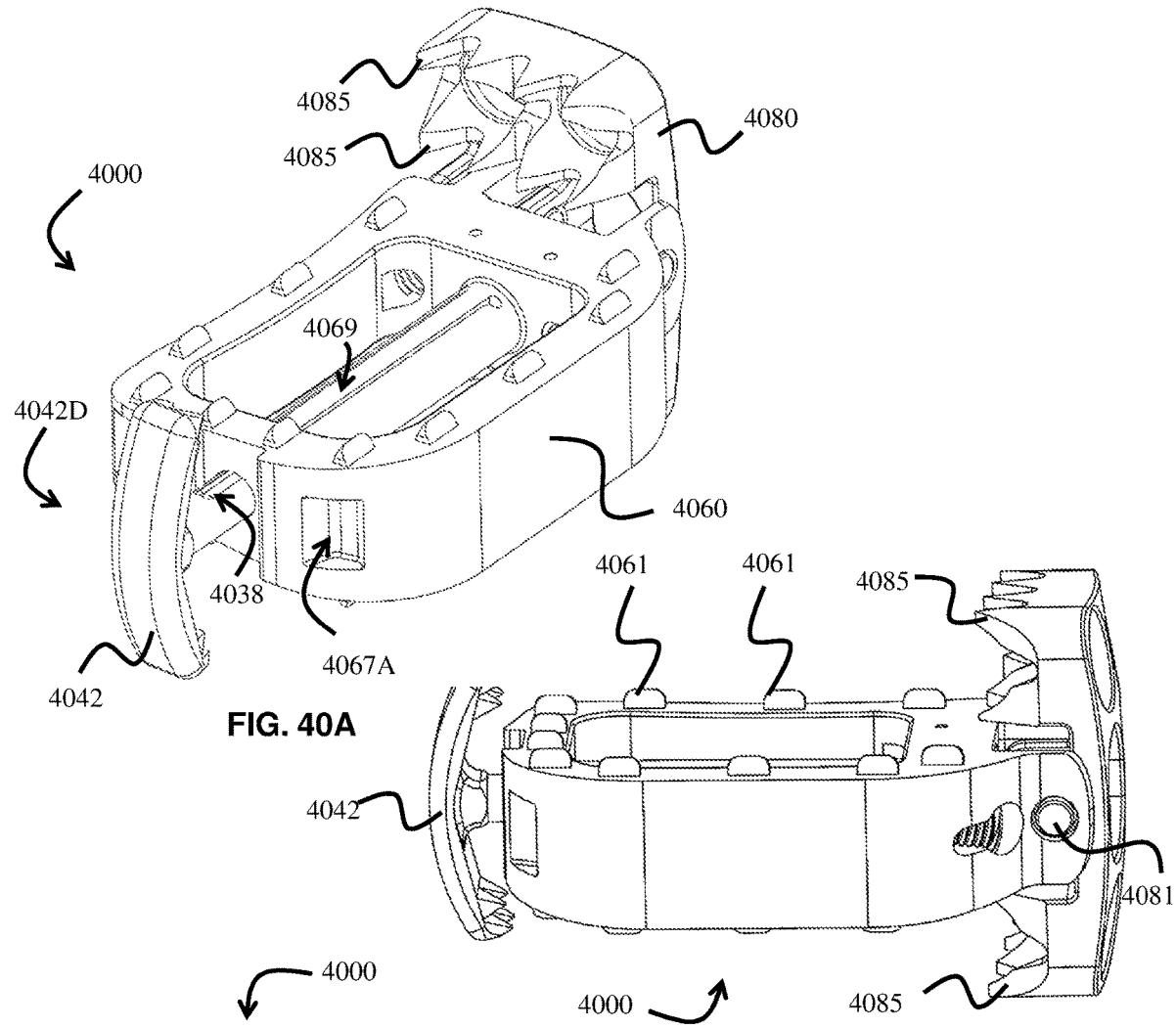

FIGS. 40A-40F illustrate different views of an example of an implant device with a staple in a deployed position. Referring to FIGS. 40A and 40B, consistent with the example of FIG. 39B, the implant device 4000 has a distal staple with a staple head 4042, a cage 4060, a cage stop 4069, a key 4038, a staple tine recess 4067A, teeth 4085, a pivot connection 4081, and cleats 4061. The pivot connection 4081 may be any type of connection that allows the anchor frame 4080 to swivel or pivot in relation to the cage 4060. As shown, the pivot connection 4081 comprises multiple pins extending from the anchor frame 4080 and received in multiple through holes on the distal end of the cage 4060 that allow the anchor frame 4080 to swivel about a pivot point generally in line with the longitudinal axis of the staple head 4042 and perpendicular to the longitudinal axis of the staple shaft.

Referring to FIG. 40C, the cage 4060 has a central cage sleeve to receive the staple shaft. As shown, the cage sleeve has a cage stop 4069 to engage with the staple shaft and control its rotation. The cage stop 4069 may be any mechanism to control the position of the staple shaft relative to the cage. As shown in this example, the cage stop is defined by a cage stop slit 4069S that is "U" shaped and extends through the cage sleeve to define a finger shaped cage stop 4069. Under the distal end of the cage stop 4069 may be a protrusion that can engage components of the staple shaft (see FIG. 42C).

FIG. 40D shows a side view and FIG. 40E shows a distal end view of the implant device 4000.

FIG. 40F shows a distal end view of the implant device. As shown, through the through hole of the anchor frame 4080, the proximal end of a nut 4041 is shown. The nut 4041 is threaded and engages the proximal end of the staple shaft. Also shown are pins 4041P and a nut flange 4041W. The pins 4041P are configured to fit behind the nut flange 4041W and in a retaining channel to retain the nut relative to the cage and the staple. (Also see FIGS. 42A-42C.)

Figure 41A:
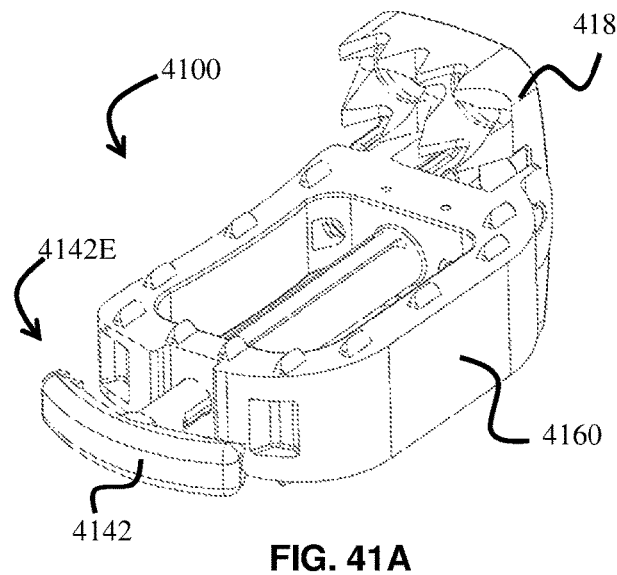
FIGS. 41A-41F show different views of an example implant system where 41A shows a top perspective view of an example implant system with the staple in a partially deployed position.
Figure 41B:
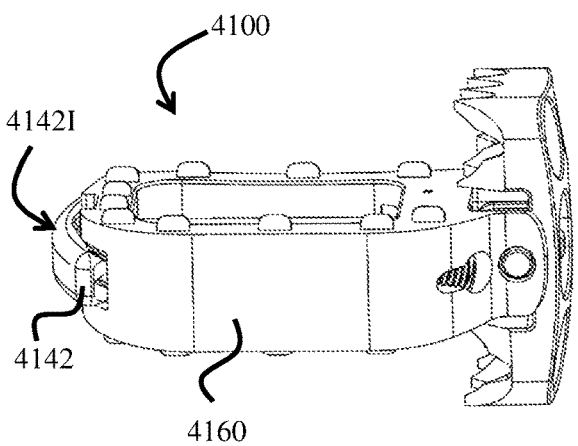
Figure 41C:
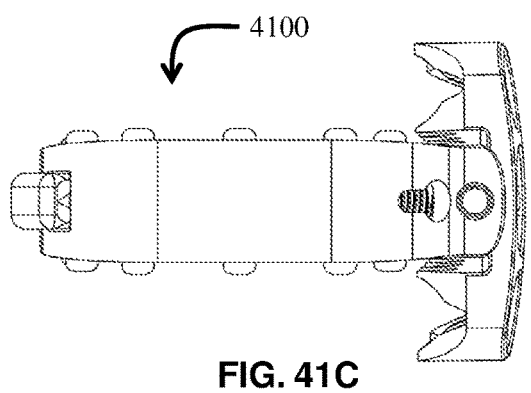
Figure 41D:
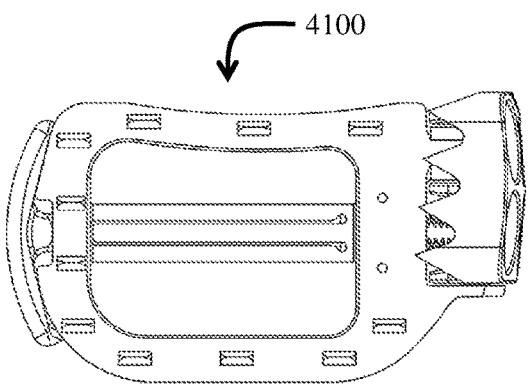
Figure 41E:
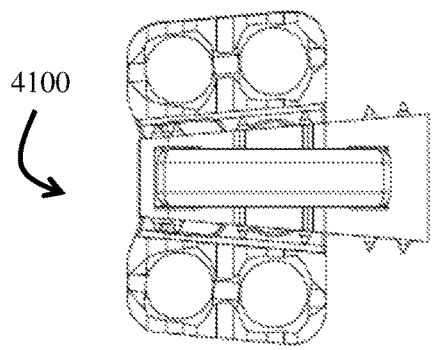
Figure 41F:
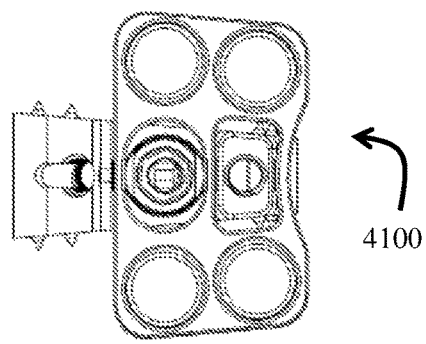

FIGS. 41A-41F show different views of an implant device 4100 consistent with FIGS. 40A-40F with the distal staple head 4142 in different positions relative to the cage 4160 and the anchor frame 4180. FIG. 41A shows an example of implant device with the staple head 4142 in an example of a partially extended position 4142E. As shown, the staple head 4142 in the extended position 4142E is at an extended location away from the cage and in an insertion alignment. FIGS. 41B-41F show examples of an implant device with the staple in an example of an undeployed/insertion position 4142I. In the insertion position 4142I, the staple head 4142 is at an insertion location proximal to the cage 4160 and in an insertion alignment.

FIGS. 42A-42C show detailed views of an implant device with FIG. 42A exploded showing the staple, the cage and the anchor frame, FIG. 42B showing a distal end view, FIG. 42C showing a callout of section A from FIG. 4B.

Referring to FIG. 42A, the distal staple comprises the staple head 4042, staple shaft 4246, a threaded portion 4249 and an engagement portion 4247. In this example, the staple head 4042 is in a deployed position 4042D with the staple head 4042 at an extended location extended away from the cage 4060 and in a deployed alignment. Consistent with other examples, the threaded portion 4249 provides a means to extend and retract the staple head and the engagement portion 4247 provides a means to rotate the staple shaft 4246 and the staple head 4242. The staple shaft 4246 also has a key 4238 configured to mate with the cage stop 4269 to limit movement of the staple shaft relative to the cage 4260. As shown, in this example, the key 4238 is a recess channel extending along the longitudinal surface of the staple shaft 4246. With this configuration, and the cage stop 4269, when the staple shaft is turned, the cage stop 4269 is urged into the key 4238 and rotation is stopped but movement in the direction of the longitudinal access is allowed along the length of the key 4238.

Also shown in FIG. 42A is a nut 4041. The nut 4041 is threaded to engage the threaded portion 4249 of the staple shaft 4246. The nut is received in the cage 4260 but accessible to tools through through holes in the anchor frame. The nut 4241 is retained in the cage 4260 by pins 4241P, a nut flange 4241W and a retaining channel 4241C. The nut 4241 is received in a proximal end bore of the cage 4260. The nut flange 4241W is sized in relation to the bore to only be inserted to a certain position. The pins 4241P are received in pin holes that extend through the end bore and into the retaining channel 4241C of the nut 4241. Together, the size of the bore, the size of the nut flange 4241W and the pins 4241P, hold the nut within the bore of the cage 4060 and allow the nut 4241 to receive the threaded portion 4249 of the staple shaft 4246 and rotate to move the staple shaft 4246 relative to the cage 4260.

FIGS. 42B and 42C show distal views of the implant device 4200 showing detail of the staple sleeve inside opening 4235 without the staple shaft. As shown, the inside opening 4235 of the staple sleeve without the staple shaft shows the cage stop 4269 with a protrusion configured to engage the key 4238 of the staple shaft 4246. As shown, the cage stop 4269 is configured to elastically allow the staple shaft 4246 to rotate and when the key 4238 is encountered, the cage stop 4269 is urged into the key 4238 and rotation is stopped.

Consistent with other examples of a staple drive handle assembly, FIGS. 42D-42I show detailed views of components of a suitable staple drive handle assembly configured to engage with the implant device.

Figure 42G:
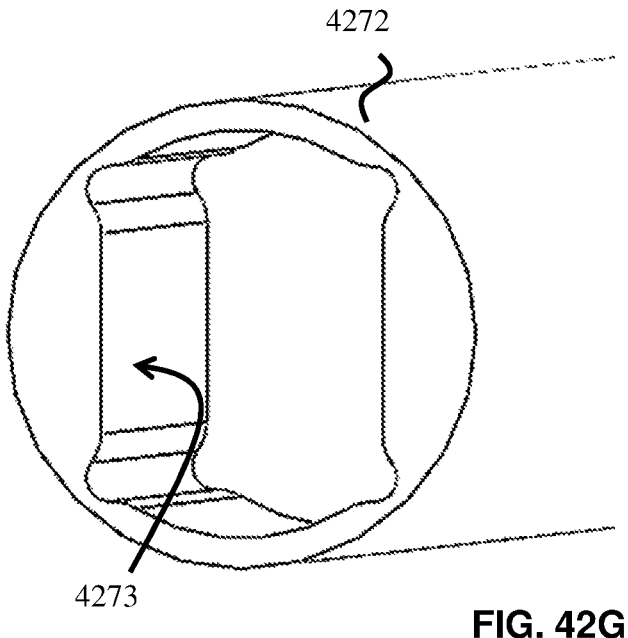

FIGS. 42D-42F show an example of an outer drive rod 4274 of a staple drive handle assembly having a recess 4274R for an inner drive rod (see FIG. 42G). As shown, the end of the outer drive rod 4274 has an inner surface defining a nut engagement portion 4275 configured to engage the shape of the nut 4241 so that the turning of the nut, when the threaded portion of the staple shaft 4246 is engaged with the threads of the nut 4241 and the nut is retained in the cage by the nut flange 4241W and the retaining channel 4241C, the staple shaft 4246 can be extended away from and retracted towards the cage.

Figure 42H:
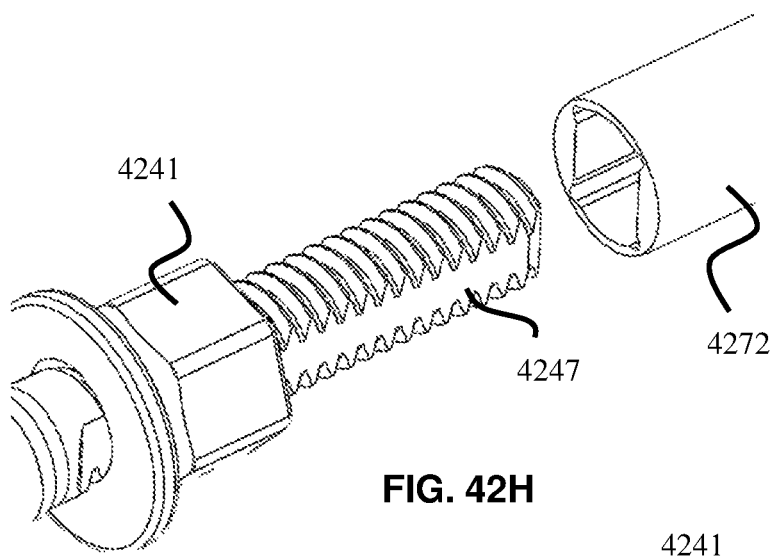
Figure 42I:
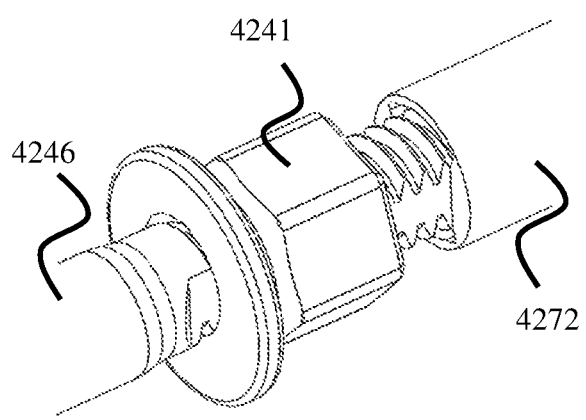

FIG. 42G-42I show an example of an inner drive rod 4272 having an inner surface shape defining a shaft engagement portion 4273 to engage the engagement portion 4247 of the staple shaft 4246. With this engagement, by rotating the inner drive rod 4272, the staple shaft 4246 and the staple head are rotated without turning the nut 4241 to put the staple head in the deployed position.

Figure 43A:
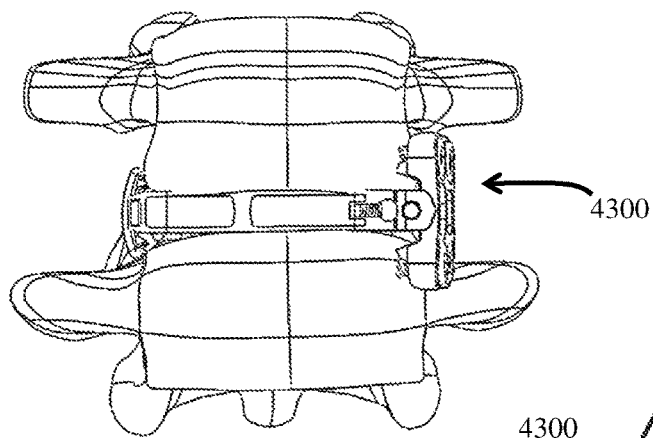
FIGS. 43A and 43B show an example implant device implanted as an intervertebral implant with FIG. 43B showing a side view of the embodiment in FIG. 43A.
Figure 43B:
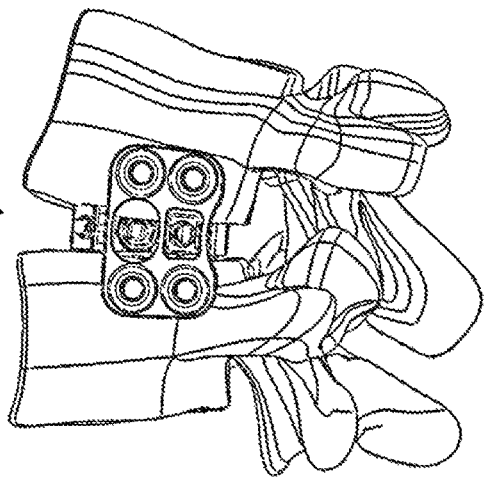

FIGS. 43A and 43B show implant device 4300 implanted as an intervertebral implant having four holes for four anchoring elements. FIG. 43B shows a side view of the example in FIG. 43A.

Figure 44A:
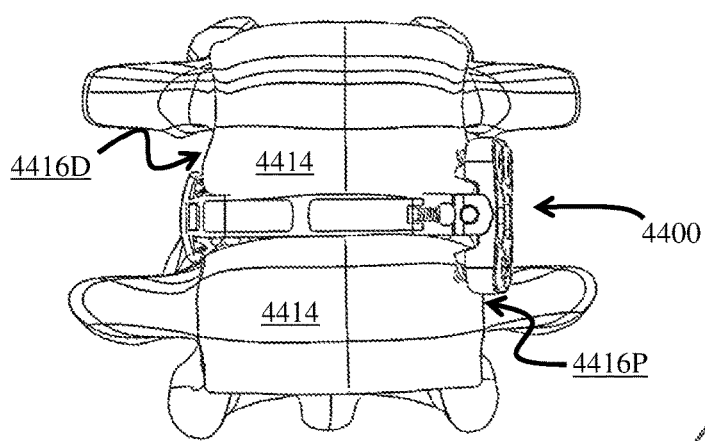
FIGS. 44A and 44B show an example implant device implanted as an intervertebral implant with FIG. 44B showing a side view of the embodiment in FIG. 44A.
Figure 44B:
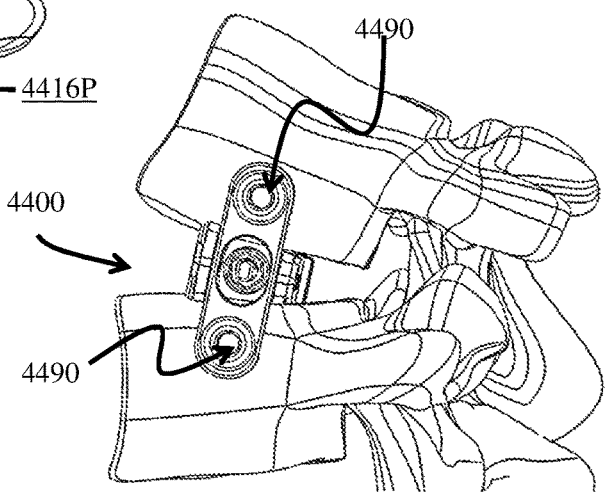

FIGS. 44A and 44B show implant device 4400 implanted as an intervertebral implant having two holes for two anchoring elements. FIG. 44B shows a side view of the example in FIG. 44A. As shown, the implant device 4400 is secured between two vertebral bodies 4414 and the implant is secured to the vertebral body's distal lateral side sidewall 4416D with the staple and secured to the vertebral body proximal sidewall 4416P with the anchor frame and anchoring elements 4490.

An Example Implant System in Operation:

The implant device generally uses the exterior surface planes of the cage to alter the alignment of skeletal components of a mammalian body. Referring to FIG. 1A, the disclosed implant device primarily provides adjustment of the spine in the sagittal (110) and coronal (100) planes and combinations of these two planes.

Referring to FIG. 1B, the implant device, when used as a vertebral implant, is intended to be used on the vertebra and may be inserted from different orientations. As shown, the implant device may be inserted from a lateral/side position, from an anterior/front position or from an oblique position. The implant system may also be applied to different portions of the spine (thoracic or lumbar).

FIGS. 7, 8 and 9A-9C further illustrate examples of the implant device and how it may be implanted in the vertebral body.

FIG. 7 shows an example osteotomy and an exploded view of a cage 760, a distal staple 740 and anchor frame 780. FIG. 8 shows the example of FIG. 7 inserted, secured and anchored to the vertebral body by a single distal staple and anchoring members such as bone screws. Although the examples shown in FIGS. 7 and 8 the correction by the cage is limited to the sagittal plane, it is understood that alterations may be made to the surface plane of the vertebral body by different cage surface angles of the cage. For example, it is understood that the correction by the cage may be to either of the sagittal and coronal planes or both.

FIG. 9A shows an example of an implanted implant device with an inner staple 920 and a distal staple 940.

FIG. 9B shows an example of an implanted implant device with a single distal staple 940 positioned outside the vertebral body.

FIG. 9C shows an example of an implanted implant device with a single distal staple 940 with the staple tines defining a concave shape.

Described below in detail is an example anterior-to-psoas (ATP) approach for a vertebral implant system used in an intravertebral procedure which is conducted oblique to the coronal plane for creating a vertebral body osteotomy and then for placing the implant within the vertebral body for correction in the coronal plane. The instruments and procedure can easily be adapted by the skilled artisan to accommodate approaches such as lateral, oblique and/or ATP. With the disclosed systems and methods, spine correction is established while the spine flexibility thru the disc and facet joints is retained, and the vertebral body then fuses in a period of time, such as 12 weeks, for a solid corrected vertebral structure.

An example method of implanting one example of the implant system consistent with the implant system of FIGS. 35A-3GF generally comprises the steps described below.

The far-side retractor tool (for example only, see example at FIG. 22) may be positioned around the implant site to protect tissue before or during the implant procedure.

Figure 10A:
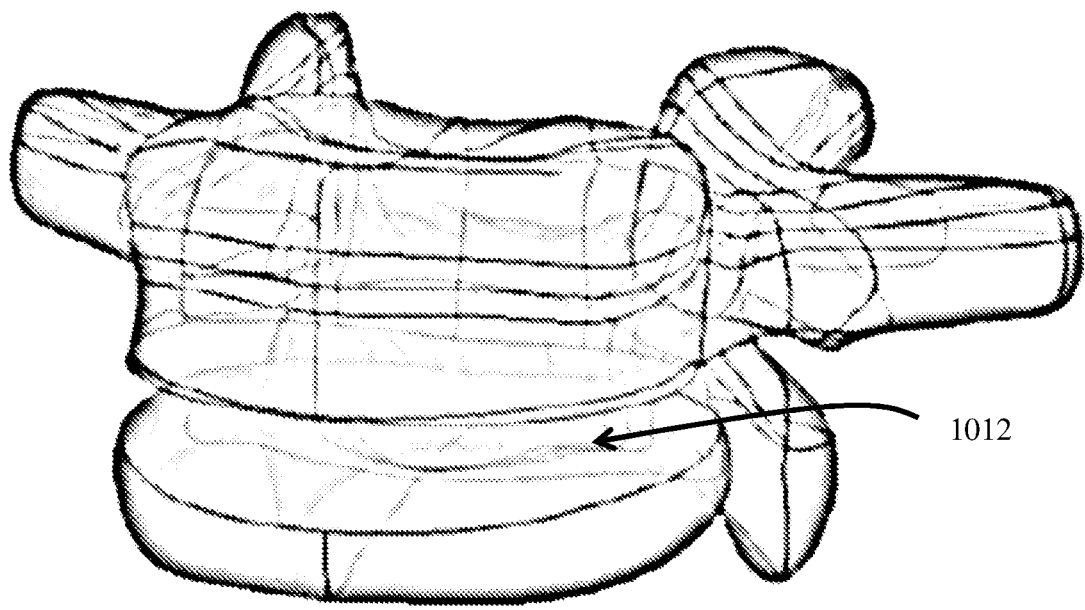
FIGS. 10A-10I illustrate one example of methods of implanting the implant system where

As shown in FIG. 10A, an osteotomy 1012 is made through the vertebral body from the concave side and inferior to the inferior aspect of the pedicle, preferably as parallel as possible to the inferior endplate. Shown is an osteotomy 1012 made from the concave side of the vertebrae. If only coronal correction is required, the far side cortex may be green-stick fractured. If coronal and sagittal correction is required, then a majority of the body may be cut, and the posterior lateral corner may be green-sticked or a complete osteotomy 1012 may be performed. Should the skilled artisan decide to approach the spine from the convex side, this is also possible and within the artisan's skill set.

For a complete osteotomy, for other complete through cuts through the bone, or for implants between bones, a footprint sizer tool (for example only, see example at FIG. 21) may be used to size the implant device size to be used. Additionally, for example as shown in FIGS. 23A and 23B, a far-side elevator tool may be inserted into the space between the bones and the handle may be turned to turn the paddle on its distal end to clear obstructions on the far side of the implant location.

The distal forked end of the implant insertion channel guide (for example only, see example at FIGS. 11A-11B) is positioned with its distal tip in the osteotomy. The insertion stop, the anterior stop and the cleat are used to engage the bone and properly maintain the position of the distal forked end of the implant insertion channel guide.

The insertion handle assembly is secured to the implant using the threaded locking rod (for example only, see example at FIGS. 13A-13C, 14 and 15).

Figure 10B:
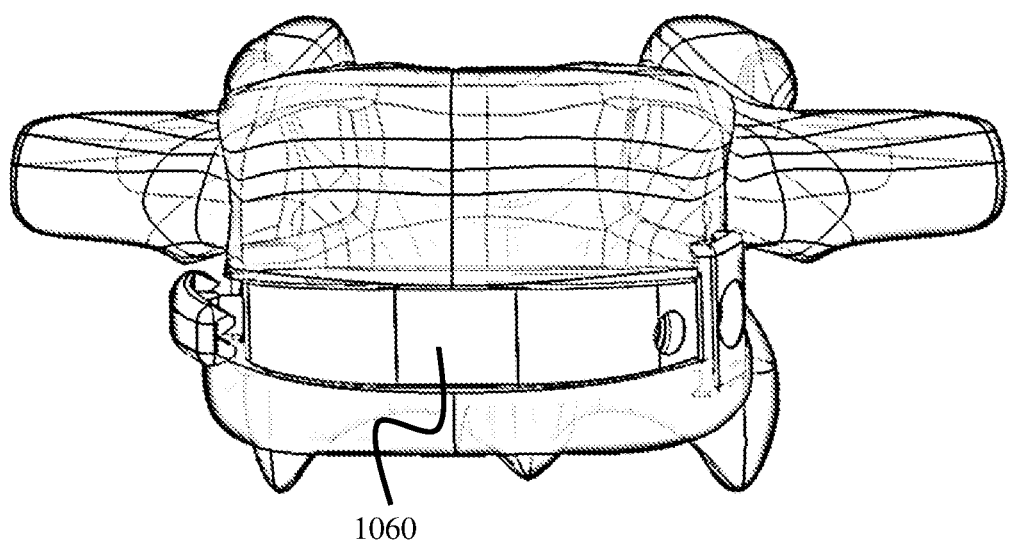

The handle, locking rod and cage are positioned in the implant insertion channel guide (for example only, see example at FIGS. 16A-16B) and the cage is advanced and positioned in the osteotomy space (for example only, see example at FIG. 10B).

Prior to implanting, the cage may be filled with bone graft material of choice. During this step, the staple is in an insertion position to pass through the osteotomy site with the cage. With the cage in place, the implant insertion channel guide can then be removed.

The staple drive handle assembly is positioned in the insertion handle assembly (for example only, see example at FIG. 17) and the distal end of the staple drive handle assembly is positioned over the engagement portion of the staple shaft and nut (for example only, see example at FIG. 18A) so that it can engage and rotate the staple shaft and the nut independently. If needed, the staple shaft and staple may be moved to an extended position further away from the distal end of the cage so that the staple is positioned outside of the osteotomy and beyond the opposite side boarder of the vertebral walls. This extended position may be accomplished by (1) holding the staple shaft drive rod (e.g., inner rod) of the assembly so that the staple shaft does not rotate and (2) rotating the nut drive rod (e.g., outer rod) of the assembly to turn the nut and have the nut engage the threads of the staple shaft to extend the staple shaft and staple away from the cage. The use of multiple nested drive rods can allow the rotation of one drive rod while not rotating the other (for example only, see examples in FIGS. 18A, 18B and 42D-42I). Once the staple is in the extended position, the staple drive handle assembly engaging the engagement portion of the staple shaft is rotated to rotate the staple shaft and position the staple (for example only, see examples in FIGS. 38A, 38B, 39A, 39C and 40A-40E) into the deployed position. The rotational movement may be influenced by the key and the cage stop to stop rotation or increment the rotation through rotational angles. For example, the cage stop and the key may increment the rotation of the staple through degree increments such as for example only 6 degree increments. While holding the inner drive rod of the staple drive handle steady, to maintain the alignment of the staple head, the drive rod of the staple drive handle assembly engaging the nut may then be rotated in the other direction to turn the nut and retract the staple shaft and head towards the cage to have the staple tines and the tab to engage the wall of the vertebral body and secure the implant device to the vertebral body in the stabilized position. This retraction also locks the key and cage stop to maintain the alignment of the staple head. The near side of the implant device may help secure the implant device with a proximal tab or an anchor frame. The staple may be one or more of a distal staple configured to engage the far side vertebra wall or an inner staple configured to engage the cancellous bone of the vertebral body. The staple drive handle assembly may then be removed or it may stay engaged to help stabilize the implant device.

Figure 10C:
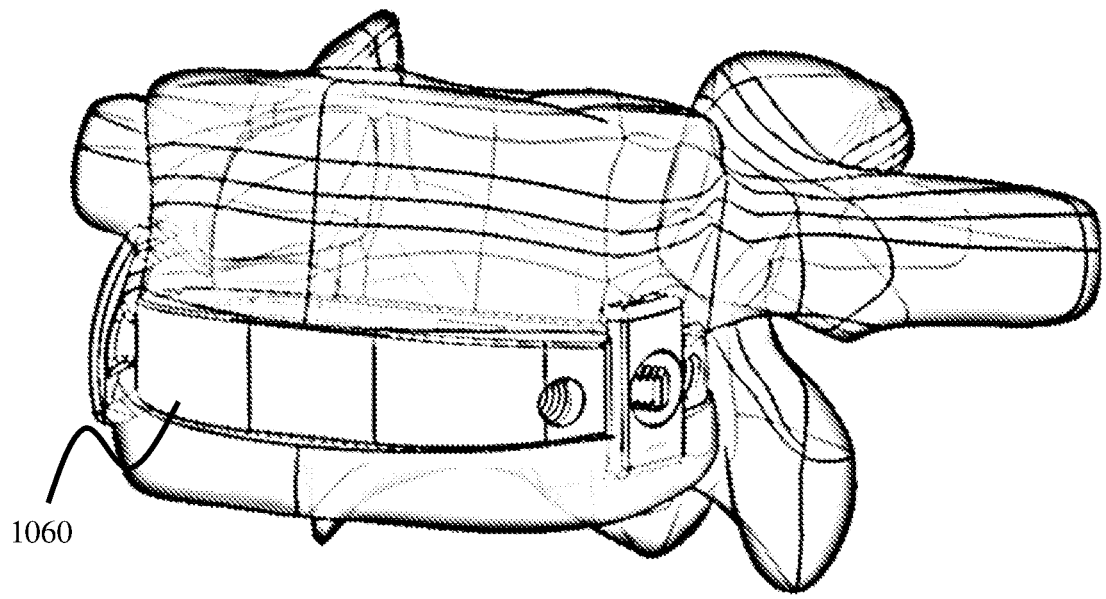
Figure 10D:
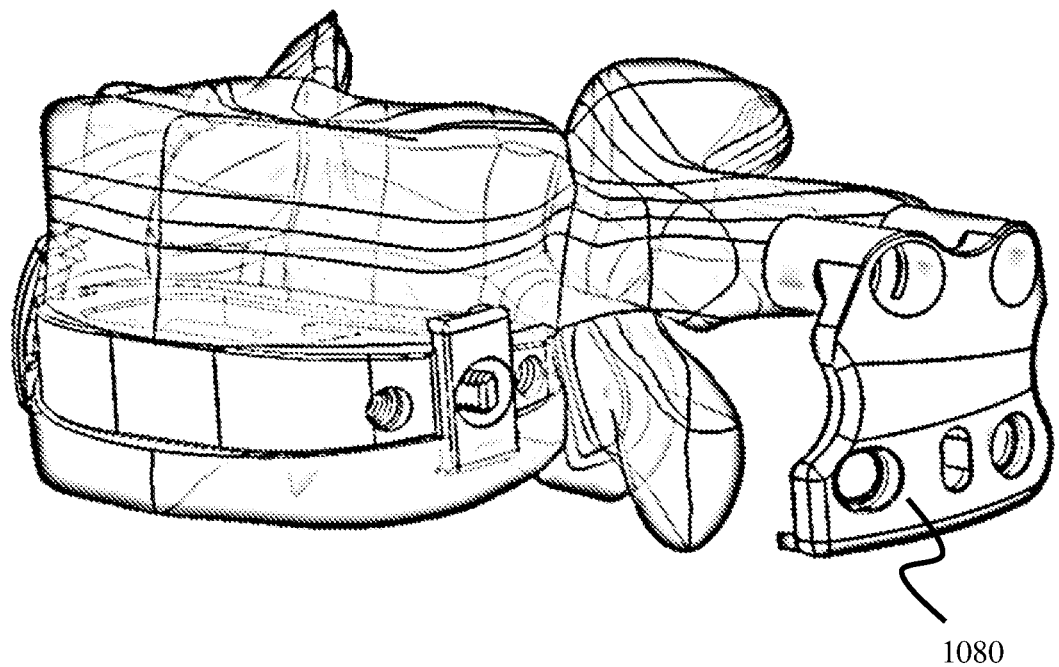
Figure 10E:
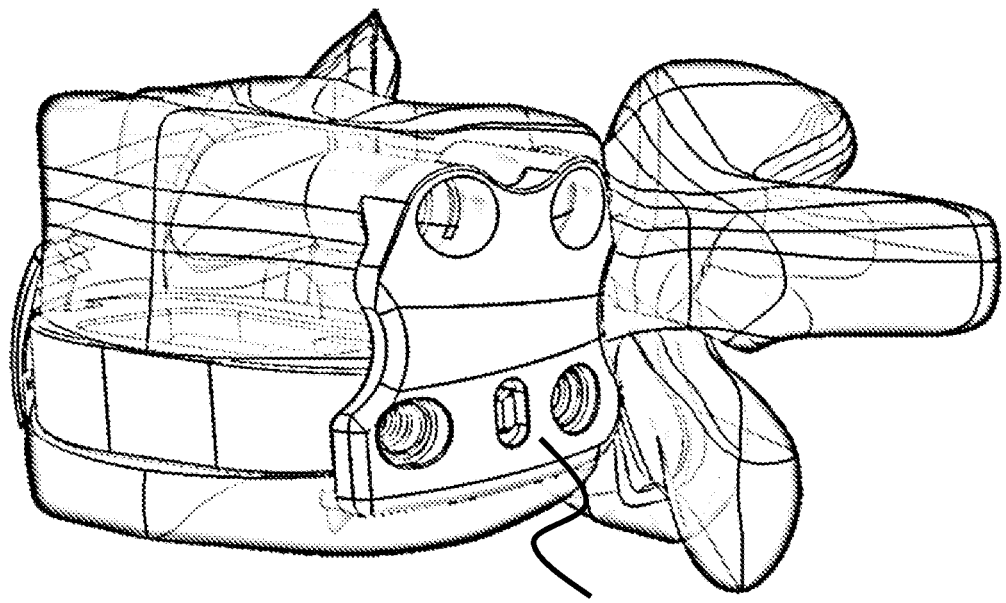
Figure 10F:
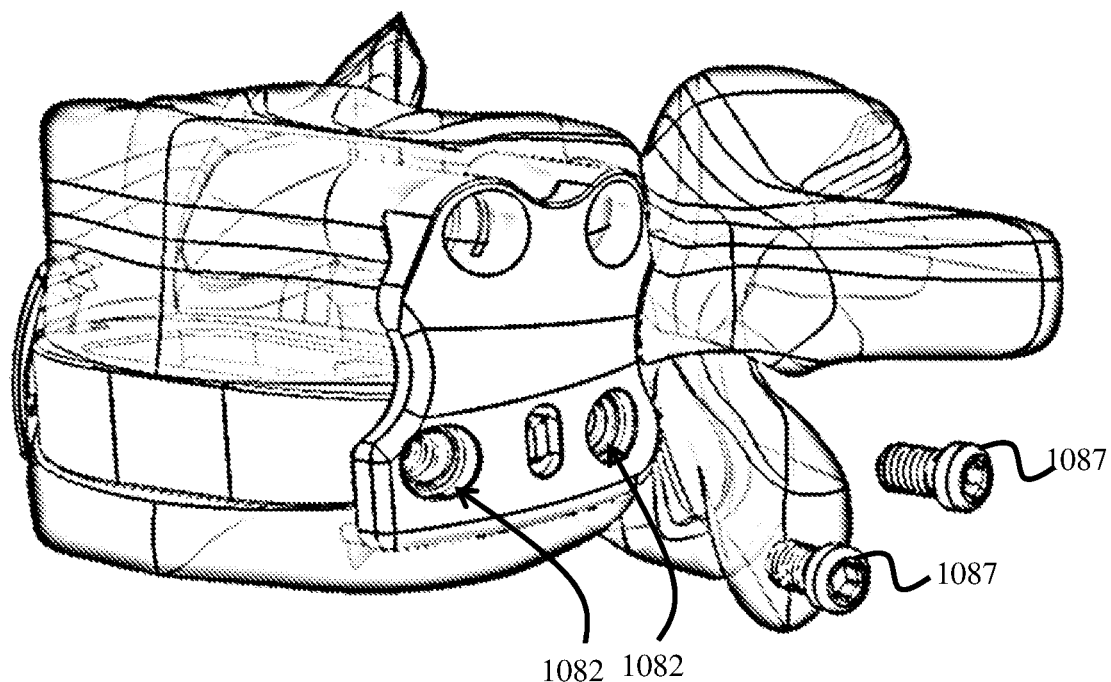
Figure 10G:
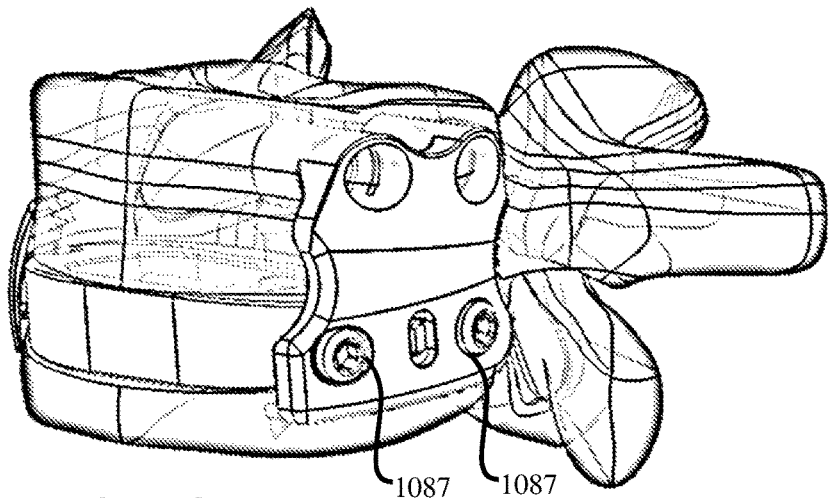
Figure 10H:
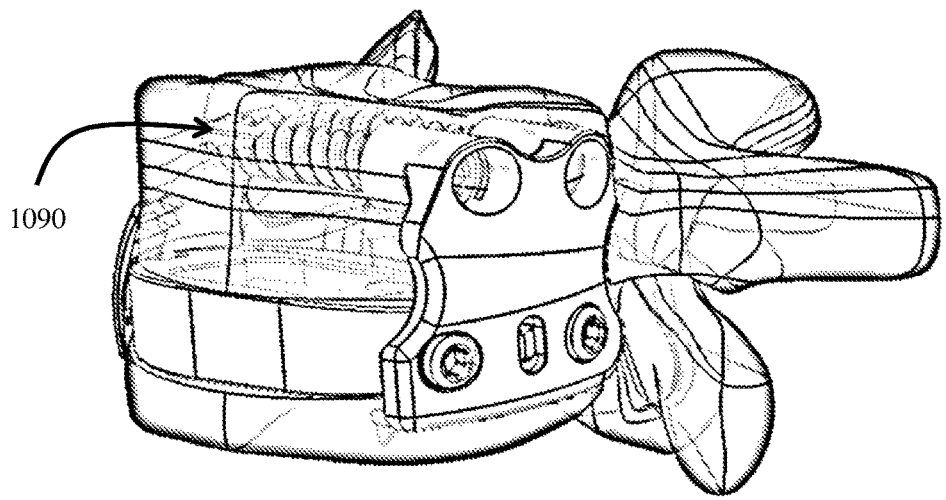
Figure 10I:
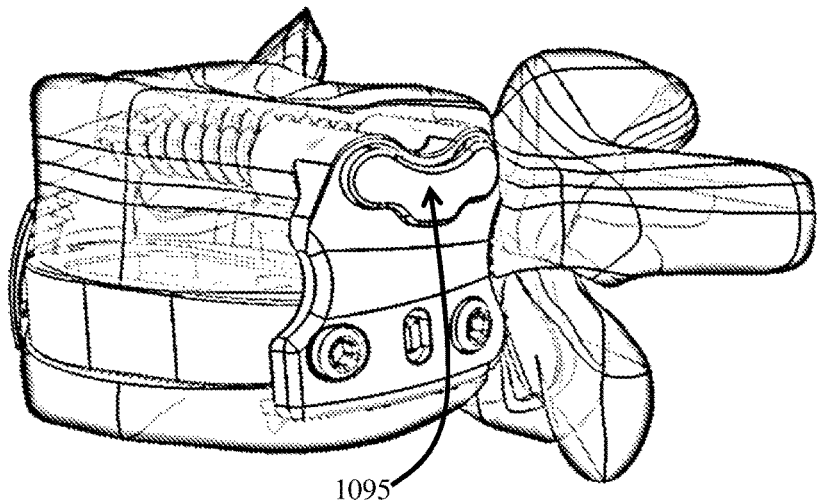

For examples of the implant system with anchor posts in the anchor frame and the need for counter bores, the anchoring members are positioned and secured to the vertebral body following the procedures below:

> With the cage 1060 in place and stable as shown in FIGS. 10B and 10C, a sizing template for the appropriate anchor frame may be placed on a handle and over a drill guide handle and into the handle so that it's positioned over the cage. The sizing template is used to ensure the counter bores and the cancellous bone screws will be placed properly in relation to the bone and the cage. For intravertebral implant systems, this may be just inferior to the superior endplate. The sizing template may also be used to determine the correct size of anchor frame to be implanted. The sizing template can then be removed.
>
> With the appropriate anchor frame sized, the appropriate drill guide and drill guide handle may be positioned over the locking rod and into the handle.
>
> Counter bores may be predrilled for the cancellous bone screws through the drill guide. With the counter bores drilled, the drill guide can then be removed. The handle may also be removed. In some embodiments, the handle is removed by depressing a locking rod lock to remove the handle from the locking rod.
>
> An anchor frame and anchor frame guide may be coupled and positioned over the locking rod to position the anchor frame with respect to the vertebral body and the cage.
>
> As shown in FIGS. 10D and 10E, with the anchor frame guide, the anchor frame 1080 is positioned over the engagement portion of the staple shaft with the anchor frame extensions in the counter bores for the cancellous bone screws.
>
> The cage screws 1087 may be inserted through the anchor frame through holes 1082 and tightened in the threaded holes in the cage (see FIGS. 10F and 10G) using a tool such as but not limited to a screwdriver. With the anchor frame guide still coupled to the anchor frame, only the cage screw on the unobstructed side can be inserted. The cage screws may incorporate an anti-backout thread design (e.g., spiral-lock) or other anti-backout elements 1095 to prevent loosening or disengagement of the cage from the anchor frame once it is implanted.
>
> The bone screws 1090 may also be inserted through the anchor frame extensions and through holes (see FIG. 10H) using a tool such as but not limited to a screwdriver. With the anchor frame guide still coupled, both bone screws may be inserted into the vertebral body. The anchor frame guide may then be removed.
>
> As shown in FIG. 10I, the bone screw anti-backout feature may be positioned over the heads of the cancellous bone screws to prevent them from backing out.
>
> The locking rod may now be removed and another cage screw may be inserted into the cage screw recess of the anchor frame to completely couple the anchor frame and the cage. Should additional bone graft material be desired within the cage, the locking rod may be removed and the additional bone graft material may be delivered into the cage cavity through the threaded cage screw recess/hole prior to inserting the second cage screw.

For implant systems that secure the anchor frame and implant device to the vertebral body directly through holes in the anchor frame, without the need for counter bores, anchoring members may be positioned and secured to the vertebral body following the procedures below:

> For implant systems where the anchor frame may be separable from the cage (for example only, see examples in FIGS. 2, 6A, 25B, 25C, 29B, 30B, 31B and 32B), the anchor frame may be coupled to the cage with cage screws using the anchor frame guide as described above. The anchoring members (e.g., bone screws) may then be inserted through the anchor frame and through holes using a tool such as but not limited to a screwdriver. The locking rod may now be removed and another cage screw, if needed, may be inserted into the cage screw recess of the anchor frame to completely couple the anchor frame and the cage.
>
> For implant systems where the anchor frame is already coupled to the cage and there is no need to further couple the anchor frame to the cage (for example only, see examples in FIGS. 35A, 36A, 37A, 38A, 38B, 39A and 39C), once the cage and anchor frame are positioned, the anchoring members (e.g., bone screws) may be inserted through the anchor frame and through holes using a tool such as but not limited to a screwdriver. With the anchor frame locking rod still coupled, all bone screws may be inserted into the vertebral body. The anchor frame locking rod may then be removed.

For implant systems with cage screws, the cage screws may incorporate an anti-backout thread design (e.g., spiral-lock) or anti-backout elements to prevent loosening or disengagement of the cage from the anchor frame once it is implanted.

For some embodiments, a bone screw anti-backout feature may be positioned over the heads of the bone screws to prevent them from backing out.

For some embodiments, should additional bone graft material be desired within the cage, the locking rod may be removed and the additional bone graft material may be delivered into the cage cavity through the threaded cage screw recess/hole.

Appropriate instrumentation as known to a skilled artisan would be provided to the surgeon to assist and facilitate every step of the above implantation procedure. These instruments would include but not be limited to, cutting guides, cage introducer/retractor, cage inserter/holders, sizing template, drill template, drill bits, plate holder/introducer and screwdrivers. A skilled artisan would also adapt these instruments appropriately to accommodate the desired surgical approach; anterior-to-psoas (ATP), oblique or direct lateral.

In some embodiments, the implant device may provide additional correction in the sagittal plane. In these embodiments, the cage surface planes may have different angles between them to affect correction in the coronal and sagittal plane. The transverse angle of the cage may additionally provide some correction in the sagittal plane when implanted from a lateral approach.

In some embodiments, the implant device may be inserted from other approaches or may be used to alter alignment in other planes. With other approaches, the general method of inserting and securing the implant device is similar to the methods above. The different approach direction may require different configurations of the implant device and associated instrumentation so that the exterior surface planes of the implant device provide the desired alteration in superior endplate surface plane and the inferior endplate surface plane of the vertebra in the appropriate plane.

An Example Implant System in Operation:

The above procedures generally describe use of the implant system for use as an intravertebral implant system. For implant systems used as an intervertebral implant system, similar tools and methods may be used. Rather than implant the implant device between the two sections of one vertebral body after an osteotomy, these implant systems are implanted between the end plates of two opposing vertebral bodies.

An Example Implant System in Operation:

For implant systems configured for use with other joints in an arthrodesis procedure, similar tools and methods may be used as those described for vertebral implant systems. The tools may be sized differently to accommodate the size and location of the joint being fused.

An Example Implant System in Operation:

Operation of one example of an implant system with a screw plate alignment system generally comprises the following sequence of steps:

- Surgical access is provided to the vertebral body and an osteotomy is made through the vertebral body inferior to the pedicle as described above.
- The cage is positioned in the vertebral body and an anchor frame with threaded through holes for the bone screws is positioned on the sidewall of the vertebral body.
- A bone screw is positioned through the anchor frame through hole and screwed into the vertebral body with the screw driver. The screw driver drives the bone screw into the bone until the drive stop limit of the screw driver hits the staple plate surface limiting the insertion of the screw to a predefined limit. The screw driver is removed and the process is repeated for other bone screws.
- With the tipped bone screw positioned in the bone and the anchor frame, the securing element is positioned in the hollow tip of the lock driver and the bore of the securing element is positioned over the tip of the bone screw with the lock driver. The tapered end of the locking element is then pushed into the threaded recess of the anchor frame through hole and the lock driver is turned to have the exterior surface of the locking element engage the threads on the interior surface of the through hole. When the locking element is secure, a torque limit is reached at the tip of the lock driver and the locking element is broken off and left anchored to the anchor frame. The lock driver, securing element and locking element are replaced and this step is repeated for another tipped bone screw until the anchor frame and bone screws are secured to the vertebral body.
- It is understood that the method may also be performed by securing each tipped bone screw to the staple plate before moving to the next tipped bone screw.

It is understood that these methods may be used in applications without osteotomies.

An Example Implant System in Operation:

In some implant systems, constructs may be provided on the implant system to couple the implant system to other constructs such as rod systems, flexible tethers, cords and plate systems. These constructs may include using tulip head screws or tether screws as anchoring elements to attach a longitudinal rod or a tether or cords to connect multiple vertebrae or multiple implant devices. These constructs may also include additional threaded recesses in the implant device, such as in the anchor frame, to receive vertebral body screws to attach to rods or tethers or cords to connect multiple vertebrae or multiple implant devices.

Figure 47:
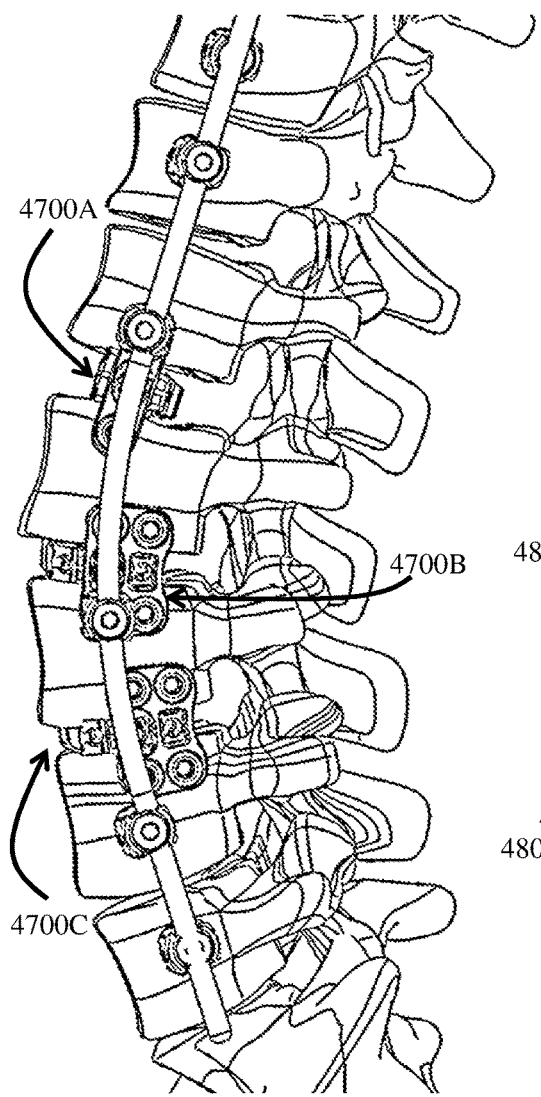
FIG. 47 shows an example of a spine corrected using an embodiment of the implant system using the implant system as intervertebral implants.
Figure 48:
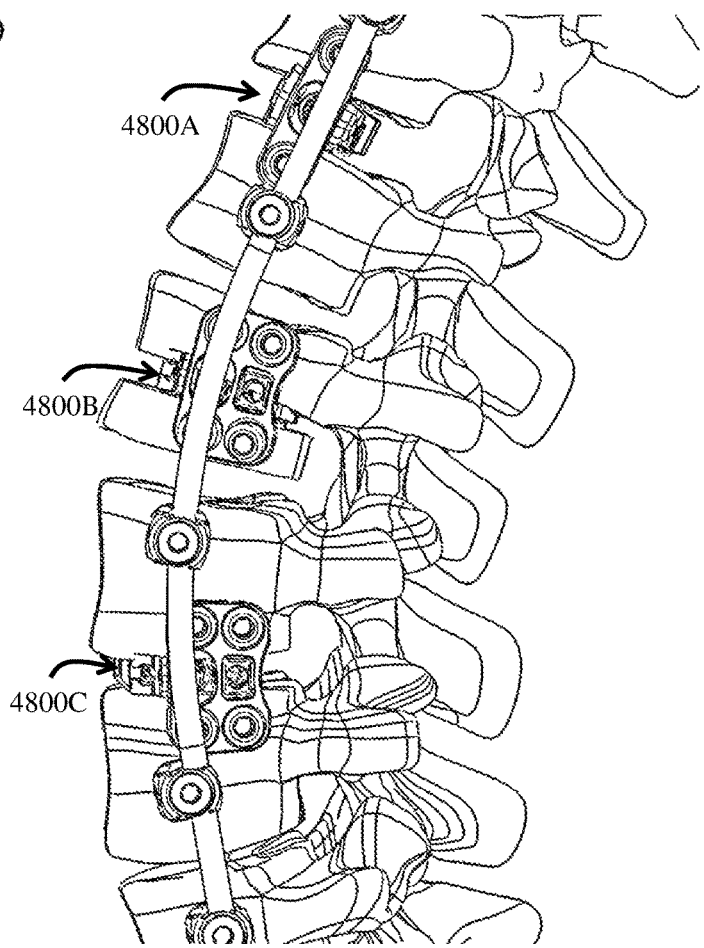
FIG. 48 shows an example of a spine corrected using an embodiment of the implant system combining use of the implant system as both intervertebral and intravertebral implants.
Figures 49A, 49B:
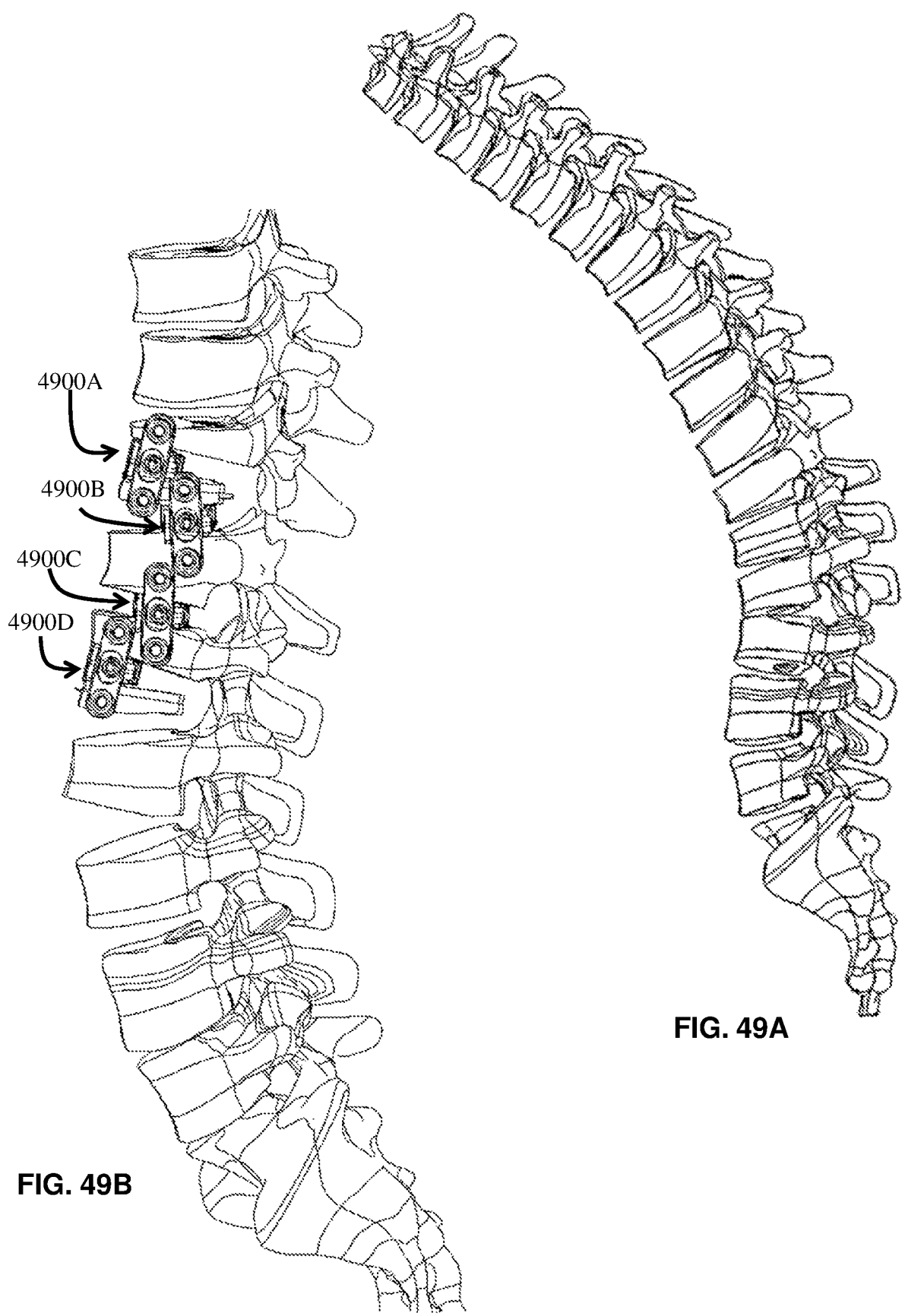
FIG. 49A shows an example of an uncorrected spine with kyphosis.
FIG. 49B shows an example of the spine correcting the kyphosis using embodiments of the implant system as both intervertebral and intravertebral implants.

Some implant systems may be used with non-fusion techniques such as controlling the overall main deformity with vertebral body screws and cords (also called Tethering, Vertebral Body Tethering (VBT) or Anterior Scoliosis Correction (ASC)) or a vertebral body wedge correction with the implant in the intrabody (for example only and not for limitation, see FIG. 46) or the interbody (for example only and not for limitation, see FIG. 47) or any combination of the these applications (for example only and not for limitation, see FIGS. 48 and 49B). With these techniques, a rod or tether or cord may be secured to vertebrae both above/cephalad the area of correction and below/caudad the area of correction. Between these secured points, implant systems may be implanted as intervertebral implants and secured to the rod or tether or cord.

Figure 45:
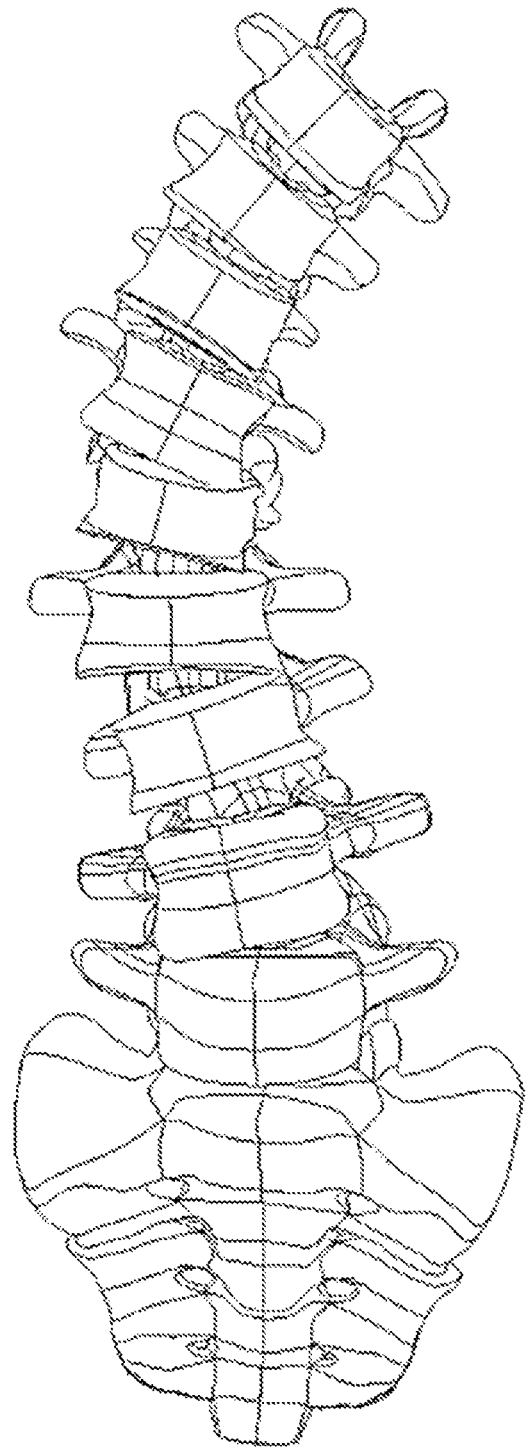
FIG. 45 shows an example of a misaligned spine to be corrected for scoliosis.
Figure 46:
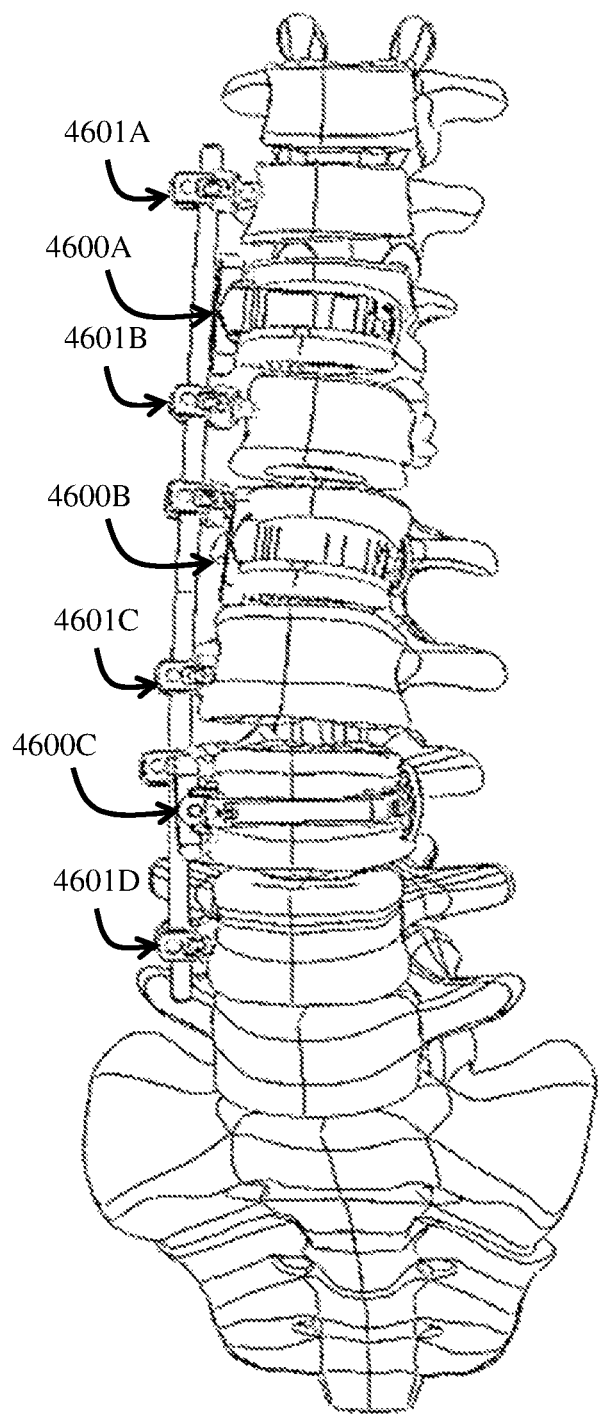
FIG. 46 shows a profile of the corrected spine with three intervertebral implants and tether screws coupled to a longitudinal rod or tether or cord.

FIG. 45 shows a coronal view of a spine to be corrected for scoliosis. In this example, three osteotomies would be performed on three vertebrae to receive three implant devices to be used as intervertebral implants. FIG. 46 shows a profile of the corrected spine with three intervertebral implants 4600A-4600C and four vertebral body tether screws 4601A-4601D, including one 4601A above and one 4601D below the area of correction. In this example, a thoracolumbar or lumbar scoliosis correction is shown and the intervertebral implants and screws are coupled to a longitudinal rod or tether or cord. It is understood that the disclosed implant systems and techniques may be used with other sections of the spine such as for thoracic correction.

FIG. 47 shows a sagittal view of an example of correcting a spine using the tether construct and using implant devices as intervertebral implants. In this example, a thoracolumbar or lumbar scoliosis correction is shown and osteotomies are not necessary. And in this example, the intervertebral implants include example implant systems with both two hole 4700A and four hole anchor frames 4700B and 4700C. It is understood that the disclosed implant systems and techniques may be used with other sections of the spine such as for thoracic correction.

FIG. 48 shows a sagittal view of an example of a thoracolumbar or lumbar scoliosis correction using the tether construct and using implant devices as both intravertebral and intervertebral implant devices. In this example, implant device 4800A has a two hole anchor frame and is used as an intervertebral implant device, implant device 4800B has a four hole anchor frame and is used as an intravertebral implant device and implant device 4800C has a four hole anchor frame and is used as an intervertebral implant device. It is understood that the disclosed implant systems and techniques may be used with other sections of the spine such as for thoracic correction.

FIG. 49A shows a sagittal view of a spine to be corrected for kyphosis. To correct for kyphosis, the processes and devices used are similar to those used to correct for scoliosis. The difference from a coronal correction for scoliosis being the orientation of the surface plane angles of the cage are angled sufficient to provide the sagittal correction when implanted. In this example, osteotomies would be performed on vertebrae to receive the vertebral implant devices. FIG. 49B shows sagittal view of the corrected spine with implant devices 4900A and 4900D used as an intravertebral implant devices and implant devices 4900B and 4900C used as an intervertebral implant devices. In this example, no longitudinal rod or tether or cord is needed. It is understood that as for scoliosis corrections, the disclosed implant systems and techniques may be used with other sections of the spine such as for thoracic correction and may be used with implant systems only used as either intervertebral or intravertebral implant devices as well as in combinations.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. An orthopedic implant device configured to be implanted across a vertebral body of a vertebrae, the orthopedic implant device comprising:
   a cage;
   an anchor frame pivotally coupled to the cage;
   a staple comprising a staple head and a staple shaft;
   the staple shaft configured to rotate the staple head from an extended position extended from the cage to a deployed position;
   the staple shaft configured to rotate relative to the cage about a shaft longitudinal axis;
   the anchor frame configured to pivot about an axis that is a different axis than the shaft longitudinal axis;
   wherein the orthopedic implant device is configured to be implanted across the vertebral body of the vertebrae;
   the cage further comprising at least one cage stop;
   the at least one cage stop comprises a radially grooved surface;
   the staple shaft having an engagement portion configured to mate with an engagement tool whereby when the engagement tool is rotated, the staple shaft is rotated;
   the staple shaft coupled to a key;
   the key comprising a radially grooved washer shaped to be coupled to and mate with the engagement portion of the staple shaft; and
   the radially grooved washer having a radially grooved surface configured to mesh with the radially grooved surface of the at least one cage stop whereby when the staple head is retracted to a stabilized position, the staple shaft is rotationally locked in a radial position relative to the cage.

2. The orthopedic implant device of claim 1 wherein:
   a longitudinal axis of the cage is configured to extend laterally across the vertebral body of the vertebrae; and
   the orthopedic implant device is configured to be implanted from a lateral direction relative to the vertebral body and the staple head is configured to secure the orthopedic implant device to a distal lateral sidewall of the vertebral body.

3. The orthopedic implant device of claim 1 wherein:
   the orthopedic implant device is configured to be implanted from one of an anterior or an oblique direction relative to the vertebral body and the staple head is configured to secure the orthopedic implant device to a distal lateral sidewall of the vertebral body.

4. The orthopedic implant device of claim 1 wherein:
   the staple shaft is received in a through bore of the cage; and
   the through bore of the cage extends along a longitudinal axis of the cage from a first lateral side of the cage to a second lateral side of the cage.

5. The orthopedic implant device of claim 1 wherein:
   the extended position comprises a neutral alignment of the staple head and an extended location of the staple head extended a distance away from the cage; and
   the deployed position comprises a non-neutral alignment of the staple head and the extended location of the staple head away from the cage.

6. The orthopedic implant device of claim 1 wherein the staple shaft is further configured to move the staple head from an insertion position to the extended position.

7. The orthopedic implant device of claim 6 wherein:
   the insertion position comprises a neutral alignment of the staple head and a non-extended location relative to the cage; and
   the extended position comprises the neutral alignment of the staple head and an extended location of the staple head away from the cage.

8. The orthopedic implant device of claim 1 wherein the staple shaft is further configured to move the staple head from the deployed position to the stabilized position.

9. The orthopedic implant device of claim 8 wherein:
   the deployed position comprises a non-neutral alignment of the staple head and an extended location of the staple head away from the cage; and
   the stabilized position comprises the non-neutral alignment of the staple head and a retracted location of the staple head retracted towards the cage.

10. The orthopedic implant device of claim 1 wherein:
    the staple shaft is received in a through bore of the cage; and
    the staple shaft is rotatable within the through bore of the cage whereby the staple shaft is configured to move the staple head from the extended position to the deployed position relative to the cage.

11. The orthopedic implant device of claim 1 wherein:
    the staple shaft is received in a through bore of the cage; and
    the staple shaft is longitudinally slidable within the through bore of the cage whereby the staple shaft is configured to slidably move the staple head from an insertion position to the extended position extended away from the cage.

12. The orthopedic implant device of claim 1 wherein:
    the staple shaft is received in a through bore of the cage; and
    the staple shaft is longitudinally slidable within the through bore of the cage whereby the staple shaft is configured to slidably move the staple head from the deployed position to the stabilized position retracted towards the cage.

13. The orthopedic implant device of claim 1 wherein the orthopedic implant device further comprises a threaded nut.

14. The orthopedic implant device of claim 13 wherein:
    the staple shaft having a threaded portion; and
    the threaded nut configured to mate with the threaded portion of the staple shaft whereby when the threaded nut is rotated, the threaded nut engages the threaded portion of the staple shaft and the staple head is moved away from the cage.

15. The orthopedic implant device of claim 13 wherein:
    the staple shaft having a threaded portion; and
    the threaded nut configured to mate with the threaded portion of the staple shaft whereby when the threaded nut is rotated, the threaded nut engages the threaded portion of the staple shaft and the staple head is retracted towards the cage.

16. The orthopedic implant device of claim 13 wherein:
the staple shaft having a threaded portion;
the engagement portion of the staple shaft configured to be engaged by a shaft engagement portion of the engagement tool whereby the shaft engagement portion of the engagement tool is configured to rotate the staple shaft and move the staple head from the extended position to the deployed position;
the threaded nut configured to be engaged by a nut engagement portion of the engagement tool to rotate the threaded nut;
the threaded nut is configured to mate with the threaded portion of the staple shaft whereby when the threaded nut is rotated in a first direction, the threaded nut engages the threaded portion of the staple shaft and the staple head is extended away from the cage; and
the threaded nut is configured to mate with the threaded portion of the staple shaft whereby when the threaded nut is rotated in a second direction, the threaded nut engages the threaded portion of the staple shaft and the staple head is retracted towards the cage.

17. The orthopedic implant device of claim 13 wherein the threaded nut is received in a retaining channel of the cage whereby a longitudinal position of the threaded nut relative to the cage is constrained by the retaining channel.

18. The orthopedic implant device of claim 1 wherein the anchor frame pivots about the axis which is about ninety degrees to the shaft longitudinal axis.

19. The orthopedic implant device of claim 1 wherein the anchor frame pivots about the axis which is about ninety degrees to a longitudinal axis of the cage.

20. The orthopedic implant device of claim 1 wherein:
the radially grooved washer has a through hole shaped to be coupled to and mate with the engagement portion of the staple shaft.

21. The orthopedic implant device of claim 1 configured to alter an endplate surface plane of the vertebral body.

22. The orthopedic implant device of claim 1 wherein:
the staple shaft is received in a through bore of the cage;
the through bore of the cage extends from a first lateral side of the cage to a second lateral side of the cage;
the staple shaft is rotatable within the through bore of the cage whereby the staple shaft is configured to move the staple head from the extended position to the deployed position relative to the cage;
the staple shaft is longitudinally slidable within the through bore of the cage whereby the staple shaft is configured to slidably move the staple head from an insertion position to the extended position away from the cage;
the staple shaft is longitudinally slidable within the through bore of the cage whereby the staple shaft is configured to slidably move the staple head from the deployed position to the stabilized position when retracted towards the cage;
the orthopedic implant device further comprises a threaded nut configured to mate with a threaded portion of the staple shaft whereby when the threaded nut is rotated, the threaded nut engages the threaded portion of the staple shaft and the staple head is moved away from the cage; and
the anchor frame further comprises at least one pivot connection configured to pivotally couple the anchor frame to the cage.

23. An orthopedic implant device configured to extend laterally across a vertebral body, the orthopedic implant device comprising:
a cage;
an anchor frame;
a staple;
the anchor frame pivotally coupled to the cage;
the anchor frame, the staple and the cage operably coupled;
whereby the anchor frame and the staple are configured to be secured to opposite lateral sidewalls of the vertebral body;
the staple configured to rotate relative to the cage about a staple rotation axis;
the anchor frame configured to pivot about an axis that is a different axis than the staple rotation axis;
whereby the cage is configured to be secured to extend laterally across the vertebral body;
the cage further comprising at least one cage stop;
the at least one cage stop comprises a radially grooved surface;
the staple comprising a staple shaft having an engagement portion configured to mate with an engagement tool whereby when the engagement tool is rotated, the staple shaft is rotated;
the staple shaft coupled to a key;
the key comprising a radially grooved washer shape to be coupled to and mate with the engagement portion of the staple shaft; and
the radially grooved washer having a radially grooved surface configured to mesh with the radially grooved surface of the at least one cage stop whereby when the staple is retracted to a stabilized position, the staple shaft is rotationally locked in a radial position relative to the cage.

24. The orthopedic implant device of claim 23 wherein:
the staple comprises a staple head and the staple shaft;
the cage comprises a through bore extending longitudinally through the cage; and
the staple shaft received in the through bore of the cage to operably couple the cage and the staple.

25. The orthopedic implant device of claim 23 wherein:
the staple comprises a staple head and the staple shaft;
the orthopedic implant device further comprises a coupling element; and
the coupling element configured to engage the staple shaft and operably couple the staple to the cage whereby the coupling element adjusts a positional relationship of the staple head and the anchor frame whereby the staple head and the anchor frame are configured to be secured to the opposite lateral sidewalls of the vertebral body by a compression force.

26. The orthopedic implant device of claim 25 wherein:
the coupling element comprises a threaded nut configured to engage a threaded portion of the staple shaft whereby the coupling element adjusts the positional relationship of the staple head and the anchor frame.

27. A method to secure a first bone portion to a second bone portion, the method comprising:
providing an orthopedic implant device comprising:
a cage,
a staple,
an anchor frame,
the cage coupled to the staple,
the anchor frame pivotally coupled to the cage about a pivot axis,
the staple comprising a staple head and a staple shaft, the staple shaft configured to rotate the staple head from an extended position extended from the cage to a deployed position, the staple shaft configured to rotate relative to the cage about a shaft longitudinal axis, the anchor frame configured to pivot about the pivot axis that is a different axis than the shaft longitudinal axis, wherein the orthopedic implant device is configured to be implanted across the first bone portion and the second bone portion, the cage further comprising at least one cage stop, the at least one cage stop comprises a radially grooved surface, the staple shaft having an engagement portion configured to mate with an engagement tool whereby when the engagement tool is rotated, the staple shaft is rotated, the staple shaft coupled to a key, the key comprising a radially grooved washer shaped to be coupled to and mate with the engagement portion of the staple shaft, and the radially grooved washer having a radially grooved surface configured to mesh with the radially grooved surface of the at least one cage stop whereby when the staple head is retracted to a stabilized position, the staple shaft is rotationally locked in a radial position relative to the cage;

inserting the cage and the staple into an opening between the first bone portion and the second bone portion;

positioning the staple head in the deployed position by rotating the staple head about the shaft longitudinal axis; and securing the anchor frame to the first bone portion and the second bone portion by retracting the staple head towards the cage and/or the anchor frame.

28. The method of claim 27 further comprising positioning the staple head in the stabilized position to secure the staple to the first bone portion and the second bone portion whereby the staple further secures the cage to the first and the second bone portions.

* * * * *